United States Patent
Tabor et al.

(10) Patent No.: US 11,344,611 B2
(45) Date of Patent: May 31, 2022

(54) POLYPEPTIDE, COMPOSITIONS AND USES THEREOF

(71) Applicants: MEAT & LIVESTOCK AUSTRALIA LIMITED, North Sydney (AU); THE STATE OF QUEENSLAND, Brisbane (AU)

(72) Inventors: Alicja Tabor, Brisbane (AU); Matthew Bellgard, Brisbane (AU); Manuel Rodriguez Valle, Brisbane (AU)

(*) Notice: Subject to any disclaimer, the term of this patent is extended or adjusted under 35 U.S.C. 154(b) by 0 days.

(21) Appl. No.: 16/966,932

(22) PCT Filed: Feb. 6, 2018

(86) PCT No.: PCT/AU2018/050081
§ 371 (c)(1),
(2) Date: Aug. 3, 2020

(87) PCT Pub. No.: WO2019/153029
PCT Pub. Date: Aug. 15, 2019

(65) Prior Publication Data
US 2021/0205424 A1     Jul. 8, 2021

(51) Int. Cl.
| | | |
|---|---|---|
| *A61K 39/00* | (2006.01) | |
| *A61K 47/64* | (2017.01) | |
| *A61K 9/00* | (2006.01) | |
| *A61K 39/39* | (2006.01) | |

(52) U.S. Cl.
CPC ........ *A61K 39/0003* (2013.01); *A61K 9/0021* (2013.01); *A61K 39/39* (2013.01); *A61K 47/643* (2017.08); *A61K 47/646* (2017.08); *A61K 2039/545* (2013.01); *A61K 2039/552* (2013.01); *A61K 2039/6081* (2013.01)

(58) Field of Classification Search
CPC ................................................ A61K 39/0003
See application file for complete search history.

(56) References Cited

U.S. PATENT DOCUMENTS

| | | | | |
|---|---|---|---|---|
| 5,807,978 A | * | 9/1998 | Kokolus .......... | G01N 33/57434 424/184.1 |
| 2011/0245096 A1 | | 10/2011 | Aggarwal et al. | |
| 2013/0064843 A1 | | 3/2013 | Brusic et al. | |
| 2013/0273095 A1 | | 10/2013 | Rodriguez Mallon et al. | |
| 2016/0051649 A1 | | 2/2016 | Schetters et al. | |
| 2020/0062810 A1 | | 2/2020 | Tabor et al. | |

FOREIGN PATENT DOCUMENTS

WO   WO 2014/018427   1/2014

OTHER PUBLICATIONS

Barnard, Anette-Christi, "A reverse genetics approach to evaluate Metzincins as anti-Rhipicephalus microplus tick vaccine candidates," Ph.D. Thesis. University of Pretoria, Mar. 2013.https://repository.up.ac.za/bitstream/handle/2263/32964/Barnard_Reverse_2013.pdf. Retrieved Apr. 12, 2018.
Cunha et al., "Calculation of the efficacy of vaccines against tick infestations on cattle," *Rev. Bras. Parasitol. Vet.*, 22(4):571-8, 2013.
de Castro, "Sustainable tick and tickborne disease control in livestock improvement in developing countries," *Vet. Parasitol.*, 71:71-97, 1997.
de la Fuente et al., "Vaccination against ticks (*Boophilus* spp.): the experience with the Bm86-based vaccine Gavac," *Genet. Anal.*, 15:143-148, 1999.
Garcia-Garcia et al., "Sequence variations in the Boophilus microplus Bm86 locus and implications for immunoprotection in cattle vaccinated with this antigen," *Exp. App. Acar.*, 23:883-895, 1999.
Lew-Tabor and Rodriguez Valle, "A review of reverse vaccinology approaches for the development of vaccines against ticks and tick borne diseases," *Ticks & Tick Borne Diseases*, 7:573-585,2016.
Lew-Tabor et al., "Rhipicephalus (Boophilus) microplus tick in vitro feeding methods for functional (dsRNA) and vaccine candidate (antibody) screening," *Ticks and Tick Borne Diseases*, 5:500-510, 2014.
Lew-Tabor et al., "Suppressive subtractive hybridization analysis of Rhipicephalus (Boophilus) microplus transcript expression during feeding and attachment," *Veterinary Parasitology*, 167(2-4): 304-320, 2010.
PCT International Preliminary Report on Patentability issued in International Application No. PCT/AU2018/050080, dated May 1, 2018.
Piper et al., "Peripheral cellular and humoral responses to infestation with Rhipicephalus microplus in Santa-Gertrudis cattle," *Parasite Immunology*, 39:e12402, 2017.
Playford et al., "Review of research needs for cattle tick control, Phases I and II," In.: Meat & Livestock Australia Ltd., Locked Bag 991, North Sydney NSW 2059; ISBN 1 74036 74685 74039, 2005.
Rand et al., "Cloning and expression of a protective antigen from the cattle tick Boophilus microplus," *Proc. Natl. Acad. Sci. USA*, 86:9657-9661, 1989.
Almazan et al., "Identification and characterization of Rhipicephalus (Boophilus) microplus candidate protective antigens for the control of cattle tick infestations," Parasitology Research, 106:471-479, 2010.
Barnard, Anette-Christi, "A reverse genetics approach to evaluate Metzincins as anti-Rhipicephalus microplus tick vaccine candidates," Ph.D. Thesis. University of Pretoria, Mar. 2013.https://repository.up.ac.za/bitstream/handle/2263/32964/Barnard Reverse 2013. pdf. Retrieved Apr. 12, 2018.
De Rose et al., "Bm86 antigen induces a protective immune response against Boophilus microplus following DNA and protein vaccination in sheep," Veterinary Immunology and Immunopathology, 71:151-160, 1999.

(Continued)

*Primary Examiner* — Albert M Navarro
(74) *Attorney, Agent, or Firm* — Parker Highlander PLLC

(57) ABSTRACT

The present invention relates to tick polypeptides and compositions comprising the same, which are useful for treatment or prophylaxis of tick infestation in a subject.

23 Claims, No Drawings
Specification includes a Sequence Listing.

(56) References Cited

OTHER PUBLICATIONS

PCT International Search Report and Written Opinion issued in International Application No. PCT/AU2018/050081, dated Apr. 23, 2018.

* cited by examiner

POLYPEPTIDE, COMPOSITIONS AND USES THEREOF

This application is a national phase application under 35 U.S.C. § 371 of International Application No. PCT/AU2018/050081, filed Feb. 6, 2018, the entirety of which is incorporated herein by reference.

Pursuant to 37 C.F.R. 1.821(c), a sequence listing is submitted herewith as an ASCII compliant text file named "FPAPP0011US_ST25.txt", created on Jul. 31, 2020 and having a size of ~66 kilobytes. The content of the aforementioned file is hereby incorporated by reference in its entirety.

FIELD OF THE INVENTION

This invention relates generally to methods and compositions for stimulating immune responses in a subject to a tick polypeptide. The present invention further relates to the use of these methods and compositions for treating or preventing tick infestation.

BACKGROUND OF THE INVENTION

Beef exports contribute approximately $4.5 billion to the Australian economy (2010-2011). The control of cattle ticks is vital to the continued success of the cattle industry in terms of compliance with regulatory protocols for domestic and international livestock movement and to enhance animal welfare through avoiding stress and debilitation. These ticks transmit protozoan (*Babesia bovis* and *B. bigemina*) and bacterial (*Anaplasma marginale*) organisms which cause babesiosis and anaplasmosis ("tick fever"). The tick-disease complex is the most important affecting world-wide livestock production (deCastro, 1997), leading to severe economic losses in dairy and beef production and restriction in traffic of animals costing >$US22-30 billion annually (Lew-Tabor and Rodriguez Valle, 2016). For example, cattle industries in northern Australia incur approximately $175 million in annual losses, due to the impact of ticks (see, Playford et al., 2005).

Cattle are particularly susceptible when they first encounter ticks, but some individuals and breeds develop a degree of resistance after repeated exposure. *Bos indicus* cattle and crosses (tropical breeds which predominate in northern Australia) develop stronger resistance than do *Bos taurus* cattle (British & European breeds). Chemical treatments (acaricides) are used to control ticks, however ticks have developed resistance to most current acaricides, and there is a market imperative to reduce chemical residues in both cattle and the environment. An efficacious vaccine would allow the tick line to be diminished and minimize the use of synthetic acaricides applied to treat cattle for ticks, thereby decreasing chemical footprints in milk, meat and the environment.

The previously available tick vaccine (TICKGARD PLUS) was based on a concealed tick gut antigen Bm86, which was not boosted during natural tick challenge (Rand et al., 1989) was not effective against ticks from different geographical locations (Garcia-Garcia et al., 1999). As successful administration of TICKGARD PLUS requires three or four booster shots per year, it was poorly adopted and is now no longer manufactured commercially.

The economic benefits from reduced input costs and increased productivity due to a reduction in parasites, improved animal welfare and increased marker access (due to decreased chemical residues) has been estimated at around $98 million.

It has been estimated that 80% of the world population of 1,200 million cattle is at risk of ticks and tick-borne disease and global losses amount to around US$22-30 billion. Around 500 million cattle are exposed to babesiosis worldwide, and mortality rates of around 50% is common when susceptible cattle are imported into endemic areas. The cattle tick, *Rhipicephalus* (*Boophilus*) *microplus* is a major problem for cattle producers because of the direct effects of infestation and the diseases transmitted. Control of cattle ticks is required to ensure compliance with regulatory protocols for interstate and international livestock movement and to enhance animal welfare through avoiding stress and debilitation.

The application of traditional acaricides to control ticks has led to a rise in drug resistance problems among different regional populations of *R. microplus*. In Australia, for example, there are tick populations resistant to synthetic pyrethroids, amitraz and flumethren. There is also a need to develop less toxic chemicals for the control of tick infestations. In the case of tick-borne disease caused by *Babesia* species, there is only one drug currently registered for use.

There is a need for new treatments for preventing or reducing the incidence of tick infestations in cattle populations.

SUMMARY OF THE INVENTION

The present inventors have identified a polypeptide antigen that has utility in therapeutic and prophylactic applications for combating tick infestations.

Accordingly, in one aspect, the present invention provides a composition for forming an immune response in a subject to a tick antigen, the composition comprising a recombinant or synthetic polypeptide comprising, consisting of or consisting essentially of an amino acid sequence corresponding to the M1-2A Clone 91 polypeptide as herein described.

In any embodiment, the sequence of the M1-2A Clone 91 polypeptide comprises, consists of or consists essentially of the amino acid sequence as set forth in SEQ ID NO: 1.

The present invention also contemplates the use of immunogenic fragments, or variant sequences derived from SEQ ID NO: 1, for use in the compositions herein described. As such, the present invention also provides a composition for forming an immune response in a subject to a tick antigen, the composition comprising a immunogen in the form of a polypeptide having an amino acid sequence corresponding to an immunogenic fragment of M1-2A Clone 91 polypeptide, wherein the fragment comprises, consists of or consists essentially of the amino acid sequence as set forth in SEQ ID NO: 3 or SEQ ID NO: 4.

It will be understood that an immunogenic fragment may also comprise a polypeptide comprising both SEQ ID NO: 3 and/or 4 and homologs thereof.

In any embodiment of the invention, the composition may comprise one or more additional polypeptides for forming an immune response in a subject against a tick antigen. Examples of such additional polypeptides include the Bm86 polypeptide, or immunogenic fragments or variants thereof. The Bm86 amino acid sequence is set forth in SEQ ID NO: 5. Variants or fusion protein sequence derived from Bm86 and which may be included in the compositions herein described are set forth in SEQ ID NOs: 24 to 32.

In some embodiments, the polypeptides provided in the compositions described herein, may be conjugated to a carrier protein. The carrier protein may comprise or consist of at least one T-cell epitope. Examples of suitable carrier proteins include Keyhole Limpet Hemocyanin (KLH) carrier protein (as set forth in SEQ ID NO: 6) which beneficially contains multiple T-cell epitopes. Alternative carrier proteins that are suitable for use in the compositions of the present invention include, but are not limited to, *Concholepas concholepas* Hemocyanin (CCH) (as set forth in SEQ ID NO:s SEQ ID NO: 18 and 19, respectively), ovalbumin (as set forth in SEQ ID NO: 20), bovine serum albumin (as set forth in SEQ ID NO: 21), and cholera toxin B (as set forth in SEQ ID NO: 22).

In any embodiment of the invention, the polypeptide provided in the compositions described herein, further comprises a T-cell epitope, including one or more promiscuous T-cell helper epitopes. By way of an example, promiscuous T-cell helper epitopes that can be used with the present invention include those having an amino acid sequence selected from SEQ ID NO: 9, 10, 11, 12, and 13. Suitably, the polypeptide may be encoded by a nucleic acid molecule that also encodes a promiscuous T-cell helper epitope. In some embodiments, the compositions may include more than one (i.e., a plurality) of promiscuous T-cell helper epitopes, optionally conjugated or otherwise linked to one another.

In some embodiments, the compositions described herein further comprise an adjuvant for potentiating the immune response to the immunogen. For example, oil adjuvants (including water in oil (w/o) adjuvants and water in oil in water (w/o/w) adjuvants are particularly suitable for livestock immunization. By way of an example, Montanide® series and saponin are particularly suitable adjuvants for formulating with the compositions of the present invention. Other examples of suitable adjuvants include Freund's complete or incomplete adjuvant.

In still further embodiments, the compositions may further comprise a pharmaceutically acceptable carrier, excipient, or diluent.

Still further, the present invention contemplates the use of a nucleic acid construct for forming an immune response in a subject to a tick antigen,
the construct comprising, a polynucleotide encoding a polypeptide,
wherein the polypeptide comprises, consists or consists essentially of an amino acid sequence corresponding the M1-2A Clone 91 polypeptide as set forth in SEQ ID NO: 1, or immunogenic fragments or derivatives thereof; and
wherein the polynucleotide is operably linked to a regulatory element for enabling the expression of the polypeptide.

In any embodiment, the polypeptide encoded by the polynucleotide comprises, consists of or consists essentially of the amino acid sequence as set forth in SEQ ID NO: 1. Alternatively, the polypeptide encoded by the polynucleotide comprises, consists of or consists essentially of the amino acid sequence as set forth in SEQ ID NO: 3 or SEQ ID NO: 4.

In any embodiment, the polynucleotide provided in the polynucleotide compositions described herein comprises, consists of or consists essentially of the nucleotide sequence as set forth in SEQ ID NO: 2.

In some embodiments, the present invention provides a construct system for forming an immune response in a subject to a tick antigen, wherein the construct system comprises: a first nucleic acid construct comprising a first coding sequence that encodes a first polypeptide antigen comprising an amino acid sequence that corresponds to the M1-2A Clone 91 tick polypeptide; and a second nucleic acid construct comprising a second coding sequence that encodes second polypeptide antigen comprising an amino acid sequence that corresponds to the M1-2A Clone 91 tick polypeptide and that is operably connected to a third coding sequence that encodes a ubiquitin polypeptide; wherein the first nucleic acid construct and the second nucleic acid construct are operably linked to a common regulatory polynucleotide or to a different regulatory polynucleotide.

In some embodiments, the construct system further comprises a pharmaceutically acceptable carrier, excipient, or diluent. In some embodiments, the construct system also or instead comprises an adjuvant.

In another aspect, the present invention provides a method for forming an immune response in a subject to a tick antigen,
the method comprising administering to a subject in need, an effective amount of a composition as described herein.

More specifically, the present invention provides a method for forming an immune response in a subject to a tick, the method comprising administering to a subject in need:
an effective amount of a recombinant or synthetic polypeptide, wherein the polypeptide comprises, consists of or consists essentially of the sequence of the M1-2A Clone 91 tick polypeptide, as set forth in SEQ ID NO: 1,
an adjuvant for potentiating the immune response to the immunogen
thereby forming an immune response in the subject to a tick.

The polypeptide may comprise the entire amino acid sequence of SEQ ID NO:1, or variants or immunogenic homologs thereof. For example, the immunogen variant may be a polypeptide that comprises or consists of SEQ ID NO: 3, or SEQ ID NO: 4 or both SEQ ID NO: 3 and SEQ ID NO: 4. In further embodiments, the polypeptide may comprise SEQ ID NO: 1, 3 or 4 (or variants thereof) as well as a carrier protein. Preferably the carrier protein is Keyhole Limpet Hemocyanin (KLH), although the skilled person will appreciate that it is possible to use alternative carrier proteins. The polypeptide of SEQ ID NO: 1 and the carrier protein may be conjugated, for example using a linker peptide as further described herein.

In any embodiment, the immune response is one or both of a humoral immune response and a cellular immune response. For example, the immune response may be a $CD4^+$ immune response.

The present invention also provides a method of preventing, or reducing the severity of a tick infestation, or for reducing the risk of transmission of a tick infestation in a subject or population of animals, the method comprising administering to a subject in need:
an effective amount of a recombinant or synthetic polypeptide, wherein the polypeptide comprises, consists of or consists essentially of the sequence of the M1-2A Clone 91 tick polypeptide, as set forth in SEQ ID NO: 1,
an adjuvant for potentiating the immune response to the immunogen
thereby forming an immune response in the subject to a tick.

The subject may receive the immunogenic composition described above on a single occasion, or at least two, three or more occasions before being exposed to challenge (i.e., exposed to ticks).

In any embodiment of the invention described above, the compositions may be administered to the subject intradermally, subcutaneously, intravenously, or orally.

In any of the methods described above the subject is selected from the group consisting of: cattle, deer, antelope, sheep, buffalo, horses, rhinoceroses, peccaries, pigs, giraffes, okapi, pronghorn, ox, antelopes, camels, llamas, chevrotains, hippopotamuses, tapirs, zebras or a companion animal. Preferably the subject is cattle, preferably beef cattle or dairy cattle.

Alternatively, the present invention provides a method for forming an immune response in a subject to a tick antigen, the method comprising administering to a subject in need:
a nucleic acid construct encoding a polypeptide, wherein the polypeptide comprises, consists of or consists essentially of the sequence of the M1-2A Clone 91 tick polypeptide, as set forth in SEQ ID NO: 1,
wherein the polynucleotide is operably linked to a regulatory polynucleotide sequence for enabling the expression of the polypeptide
an adjuvant for potentiating the immune response to the polypeptide.
thereby forming an immune response in the subject to the tick polypeptide.

In some embodiments, the method elicits in the subject one or both of a humoral immune response and a cellular immune response. In some embodiments, the cellular immune response is a $CD4^+$ immune response. Preferably the immune response results in a reduction in the amount of tick infestation in the subject, or reduces the severity of tick infestation in the subject.

In yet another aspect, the present invention provides a method of treating a subject (e.g., livestock) with a tick infestation, the method comprising administering to the subject an effective amount of a composition as herein described. More particularly, the invention provides a method of treating a subject with a tick infestation, the method comprising administering to the subject:
an effective amount of a polypeptide, wherein the polypeptide comprises, consists of or consists essentially of the sequence of the M1-2A Clone 91 tick polypeptide, as set forth in SEQ ID NO: 1,
an adjuvant for potentiating the immune response to the polypeptide
thereby treating the tick infestation in the subject.

The compositions and methods described above are suitable for eliciting an immune response to a tick polypeptide antigen in any mammal that is prone to tick infestation (including mammals that are carriers of ticks). By way of an illustrative example, the methods of the present invention can be performed on an ungulate, for example any one of cattle, buffalo, deer, antelope, horses, sheep, donkeys, rhinoceroses, peccaries, pigs, giraffes, okapi, pronghorn, ox, antelopes, camels, llamas, chevrotains, hippopotamuses, tapirs and zebras. Suitably, the methods are performed on cattle, and more particularly beef cattle and/or dairy cattle. In other embodiments, the methods and compositions of the invention are useful for eliciting an immune response to a tick in a companion animal, including but not limited to dogs, cats, guinea pigs, mice, rats, and rabbits.

Any one of the compositions as described above and elsewhere here in can be used in the methods of the present invention.

The compositions and methods of the present invention have utility in treating or preventing tick infestations, or reducing the risk of transmission of a tick to a subject, or reducing the severity of tick infestation in a subject, wherein the tick is from the family Ixodidae. Non-limiting examples of ticks belonging to the Ixodidae family include *Rhipicephalus (boophilus) microplus, R. annulatus, R. australis, R. kohlsi, R. geigyi, R. appendiculatus, R. sanguineus* (brown dog tick), *R. bursa, Amblyomma variegatum* (tropical bont tick), *A. americanum* (lone star tick), *A. cajennense* (cayenne tick), *A. hebraeum* (African bont tick), *Boophilus decoloratus, Dermacentor reticulatus* (American levi tick), *D. andersoni* (Rocky Mountain wood tick), *D. marginazus* (ornate sheep tick), *D. variabilis* (American dog tick), *Haemaphysalis inermis, Ha. leachii, Ha. punctata, Hyalomma anatolicum anatolicum, Hy. dromedarii, Hy. marginaturn marginaturn, Ixodes ricinus* (castor bean tick), *I. persulcatus* (taiga tick), *I. scapularis* (commonly known as deer tick, blacklegged tick, and bear tick), and *I. hexagonus*. Preferably the tick is *Rhipicephalus microplus* (also commonly referred to as Asian blue tick, Australian cattle tick, southern cattle tick, cuban tick, Madagascar blue tick and Porto Rican Texas fever tick) which is a species complex including 3 clades to date, *R. australis* and *R. annulatus*.

In preferred embodiment of the invention, the use of the compositions and method result in a reduction in the total number of ticks infesting a subject (wherein NET is the ratio of the average total tick numbers vaccinated group/control group).

In further embodiments, the methods and compositions of the invention reduce the average weight of the eggs (in gram) per number of ticks (EW) that have fed or infested a subject.

Still further, the methods and compositions of the invention reduce the EC ration, being the ratio of the percent larval emergence from the eggs of ticks that have fed on a vaccinated subject.

In a preferred embodiment, the present invention provides a composition for preventing infestation with a tick, or treating or reducing the severity of a tick infestation in a subject, wherein the tick is from the species complex *R. microplus*, wherein the composition comprises:
a recombinant or synthetic polypeptide comprising the amino acid sequence of SEQ ID NO: 1, or an immunogenic fragment or derivative thereof (for example, a polypeptide comprising the amino acid sequence of SEQ ID NO: 3 and/or SEQ ID NO: 4); and
an adjuvant for potentiating an immune response to the polypeptide.

In a further preferred embodiment, the present invention provides a method for preventing infestation with a tick, or treating or reducing the severity of a tick infestation in a subject, wherein the tick is from the species complex *R. microplus*, wherein the method comprises:
administering to the subject, an effective amount of a recombinant or synthetic polypeptide comprising the amino acid sequence of SEQ ID NO: 1, or an immunogenic fragment or derivative thereof (for example, a polypeptide comprising the amino acid sequence of SEQ ID NO: 3 and/or SEQ ID NO: 4); and
an adjuvant for potentiating an immune response to the polypeptide;
thereby preventing infestation with a tick, or treating or reducing the severity of a tick infestation in the subject.

Preferably the subject is a mammalian subject, in particular livestock or a companion animal.

Preferably, the adjuvant is Freund's complete or incomplete adjuvant. Preferably the composition is administered to the subject on at least two or three or more occasions, to elicit an immune response to the subject. Preferably the subject is cattle.

In yet another aspect, the present invention provides a method of producing an antigen-binding molecule (e.g., an antibody, such as a neutralising antibody) that is immuno-interactive with a tick polypeptide, wherein the method comprises immunizing an animal with a tick polypeptide; and isolating an antigen-binding molecule produced by the immune system of the animal in response to the immunization.

In some embodiments the antigen-binding molecule is a derivative antigen-binding molecule produced by the methods of this aspect. By way of an example, the derivative antigen-binding molecule is selected from antibody fragments (such as Fab, Fab', F(ab')$_2$, Fv), single chain (scFv) and domain antibodies, and fusion proteins comprising an antibody, and any other modified configuration of the immunoglobulin molecule that comprises an antigen binding and/or recognition site.

In some embodiments, the antigen-binding molecule (or derivative antigen-binding molecules) produced by these methods are formulated into a composition, wherein the compositions also comprise a pharmaceutically acceptable carrier, diluent, or adjuvant.

BRIEF DESCRIPTION OF THE SEQUENCES

TABLE 1

| SEQUENCE ID NUMBER | SEQUENCE DESCRIPTION | LENGTH |
|---|---|---|
| SEQ ID NO: 1 | M1-2A Clone 91 polypeptide<br>MAPNAPAKPDAMWVFGYGSLMWKADFPYNRK<br>LVGYVKGYVRRFWQASEDHRGVPGKPGRVVT<br>LVPSTDQNDCVWGVAYEIPEGEKDDVIGRLDFR<br>EKDGYDRVQVTFYPGKSEEKPFPLTIYVAQKEN<br>PFYLGPANALDIARQIRSAEGPSGSNREYLLSLI<br>ECMRNIAPHVPRPALDGNRAKPA | 185 aa |
| SEQ ID NO: 2 | M1-2A Clone 91 polynucleotide | 946 nt |
| SEQ ID NO: 3 | M1-2A Clone 91 immunogenic peptide<br>RSAEGPSGSNR | 11 aa |
| SEQ ID NO: 4 | M1-2A Clone 91 immunogenic peptide<br>PHVPRPALDGNRAKPA | 16 aa |
| SEQ ID NO: 5 | Bm86 polypeptide sequence from *R. microplus* | 660 aa |
| SEQ ID NO: 6 | Keyhole Limpet Hemocyanin 1 polypeptide | 3408 aa |
| SEQ ID NO: 7 | Bovine ubiquitin polypeptide (UniProtKB Acc. No. P63048) | 128 aa |
| SEQ ID NO: 8 | Bovine ubiquitin nucleic acid sequence | 228 nt |
| SEQ ID NO: 9 | Measles virus protein F peptide (residues 289-302) | 15 aa |
| SEQ ID NO: 10 | Native tetanus toxin (UniProtKB Acc. No. P04958) | 1315 aa |
| SEQ ID NO: 11 | Tetanus toxin peptide (residues 583-599) | 18 aa |
| SEQ ID NO: 12 | Tetanus toxin peptide (residues 830-844) | 15 aa |
| SEQ ID NO: 13 | Tetanus toxin peptide (residues 947-957) | 21 aa |
| SEQ ID NO: 14 | *Anaplasma marginale* polypeptide | 11 aa |
| SEQ ID NO: 15 | *Plasmodium falciparum* CSP protein | 20 aa |
| SEQ ID NO: 16 | Influenza HA B epitope | 18 aa |
| SEQ ID NO: 17 | PADRE | 12 aa |
| SEQ ID NO: 18 | Concholepas concholepas hemocyanin subunit A (UniProtKB accession No. P84619) | 11 aa |
| SEQ ID NO: 19 | Concholepas concholepas hemocyanin subunit B (UniProtKB accession No. P84620) | 7 aa |
| SEQ ID NO: 20 | Chicken Ovalbumin (UniProtKB accession No. P01012) | 386 aa |
| SEQ ID NO: 21 | Bovine serum albumin (UniProtKB accession no. P02769) | 607 aa |

TABLE 1-continued

| SEQUENCE ID NUMBER | SEQUENCE DESCRIPTION | LENGTH |
|---|---|---|
| SEQ ID NO: 22 | Cholera toxin B polypeptide (UniProt accession no. P01556) | 124 aa |
| SEQ ID NO: 23 | CMV CTL peptide epitope pp65$_{495-503}$ | 7 aa |
| SEQ ID NO: 24 | Peptide fragment of Bm86 polypeptide | 14 aa |
| SEQ ID NO: 25 | Peptide fragment of Bm86 polypeptide | 7 aa |
| SEQ ID NO: 26 | Peptide fragment of Bm86 polypeptide | 8 aa |
| SEQ ID NO: 27 | Peptide fragment of Bm86 polypeptide | 10 aa |
| SEQ ID NO: 28 | Peptide fragment of Bm86 polypeptide | 8 aa |
| SEQ ID NO: 29 | Peptide fragment of Bm86 polypeptide | 7 aa |
| SEQ ID NO: 30 | Bm86 fusion protein sequence SBm4912 | 45 aa |
| SEQ ID NO: 31 | Bm86 fusion protein sequence SBm7462 | 45 aa |
| SEQ ID NO: 32 | Bm86 fusion protein sequence SBm19733 | 51 aa |

DETAILED DESCRIPTION OF THE EMBODIMENTS

1. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

The terms "antigen" and "epitope" are well understood in the art and refer to the portion of a macromolecule which is specifically recognized by a component of the immune system, e.g., an antibody or a T-cell antigen receptor. Epitopes are recognized by antibodies in solution, e.g., free from other molecules. Epitopes are also recognized by T-cell antigen receptor that is present on the cell surface of a CD4$^+$ T helper cell when the epitope is associated with a class II major histocompatibility complex (MHC) molecule.

By "antigen-binding molecule" is meant a molecule that has binding affinity for a tick polypeptide. It will be understood that this term extends to immunoglobulins, immunoglobulin fragments and non-immunoglobulin derived protein frameworks that exhibit antigen-binding activity.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

By "corresponds to" or "corresponding to" is meant a polynucleotide (a) having a nucleotide sequence that is substantially identical or complementary to all or a portion of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

By "effective amount," in the context of modulating an immune response or treating or preventing a disease or condition, is meant the administration of that amount of composition to an individual in need thereof, either in a single dose or as part of a series, that is effective for achieving that modulation, treatment or prevention. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

It will be understood that "eliciting", "stimulating" or "inducing" an immune response as contemplated herein includes stimulating a new immune response and/or enhancing a previously existing immune response.

As used herein, the terms "encode," "encoding" and the like refer to the capacity of a nucleic acid to provide for another nucleic acid or a polypeptide. For example, a nucleic acid sequence is said to "encode" a polypeptide if it can be transcribed and/or translated to produce the polypeptide or if it can be processed into a form that can be transcribed and/or translated to produce the polypeptide. Such a nucleic acid sequence may include a coding sequence or both a coding sequence and a non-coding sequence. Thus, the terms "encode," "encoding" and the like include an RNA product resulting from transcription of a DNA molecule, a protein resulting from translation of an RNA molecule, a protein resulting from transcription of a DNA molecule to form an RNA product and the subsequent translation of the RNA product, or a protein resulting from transcription of a DNA molecule to provide an RNA product, processing of the RNA product to provide a processed RNA product (e.g., mRNA) and the subsequent translation of the processed RNA product.

The term "expression" with respect to a gene sequence refers to transcription of the gene and, as appropriate, translation of the resulting mRNA transcript to a protein. Thus, as will be clear from the context, expression of a coding sequence results from transcription and translation of the coding sequence. Conversely, expression of a non-coding sequence results from the transcription of the non-coding sequence.

By "expression vector" is meant any autonomous genetic element capable of directing the synthesis of a protein encoded by the vector. Such expression vectors are known by practitioners in the art.

"Immune response" or "immunological response" refers to the concerted action of any one or more of lymphocytes, antigen-presenting cells, phagocytic cells, granulocytes, and soluble macromolecules produced by the above cells or the liver (including antibodies, cytokines, and complement) that results in selective damage to, destruction of, or elimination from the body of invading pathogens, cells or tissues infected with pathogens. In some embodiments, an "immune response" encompasses the development in an individual of a humoral and/or a cellular immune response to a polypeptide that is encoded by an introduced synthetic coding sequence of the invention. A "humoral immune response" includes and encompasses an immune response mediated by antibody molecules, while a "cellular immune response" includes and encompasses an immune response mediated by T-lymphocytes and/or other white blood cells. Hence, an immunological response may include one or more of the following effects: the production of antibodies by B-cells; and/or memory/effector T-cells directed specifically to an antigen or antigens present in the composition or vaccine of interest. In some embodiments, these responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art (see, e.g., Montefiori et al., 1988, *J Clin Microbiol.* 26:231-235; Lew-Tabor et al., 2014, *Ticks Tick Borne Dis,* 5(5): 500-10; and Rodriguez-Mallon, 2016, *Methods Mol Biol,* 1404: 243-59). The innate immune system of mammals also recognizes and responds to molecular features of pathogenic organisms and cancer cells via activation of Toll-like receptors and similar receptor molecules on immune cells. Upon activation of the innate immune system, various non-adaptive immune response cells are activated to, e.g., produce various cytokines, lymphokines and chemokines. Cells activated by an innate immune response include immature and mature dendritic cells of, for example, the monocyte and plasmacytoid lineage (MDC, PDC), as well as gamma, delta, alpha and beta T-cells and B-cells and the like. Thus, the present invention also contemplates an immune response wherein the immune response involves both an innate and adaptive response.

Reference herein to "immuno-interactive" includes reference to any interaction, reaction, or other form of association between molecules and in particular where one of the molecules is, or mimics, a component of the immune system.

A composition is "immunogenic" if it is capable of either: a) generating an immune response (e.g., a $CD4^+$ immune response) against an a tick polypeptide in an individual; or b) reconstituting, boosting, or maintaining an immune response (e.g., a $CD4^+$ immune response) in an individual beyond what would occur if the agent or composition was not administered. An agent or composition is immunogenic if it is capable of attaining either of these criteria when administered in single or multiple doses. The immune response may include a cellular immune response and/or humoral immune response in a subject.

Throughout this specification, unless the context requires otherwise, the words "include," "includes" and "including" will be understood to imply the inclusion of a stated step or element or group of steps or elements but not the exclusion of any other step or element or group of steps or elements.

By "infestation" is meant to refer to a bite of one or more than one tick. An infestation can be the presence and attachment of a tick to a subject or, in certain embodiments, can refer to a subject coming in contact with a tick, but the tick does not remain attached. An infestation may or may not result in a condition or disorder that is directly or indirectly (e.g., through a hosting pathogenic organism) caused by a tick (e.g., bovine tick fever caused by *Babesia* and/or *Anaplasma*).

The term "gene" as used herein refers to any and all discrete coding regions of a genome, as well as associated non-coding and regulatory regions. The gene is also intended to mean an open reading frame encoding one or more specific polypeptides, and optionally comprising one or more introns, and adjacent 5' and 3' non-coding nucleotide sequences involved in the regulation of expression. In this regard, the gene may further comprise regulatory nucleic acids such as promoters, enhancers, termination and/or polyadenylation signals that are naturally associated with a given gene, or heterologous control signals. Genes may or may not be capable of being used to produce a functional protein. Genes can include both coding and non-coding regions.

By "linker" is meant a molecule or group of molecules (such as a monomer or polymer) that connects two molecules and often serves to place the two molecules in a desirable configuration.

As used herein, the term "mammal" refers to any mammal including, without limitation, cattle and other ungulates. The term also includes companion animals such as dogs, cats, guinea pigs, rabbits, mice and rats. The term does not denote a particular age. Thus, both adult and newborn individuals are intended to be covered. The term does not denote a particular age. Thus, both adult and newborn individuals are intended to be covered.

The terms "operably connected," "operably linked" and the like as used herein refer to an arrangement of elements wherein the components so described are configured so as to perform their usual function. Thus, a given regulatory nucleic acid such as a promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence. Terms such as "operably connected," therefore, include placing a structural gene under the regulatory control of a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e. the gene from which the genetic sequence or promoter is derived. As is known in the art, some variation in this distance can be accommodated without loss of function. Similarly, the preferred positioning of a promoter with respect to a heterologous gene to be placed under its control is defined by the positioning of the promoter in its natural setting; i.e., the genes from which it is derived. Alternatively, "operably connecting" a gD2 coding sequence to a nucleic acid sequence that encodes a protein-destabilizing element (PDE) encompasses positioning and/or orientation of the gD2 coding sequence relative to the PDE-encoding nucleic acid sequence so that (1) the coding sequence and the PDE-encoding nucleic acid sequence are transcribed together to form a single chimeric transcript and (2) the gD2 coding sequence is 'in-frame' with the PDE-encoding nucleic acid sequence to produce a chimeric open reading frame comprising the gD2 coding sequence and the PDE-encoding nucleic acid sequence.

By "pharmaceutically-acceptable carrier" is meant a solid or liquid filler, diluent or encapsulating substance that may be safely used in topical or systemic administration.

The term "polynucleotide" or "nucleic acid" as used herein designates mRNA, RNA, cRNA, cDNA or DNA. The term typically refers to oligonucleotides greater than 30 nucleotides in length.

Polypeptide," "peptide" and "protein" are used interchangeably herein to refer to a polymer of amino acid residues and to variants and synthetic analogues of the same. As used herein, the terms "polypeptide," "peptide" and "protein" are not limited to a minimum length of the product. Thus, peptides, oligopeptides, dimers, multimers, and the like, are included within the definition. Both full-length proteins and portions thereof are encompassed by the definition. The terms "biologically active portions" or "fragments" are used interchangeably herein, to describe an immunogenic portion of a tick polypeptide. These portions can be a polypeptide which is, for example, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or more amino acid residues in length. Suitably, the portion or fragment has no less than about 1%, 10%, 25%, or 50% of an activity of the full-length polypeptide from which it is derived.

The terms "prime immunization", "priming immunization" and the like refer to primary antigen stimulation by using an immunostimulatory composition according to the present invention. The animal that receives the priming immunization may or may not have already been exposed to the tick polypeptide(s) against which the prime immunization is designed, for instance, by prior infestation.

The terms "boost immunization", "boosting immunization", "booster immunization" and the like refer to additional immunization administered to or effective in a mammal after the primary immunization. In various embodiments, the boost immunization is administered at a dose higher than, lower than, or equal to the effective dose that is normally administered when the boost immunization is administered alone without priming. In certain advantageous embodiments, the boost immunization is administered to an animal at a lower dose then the effective dose that would be used when the immunization is administered to the mammal alone without priming.

By "promiscuous T-cell epitope" is meant a highly immunogenic peptide that can be characterized in part by their capacity to bind several isotypic and allotypic forms of MHC class II molecules. By helping to bypass MHC restriction, they can induce T-cell and antibody responses in members of a genetically diverse population expressing diverse MHC haplotypes. The promiscuous T-cell epitopes can therefore be combined with antigens that, by themselves, are poorly immunogenic, to generate potent peptide immunogens. In some embodiments, the T-cell epitope comprises a heterologous CD4 T cell epitope to enhance the immunogenicity of the immunostimulatory compositions.

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter gene expression in response to developmental and/or environmental stimuli, or in a tissue-specific or cell-type-specific manner.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, 5 T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to 10 yield the percentage of sequence identity. For the purposes of the present invention, "sequence identity" will be understood to mean the "match percentage" calculated by the DNASIS computer program (Version 2.5 for Windows; available from Hitachi Software engineering Co., Ltd., South San Francisco, Calif., USA) using standard defaults as used in the reference manual accompanying the software.

"Similarity" refers to the percentage number of amino acids that are identical or constitute conservative substitutions as defined in Table 3. Similarity may be determined using sequence comparison programs such as GAP (Deveraux et al. 1984, Nucleic Acids Research 12, 387-395). In this way, sequences of a similar or substantially different length to those cited herein might be compared by insertion of gaps into the alignment, such gaps being determined, for example, by the comparison algorithm used by GAP.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, Nucleic Acids Res. 25:3389. A detailed discussion of sequence analysis can be found in Unit 19.3 of Ausubel et al., "Current Protocols in Molecular Biology", John Wiley & Sons Inc, 1994-1998, Chapter 15.

By "subject" is meant any animal that is susceptible to infestation by a tick. A subject can include, but is not limited to vertebrates, including mammals such as livestock animals, including cattle, sheep, goats, pigs, horses chickens, turkeys, ostriches, ducks, and geese; pets (companion animals), such as cats, dogs, and horses; and animals that might be held in a zoo. "Ungulates" are members of a diverse group of primarily hoofed mammals that include odd-toed ungulates such as horses and rhinoceroses, and even-toes ungulates, such as cattle, pigs, giraffes, camels, deer, and hippopotamuses.

By "tick" is meant to refer to organisms belonging to the superfamily Ixodoidea. Ticks according to the invention can be at any developmental stage (e.g. larvae, nymphs, or adults).

By "treat," "treating," "treatment," and the like are meant to refer to reducing or ameliorating a disorder and/or symptoms associated therewith. It will be appreciated that, although not precluded, treating a disorder or condition does not require that the disorder, condition or symptoms associated therewith be completely eliminated.

The term "ubiquitin molecule" refers to a member of the protein superfamily of ubiquitin and ubiquitin-like proteins, which when conjugated to a target protein results in the introduction of that target protein into the cellular degradation machinery, including the proteasome.

By "vector" is meant a nucleic acid molecule, preferably a DNA molecule derived, for example, from a plasmid, bacteriophage, or plant virus, into which a nucleic acid sequence may be inserted or cloned. A vector preferably contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector may also include a selection marker such as an antibiotic resistance gene that can be used for selection of suitable transformants. Examples of such resistance genes are well known to those of skill in the art.

The term "wild-type", with respect to an organism, polypeptide, or nucleic acid sequence, refers to an organism, polypeptide or nucleic acid sequence that is naturally occurring or available in at least one naturally occurring organism which is not changed, mutated, or otherwise manipulated by man.

2. Immunogenic Compositions

The present invention is based in part on the determination that M1-2A Clone 91 polypeptide from *Rhipicephalus microplus* is capable of stimulating or eliciting an immune response in a subject to a tick. The present inventors have determined that when this polypeptide, or peptides derived therefrom are administered to animals (e.g., cattle) they are surprisingly effective as a preventative and therapeutic treatment for tick infestations. In doing so, compositions that comprise the polypeptide are also effective at reducing diseases that are transmitted by ticks. The present invention provides compositions comprising at least one polypeptide antigen with an amino acid sequence that corresponds to tick polypeptides in compositions and methods for treating or preventing tick infestations in a subject.

2.1 M1-2A Clone 91 Tick Polypeptides

The polypeptide antigens suitable for use in the compositions of the present invention correspond to at least one immunogenic epitope of the M1-2A Clone 91 tick polypeptide. In some embodiments, the immunogenic epitope is present in one or more orthologous tick polypeptides (i.e., conserved in a tick species other than the species in which the tick polypeptide was identified or derived).

In some preferred embodiments, the tick polypeptides are obtained or derived from a tick of the Ixodidae family. Non-limiting examples of ticks belonging to the Ixodidae family include *Rhipicephalus (Boophilus) microplus, R. annulatus, R. australis, R. kohlsi, R. geigyi, R. appendiculatus, R. sanguineus* (brown dog tick), *R. bursa, Amblyomma variegatum* (tropical bont tick), *A. americanum* (lone star tick), *A. cajennense* (cayenne tick), *A. hebraeum* (African bont tick), *Boophilus decoloratus, Dermacentor reticulatus* (American levi tick), *D. andersoni* (Rocky Mountain wood tick), *D. marginazus* (ornate sheep tick), *D. variabilis*

(American dog tick), *Haemaphysalis inermis, Ha. leachii, Ha. punctata, Hyalomma anatolicum anatolicum, Hy. dromedarii, Hy. marginatum marginatum, Ixodes ricinus* (castor bean tick), *I. persulcatus* (taiga tick), *I. scapularis* (commonly known as deer tick, blacklegged tick, and bear tick), and *I. hexagonus*. Notably, the *R. microplus* species complex has been designated into at least five taxa, including *R. microplus* clade A, *R. microplus* clade B, *R. microplus* clade C, *R. australis* and *R. annulatus* (see, Burger et al, 2014; and Low et al., 2015).

In view of their substantial structural and sequence similarity, tick polypeptide orthologues are generally considered to have the same or similar levels of immunogenicity as one another. The present inventors thus consider that conserved tick polypeptides obtained from any tick species will be useful in eliciting an immune response in animals for treating or preventing a tick infestation.

In some embodiments, the at least one polypeptide antigen corresponds to at least a portion of the M1-2A Clone 91 tick polypeptide derived from *R. australis*. The tick polypeptide M1-2A Clone 91 is predicted to be a transporter protein, with the full-length native amino acid sequence is as follows:

[SEQ ID NO: 1]
MAPNAPAKPDAMWVFGYGSLMWKADFPYNRKLVGYVKGYVRRFWQASEDHR

GVPGKPGRVVTLVPSTDQNDCVWGVAYEIPEGEKDDVIGRLDFREKDGYDR

VQVTFYPGKSEEKPFPLTIYVAQKENPFYLGPANALDIARQIRSAEGPSGS

NREYLLSLIECMRNIAPHVPRPALDGNRAKPA.

The present invention contemplates the full-length M1-2A Clone 91 tick polypeptide as well as its biologically (e.g., immunologically) active fragments. Typically, biologically active portions of a full-length tick polypeptide may participate in an interaction, for example, an intra-molecular or an inter-molecular interaction and/or are capable of stimulating an immune response to the tick polypeptide. Such biologically active portions include peptides comprising amino acid sequences sufficiently similar to or derived from the amino acid sequences of a (putative) full-length tick polypeptide, for example, the amino acid sequences set forth in any one of SEQ ID NO: 3 and 4, which include less amino acids than a the full-length tick polypeptide from which they are derived, and retain the ability to elicit an immune response (e.g., a cellular immune response and/or a humoral immune response) to the native tick polypeptide. Typically, biologically active fragments will comprise a domain, sequence or motif with at least one activity (i.e., an immunostimulatory activity) of a putatively full-length tick polypeptide.

By way of an illustrative example, the polypeptide antigen may correspond to a portion of the full-length native M1-2A Clone 91 amino acid sequence set forth in SEQ ID NO: 1. Suitable fragments of this type may comprise, consist, or consist essentially of one or both of the amino acid sequences RSAEGPSGSNR (SEQ ID NO: 3) (corresponding to residues 145-155 of SEQ ID NO: 1) and PHVPRPALDGNRAKPA (SEQ ID NO: 4) (corresponding to residues 170-185 of SEQ ID NO: 1). These tick polypeptide sequences are predicted to be B-cell epitopes, and are therefore particularly suitable for generating effective antibodies against the native M1-2A Clone 91 tick polypeptide.

In other illustrative embodiments, the polypeptide antigen may be derived from a functional orthologue of the native M1-2A Clone 91 tick polypeptide originally identified in *R. australis*. By way of a illustrative example, the tick polypeptide can be a functional orthologue of M1-2A Clone 91 as derived from any one of *R. microplus* clades, *R. annulatus*, *R. microplus*, etc.

2.2 Variants of Tick Polypeptides

The polypeptide antigens of the present invention include tick polypeptides (and fragments thereof) which arise as a result of the existence of alternative translational and post-translational events.

In some embodiments the polypeptide antigen may comprise an amino acid sequence that shares at least 50% (and at least 51% to at least 99% and all integer percentages in between) sequence similarity or sequence identity with the M1-2A Clone 91 tick polypeptide sequence as set forth in any one of SEQ ID NO: 1 or a fragment of such polypeptides. In more specific embodiments, the polypeptide antigen may comprise an amino acid sequence that shares at least 75%, 80%, 85%, 90%, 91%, 92%, 93%, 94%, 95%, 96%, 97%, 98% or 99% sequence similarity or sequence identity with the M1-2A Clone 91 tick polypeptide.

The present invention also contemplates tick polypeptides that are variants of wild-type or naturally-occurring M1-2A Clone 91 tick polypeptide or their biologically active fragments. Such "variant" peptides or polypeptides include proteins derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Non-limiting examples of such variant tick polypeptides include processed forms of a full-length or precursor M1-2A Clone 91 tick polypeptide, including but not limited to peptides or polypeptides in which the signal peptide domain and/or any pro-regions are removed from the precursor form.

Variant proteins encompassed by the present invention are biologically (e.g., immunologically) active, that is, they continue to possess the desired biological activity of the native protein. Such variants may result from, for example, genetic polymorphism or from human manipulation.

A M1-2A Clone 91 tick polypeptide sequence may be altered in various ways including amino acid substitutions, deletions, truncations, and insertions. Methods for such manipulations are generally known in the art. For example, amino acid sequence variants of tick polypeptides can be prepared by mutations in the DNA. Methods for mutagenesis and nucleotide sequence alterations are well known in the art. See, for example, Kunkel (1985, *Proc. Natl. Acad. Sci. USA*. 82: 488-492), Kunkel et al., (1987, *Methods in Enzymol*, 154: 367-382), U.S. Pat. No. 4,873,192, Watson, J. D. et al., ("Molecular Biology of the Gene", Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. *Biomed. Res.* Found.).

Variant tick polypeptides may contain conservative amino acid substitutions at various locations along their sequence, as compared to a parent (e.g., naturally-occurring or reference) tick amino acid sequence. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

Dependent on their structural properties, amino acid residues may fall in two or more classes. For the naturally-occurring protein amino acids, sub-classification according to this scheme is presented in Table 2.

TABLE 2

Amino acid sub-classification

| SUB-CLASSES | AMINO ACIDS |
| --- | --- |
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Nonpolar/neutral | Alanine, Glycine, Isoleucine, Leucine, Methionine, Phenylalanine, Proline, Tryptophan, Valine |
| Polar/neutral | Asparagine, Histidine, Glutamine, Cysteine, Serine, Threonine, Tyrosine |
| Polar/negative | Aspartic acid, Glutamic acid |
| Polar/positive | Lysine, Arginine |
| Polar/large | Asparagine, Glutamine |
| Polar | Arginine, Asparagine, Aspartic acid, Cysteine, Glutamic acid, Glutamine, Histidine, Lysine, Serine, Threonine, Tyrosine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional tick polypeptide can readily be determined by assaying its activity. Conservative substitutions are shown in Table 3 under the heading of exemplary and preferred substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity.

TABLE 3

Exemplary and Preferred Amino Acid Substitutions

| Original Residue | Exemplary Substitutions | Preferred Substitutions |
| --- | --- | --- |
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., *Biochemistry*, third edition, William C. Brown Publishers (1993).

Thus, a predicted non-essential amino acid residue in a tick polypeptide is typically replaced with another amino acid residue from the same side chain family. Alternatively, mutations can be introduced randomly along all or part of a tick polypeptide gene coding sequence, such as by saturation mutagenesis, and the resultant mutants can be screened for an activity of the parent polypeptide, as described for example herein, to identify mutants which retain that activity. Following mutagenesis of the coding sequences, the encoded peptide or polypeptide can be expressed recombinantly and its activity determined. A "non-essential" amino acid residue is a residue that can be altered from the wild-type sequence of an embodiment peptide or polypeptide without abolishing or substantially altering one or more of its activities. Suitably, the alteration does not substantially alter one of these activities, for example, the activity is at least 20%, 40%, 60%, 70% or 80% of wild-type. By contrast, an "essential" amino acid residue is a residue that, when altered from the wild-type sequence of a "reference" M1-2A Clone 91 tick polypeptide, results in abolition of an activity of the parent molecule such that less than 20% of the wild-type activity is present. For example, such essential amino acid residues include those that are conserved in tick polypeptides across different species.

Accordingly, the present invention also contemplates as tick polypeptides, variants of the naturally-occurring tick polypeptide sequences or their biologically-active fragments, wherein the variants are distinguished from the naturally-occurring sequence by the addition, deletion, or substitution of one or more amino acid residues. In general, variants will display at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% similarity to a M1-2A Clone 91 tick polypeptide sequence as, for example, set forth in SEQ ID NO: 1, as determined by sequence alignment programs described elsewhere herein using default parameters. Desirably, variants will have at least 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to a M1-2A Clone 91 tick polypeptide sequence as, for example, set forth in SEQ ID NO: 1, as determined by sequence alignment programs described elsewhere herein using default parameters. Variants of a wild-type tick polypeptide, which fall within the scope of a variant polypeptide, may differ from the wild-type molecule generally by as much as 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, or 11 amino acid residues or suitably by as few as 10, 9, 8, 7, 6, 5, 4, 3, 2, or 1 amino acid residue(s). In some embodiments, a variant polypeptide differs from the corresponding sequences in SEQ ID NO: 1, 3, or 4 by at least 1 but by less than or equal to 25, 24, 23, 22, 21, 20, 19, 18, 17, 16, 15, 14, 13, 12, 11, 10, 9, 8, 7, 6, 5, 4, 3, or 2 amino acid residues. In other embodiments, it differs from the corresponding sequence in any one of SEQ ID NO: 1, 3, 5, 7, 9, or 11, by at least one 1% but less than or equal to 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3% or 2% of the residues. If the sequence comparison requires alignment, the sequences are typically aligned for maximum similarity or identity. "Looped" out sequences from deletions or insertions, or mismatches, are generally considered differences. The differences are, suitably, differences or changes at a non-essential residue or a conservative substitution, as discussed in more detail below.

The polypeptide antigens of the present invention also encompass tick polypeptides comprising amino acids with modified side chains, incorporation of unnatural amino acid residues and/or their derivatives during peptide, polypeptide or protein synthesis and the use of cross-linkers and other methods which impose conformational constraints on the peptides, portions and variants of the invention. Examples of side chain modifications include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with $NaBH_4$; reductive alkylation by reaction with an aldehyde followed by reduction with $NaBH_4$; and trinitrobenzylation of amino groups with 2, 4, 6-trinitrobenzene sulphonic acid (TNBS).

The carboxyl group may be modified by carbodiimide activation via O-acylisourea formation followed by subsequent derivatization, by way of example, to a corresponding amide.

The guanidine group of arginine residues may be modified by formation of heterocyclic condensation products with reagents such as 2,3-butanedione, phenylglyoxal and glyoxal.

Sulphydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulphides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulphonyl halides or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

Examples of incorporating unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids. A list of unnatural amino acids contemplated by the present invention is shown in Table 4.

TABLE 4

| Non-Conventional Amino acids | |
|---|---|
| Non-Conventional Amino Acids | |
| α-aminobutyric acid | L-N-methylalanine |
| α-amino-α-methylbutyrate | L-N-methylarginine |
| aminocyclopropane-carboxylate | L-N-methylasparagine |
| aminoisobutyric acid | L-N-methylaspartic acid |
| aminonorbornyl-carboxylate | L-N-methylcysteine |
| Cyclohexylalanine | L-N-methylglutamine |
| Cyclopentylalanine | L-N-methylglutamic acid |
| L-N-methylisoleucine | L-N-methylhistidine |
| D-alanine | L-N-methylleucine |
| D-arginine | L-N-methyllysine |
| D-aspartic acid | L-N-methylmethionine |
| D-cysteine | L-N-methylnorleucine |
| D-glutamate | L-N-methylnorvaline |

TABLE 4-continued

Non-Conventional Amino acids
Non-Conventional Amino Acids

| | |
|---|---|
| D-glutamic acid | L-N-methylornithine |
| D-histidine | L-N-methylphenylalanine |
| D-isoleucine | L-N-methylproline |
| D-leucine | L-N-medlylserine |
| D-lysine | L-N-methylthreonine |
| D-methionine | L-N-methyltryptophan |
| D-ornithine | L-N-methyltyrosine |
| D-phenylalanine | L-N-methylvaline |
| D-proline | L-N-methylethylglycine |
| D-serine | L-N-methyl-t-butylglycine |
| D-threonine | L-norleucine |
| D-tryptophan | L-norvaline |
| D-tyrosine | α-methyl-aminoisobutyrate |
| D-valine | α-methyl-γ-aminobutyrate |
| D-α-methylalanine | α-methylcyclohexylalanine |
| D-α-methylarginine | α-methylcylcopentylalanine |
| D-α-methylasparagine | α-methyl-α-napthylalanine |
| D-α-methylaspartate | α-methylpenicillamine |
| D-α-methylcysteine | N-(4-aminobutyl)glycine |
| D-α-methylglutamine | N-(2-aminoethyl)glycine |
| D-α-methylhistidine | N-(3-aminopropyl)glycine |
| D-α-methylisoleucine | N-amino-α-methylbutyrate |
| D-α-methylleucine | α-napthylalanine |
| D-α-methyllysine | N-benzylglycine |
| D-α-methylmethionine | N-(2-carbamylediyl)glycine |
| D-α-methylornithiine | N-(carbamylmethyl)glycine |
| D-α-methylphenylalanine | N-(2-carboxyethyl)glycine |
| D-α-methylproline | N-(carboxymethyl)glycine |
| D-α-methylserine | N-cyclobutylglycine |
| D-α-methylthreonine | N-cycloheptylglycine |
| D-α-methyltryptophan | N-cyclohexylglycine |
| D-α-methyltyrosine | N-cyclodecylglycine |
| L-α-methylleucine | L-α-methyllysine |
| L-α-methylmethionine | L-α-methylnorleucine |
| L-α-methylnorvatine | L-α-methylornithine |
| L-α-methylphenylalanine | L-α-methylproline |
| L-α-methylserine | L-α-methylthreonine |
| L-α-methyltryptophan | L-α-methyltyrosine |
| L-α-methylvaline | L-N-methylhomophenylalanine |
| N-(N-(2,2-diphenylethyl carbamylmethyl)glycine | N-(N-(3,3-diphenylpropyl carbamylmethyl)glycine |
| 1-carboxy-1-(2,2-diphenyl-ethyl amino)cyclopropane | |

The polypeptide antigens of the present invention also include peptides and polypeptides that are encoded by polynucleotides that hybridize under stringency conditions as defined herein, especially medium or high stringency conditions, to tick polypeptide-encoding polynucleotide sequences, or the non-coding strand thereof, as described below. Illustrative tick polynucleotide sequences are set forth in SEQ ID NO: 2 or their complements.

The skilled person will be familiar with methods for determining the percentage sequence identity between two amino acid or nucleic acid sequences.

Variants of a native tick polypeptide can be identified by screening combinatorial libraries of mutants, e.g., truncation mutants, of a tick polypeptide. Libraries or fragments e.g., N terminal, C terminal, or internal fragments, of a tick polypeptide coding sequence can be used to generate a variegated population of fragments for screening and subsequent selection of variants of a reference tick polypeptide.

Methods for screening gene products of combinatorial libraries made by point mutation or truncation, and for screening cDNA libraries for gene products having a selected property are known in the art. Such methods are adaptable for rapid screening of the gene libraries generated by combinatorial mutagenesis of tick polypeptides.

The polypeptide antigens of the present invention may be prepared by any suitable procedure known to those of skill in the art. For example, the polypeptide antigens may be produced by any convenient method such as by purifying the peptides or polypeptides from naturally-occurring reservoirs including ticks. Methods of purification include size exclusion, affinity or ion exchange chromatography/separation. The identity and purity of derived polypeptide antigen is determined for example by SDS-polyacrylamide electrophoresis or chromatographically such as by high performance liquid chromatography (HPLC). Alternatively, the polypeptide antigens may be synthesized by chemical synthesis (e.g., using solution synthesis or solid phase synthesis as described, for example, in Chapter 9 of Atherton and Shephard (supra) and in Roberge et al., (1995, *Science,* 269: 202)).

2.3 Tick Polypeptide Combinations

The compositions of the inventions may also comprise one or more further polypeptide antigens. For example, in some embodiments the composition includes a further polypeptide that corresponds to a tick polypeptide sequence, and wherein the polypeptide is capable of forming an immune response in a subject, when administered to the subject, so that the subject has a reduced risk of, or is treated for tick infestation.

For example, the further polypeptide antigen may comprise the Bm86 tick polypeptide antigens as described in International Patent Publication Nos. WO1988/003929 (identified as WGL+) and WO1995/004827 (the contents of which are incorporated herein in their entirety).

Therefore, in some embodiments, the compositions described herein comprise a further polypeptide antigen that corresponds to at least a portion of a Bm86 tick polypeptide, or a portion thereof. By way of an illustration, the polypeptide antigen may comprise, consist, or consist essentially of the full length native Bm86 polypeptide sequence from *R. microplus*, with the amino acid sequence:

[SEQ ID NO: 5]
MAARSGSSAADRFVAVALLATALYATAAADNFDTYLATLSNVSALIKDEAM

GVAFIEGLNDPYTTINNVDSSSSWDYASNITDYNQNMSNKVSTEVSKMERQ

FGITAKRFDWHNFKNDSLKRLFRHVATIGLAALPDDKLENATSLSSKMAAI

YGSTKVTVGKDKDLPLEPDLTRNMKEVGNYDKLLQTWLAWHNAVGPAIKQY

YIPYIKLSNEAASLDGYDNIKSAWLSDYETENMTEIVDKLWEDLSPLYKKL

HAYVRMKLREIYPGRLPEDGTIPAHLLGNMWAQEWGTLYPHLTMEDKPLDI

SKTMVEQKWDAQKMFHAAEDFFTSLGLDNMTSEFWSKSILTKPEDREIQCH

ASAWNMYNGDDFRIKMCTDPSVEELRTVHHEMGHIEYYMQYKHLHVLLQEG

ANEGFHEAVGDLIALSVATKTHYGKLSLLKPTDKYNAVDLLLMSALDKIAF

LPFGYLLDKWRWTIFTGETPFDKMNEKFWEYRIKYQGVSPPVKRNESFFDG

GAKYHVALHVPYLRYFVAFILQFQFHEHLCTVAKKVDEHHPFHECDIYGEK

NAGDVLKKGLSLGRSKPWPDVLEIMAGTRQMSASSLKKYYEPLEKWLDERI

KNEVVGWDKANVQDYMGVPSFANKVDFSAAAVLASIGVILFCWKNISL.

In some examples, a portion of the full length native Bm86 tick polypeptide sequence is used. Suitable portions include, but are not limited to WRWTIFTGETPFQK [SEQ ID NO: 24] LREIYPG [SEQ ID NO: 25], NEVVGWDK [SEQ ID NO: 26], LWEDLSPLYK [SEQ ID NO: 27], QYYIPYIK [SEQ ID NO: 28], and YYEPLEK [SEQ ID NO: 29]. In some of the same or other embodiments, the Bm86 polypeptide antigen comprises a fusion protein of two, three, or more antigenic peptides derived from the full length Bm86 protein. Each antigenic peptide may be conjugated directly to the previous antigenic peptide, or alternatively linked via an amino acid linked. Suitable Bm86 fusion proteins include those described in U.S. Pat. No. 8,110,202, the entire content of which is incorporated herein by reference. Particularly suitable Bm86 fusion proteins include those designated SBm4912, SBm7462, and SBm19733, with the amino acid sequences presented in Table 5.

TABLE 5

| Bm86 Fusion Protein | Amino acid sequence |
|---|---|
| SBm4912 | CLSKHVLRKLQACEHSSICSDFGNEFC RNACDCGEWGAMNMTTRC [SEQ ID NO: 30] |
| SBm7462 | CLSKHVLRKLQACEHCDCGEWGAMN MTTRSSICSDFGNEFCRNAC [SEQ ID NO: 31] |
| SBm19733 | CLSKHVLRKLQACEHKEKSSICSDFGN EFCRNAKEKCDCGEWGAMNMTTRC [SEQ ID NO: 32] |

3. Carrier Proteins and Other Conjugates

In some embodiments, the polypeptides described for use in the compositions and methods of the present invention may be conjugated to a carrier protein which suitably comprises at least one T-cell epitope. One such carrier protein is the Keyhole Limpet Hemocyanin (KLH) carrier protein (e.g., UniProtKB accession no. Q53IP9; SEQ ID NO: 6), which beneficially contains multiple T-cell epitopes. Alternative carrier proteins that are suitable for use with the present invention include, but are not limited to, *Concholepas concholepas* Hemocyanin (CCH) (UniProtKB accession no. P84619 and P84620; SEQ ID NO: 18 and 19, respectively), ovalbumin (e.g., UniProtKB accession no. P01012; SEQ ID NO: 20), bovine serum albumin (e.g., UniProtKB accession no. P02769; SEQ ID NO: 21), and cholera toxin B (e.g., UniProtKB accession no. P01556; SEQ ID NO: 22).

3.1 Promiscuous T-Cell Epitopes

In some embodiments, the immunogenic agents of the invention also comprise a promiscuous T-cell epitope (e.g., a heterologous CD4+ T-cell epitope) in order to prepare a composition of greater immunological efficacy. Promiscuous T-cell epitopes that are suitable for use with the polypeptide molecules of the present invention are typically associated with the class II major histocompatibility complex (MHC), and can be derived from naturally occurring immunogens derived from any pathogenic microorganism. Naturally occurring promiscuous T-cell epitopes can also be conservatively modified by single or multiple amino acid additions, deletions, or substitutions (e.g., within classes of charged, hydrophilic/hydrophobic, steric amino acids) to obtain candidate sequences that can be screened for their ability to enhance immunogenicity.

Non-naturally occurring promiscuous T-cell epitopes can be artificially synthesized to obtain sequences that have comparable or greater immunogenicity. Artificial promiscuous T-cell epitopes (e.g., heterologous CD4+ T-cell epitopes) can range in size from about 7 to about 50 amino acid residues in length and can have structural features such as amphipathic helices (alpha-helical structures with hydrophobic amino acid residues dominating one face of the helix and charged or polar residues dominating the surrounding faces). The promiscuous T-cell epitopes may also contain additional primary amino acid patterns, such as a glycine or a charged residue followed by two to three hydrophobic residues, followed in turn by a charged or polar residue (i.e., a Rothbard sequence). In addition, promiscuous T-cell epitopes often conform with the "1, 4, 5, 8 rule", where a positively charged residue is followed by hydrophobic residues at the fourth, fifth, and eighth positions after the charged residue.

These features may be incorporated into the designs of artificial promiscuous T-cell epitopes. Variable positions and preferred amino acids are available for MHC-binding motifs (see, Meister et al., *Vaccine*, 1995, 13:581-591). For example, the degenerate promiscuous T-cell epitope described in the International Patent Publication No. WO95/11998 as SSAL1TH1 has the degenerate sequence (Asp/Glu)-(Leu/Ile/Val/Phe)-Ser-(Asp/Gly)-(Leu/Ile/Val/Phe)-(Lys/Arg)-Gly-(Leu/Ile/Val/Phe)-(Leu/Ile/Val/Phe)-(Leu/Ile/Val/Phe)-His-(Lys/Arg)-Leu/Ile/Val/Phe)-(Asp/Glu)-Gly-(Leu/Ile/Val/Phe).

Given this structural-functional guidance, it should be understood that many candidates for artificial promiscuous T-cell epitopes can be generated by conventional methods and screened for their ability to enhance the immune response of an associated antigen.

By way of an example, particular promiscuous T-cell epitopes useful in the embodiments disclosed herein include measles virus protein F amino acid sequence LSEIKGVIVHRLEGV (SEQ ID NO: 9); and tetanus toxin (UniProtKB accession no. P04958; SEQ ID NO: 10) including for example peptides with any of the amino acid sequences VDDALINSTKIYSYFPSV (SEQ ID NO: 11), QYIKANSKFIGITEL (SEQ ID NO: 12), or FNNFTVSFWLRVPKVSASHLE (SEQ ID NO: 13). Yet other tetanus toxin-derived peptide amino acid sequences that are suitable for use as promiscuous T-cell epitopes may be selected from residues 590-603, 615-629, 639-652, 830-843, and 947-967 of the full-length native tetanus toxin amino acid sequence set forth in SEQ ID NO: 10:

MPITINNFRYSDPVNNDTIIMMEPPYCKGLDIYYKAFKITDRIWIVPERYE

FGTKPEDFNPPSSLIEGASEYYDPNYLRTDSDKDRFLQTMVKLFNRIKNNV

AGEALLDKIINAIPYLGNSYSLLDKFDTNSNSVSFNLLEQDPSGATTKSAM

LTNLIIFGPGPVLNKNEVRGIVLRVDNKNYFPCRDGFGSIMQMAFCPEYVP

TFDNVIENITSLTIGKSKYFQDPALLLMHELIHVLHGLYGMQVSSHEIIPS

KQEIYMQHTYPISAEELFTFGGQDANLISIDIKNDLYEKTLNDYKAIANKL

SQVTSCNDPNIDIDSYKQIYQQKYQFDKDSNGQYIVNEDKFQILYNSIMYG

FTEIELGKKFNIKTRLSYFSMNHDPVKIPNLLDDTIYNDTEGFNIESKDLK

SEYKGQNMRVNTNAFRNVDGSGLVSKLIGLCKKIIPPTNIRENLYNRTASL

TDLGGELCIKIKNEDLTFIAEKNSFSEEPFQDEIVSYNTKNKPLNFNYSLD

KIIVDYNLQSKITLPNDRTTPVTKGIPYAPEYKSNAASTIEIHNIDDNTIY

QYLYAQKSPTTLQRITMTNSVDDALINSTKIYSYFPSVISKVNQGAQGILF

LQWVRDIIDDFTNESSQKTTIDKISDVSTIVPYIGPALNIVKQGYEGNFIG

ALETTGVVLLLEYIPEITLPVIAALSIAESSTQKEKIIKTIDNFLEKRYEK

```
-continued
WIEVYKLVKAKWLGTVNTQFQKRSYQMYRSLEYQVDAIKKIIDYEYKIYSG

PDKEQIADEINNLKNKLEEKANKAMININIFMRESSRSFLVNQMINEAKKQ

LLEFDTQSKNILMQYIKANSKFIGITELKKLESKINKVFSTPIPFSYSKNL

DCWVDNEEDIDVILKKSTILNLDINNDIISDISGFNSSVITYPDAQLVPGI

NGKAIHLVNNESSEVIVHKAMDIEYNDMFNNFTVSFWLRVPKVSASHLEQY

GTNEYSIISSMKKHSLSIGSGWSVSLKGNNLIWTLKDSAGEVRQITFRDLP

DKFNAYLANKWVFITITNDRLSSANLYINGVLMGSAEITGLGAIREDNNIT

LKLDRCNNNNQYVSIDKFRIFCKALNPKEIEKLYTSYLSITFLRDFWGNPL

RYDTEYYLIPVASSSKDVQLKNITDYMYLTNAPSYTNGKLNIYYRRLYNGL

KFIIKRYTPNNEIDSFVKSGDFIKLYVSYNNNEHIVGYPKDGNAFNNLDRI

LRVGYNAPGIPLYKKMEAVKLRDLKTYSVQLKLYDDKNASLGLVGTHNGQI

GNDPNRDILIASNWYFNHLKDKILGCDWYFVPTDEGWTND
```

Various other promiscuous T-cell epitopes are described in U.S. Pat. Nos. 5,759,552, 6,107,021, and 6,783,761; and in U.S. Patent Publication No. 2004/0086524, and the references therein.

Yet another useful immunogenic protein, although not strictly a promiscuous T-cell epitope, is a cholera toxin B epitope (CTB).

3.2 Linker Sequences

The polypeptide antigen may be separated from another moiety (e.g., an immunogenic carrier protein, or promiscuous T-cell epitope) by any suitable linker known in the art. The linker generally includes any amino acid residue that cannot be unambiguously assigned either component. Linkers are frequently used in the field of protein engineering to interconnect different functional units, e.g., in the creation of single-chain variable fragment (scFv) constructs derived from antibody variable light (VL) and variable heavy (VH) chains. They are generally conformationally flexible in solution, and are suitably and predominantly composed of polar amino acid residue types. Typical (frequently used) amino acids in flexible linkers are serine and glycine. Less preferably, flexible linkers may also include alanine, threonine and proline. Thus, an intervening linker suitable for use in the present invention is preferably flexible in conformation to ensure relaxed (unhindered) association of the tick polypeptide and carrier protein. Suitable linkers for use in the polypeptides envisaged herein will be clear to the skilled person, and may generally be any linker used in the art to link amino acid sequences, as long as the linkers are structurally flexible, in the sense that they do not affect the activity of either component being conjugated.

In some embodiments, the at least one polypeptide antigen is conjugated to the carrier protein (or an intervening linker sequence) by way of a cysteine amino acid residue.

Alternatively, the skilled person will be able to determine the optimal linkers, optionally after performing a limited number of routine experiments. The intervening linker is suitably an amino acid sequence generally consisting of at least 1 amino acid residue and usually consisting of at least 2 amino acid residues, with a non-critical upper limit chosen for reasons of convenience being about 100 amino acid residues. In particular embodiments, the linker consists of about 1 to about 20 amino acid residues, or about 20 to about 40 amino acid residues, usually about 1 to about 10 amino acid residues, typically about 1 to about 15 amino acid residues. In particular, non-limiting embodiments, at least 50% of the amino acid residues of a linker sequence are selected from the group proline, glycine, and serine. In further non-limiting embodiments, at least 60%, such as at least 70%, such as for example 80% and more particularly 90% of the amino acid residues of a linker sequence are selected from the group proline, glycine, and serine. In other particular embodiments, the linker sequences essentially consist of polar amino acid residues; in such particular embodiments, at least 50%, such as at least 60%, such as for example 70% or 80% and more particularly 90% or up to 100% of the amino acid residues of a linker sequence are selected from the group consisting of glycine, serine, threonine, alanine, proline, histidine, asparagine, aspartic acid, glutamine, glutamic acid, lysine and arginine. In specific embodiments, linker sequences may include $[GGSG]_n GG$, $[GGGGS]_n$, $[GGGGG]_n$, $[GGGKGGGG]_n$, $[GGGNGGGG]_n$, $[GGGCGGGG]_n$, wherein n is an integer from 1 to 10, suitably 1 to 5, more suitably 1 to 3.

In addition to spacing the polypeptide antigen from any other component, the linker may comprise one or more ancillary functionalities. For example, the linker may comprise a purification moiety that facilitates purification of the immunostimulatory polypeptide.

Purification moieties typically comprise a stretch of amino acids that enables recovery of the chimeric polypeptide through affinity binding. Numerous purification moieties or 'tags' are known in the art, illustrative examples of which include biotin carboxyl carrier protein-tag (BCCP-tag), Myc-tag (c-myc-tag), Calmodulin-tag, FLAG-tag, HA-tag, His-tag (Hexahistidine-tag, His6, 6H), Maltose binding protein-tag (MBP-tag), Nus-tag, Chitin-binding protein-tag (CBP-tag) Glutathione-S-transferase-tag (GST-tag), Green fluorescent protein-tag (GFP-tag), Polyglutamate-tag, Amyloid beta-tag, Thioredoxin-tag, S-tag, Softag 1, Softag 3, Strep-tag, Streptavidin-binding peptide-tag (SBP-tag), biotin-tag, streptavidin-tag and V5-tag.

4. Nucleic Acid Molecules

In some embodiments, the immunogenic agents of the invention are prepared by recombinant techniques. For example, the agents may be prepared by a procedure including the steps of: (a) preparing a construct comprising a polynucleotide sequence that encodes an immunogenic agent that comprises a M1-2A Clone 91 polypeptide and that is operably linked to a regulatory element; (b) introducing the construct into a host cell; (c) culturing the host cell to express the polynucleotide sequence to thereby produce the encoded immunogenic agent; and (d) isolating the immunogenic agent from the host cell. In illustrative examples, the nucleotide sequence encodes at least a biologically active fragment of the sequences set forth in SEQ ID NO: 1, or a variant thereof. For example, the nucleic acid molecule may encode the polypeptide sequence set forth in one or both of SEQ ID NO: 1 or 3 or 4 or any other polypeptide sequence described herein. Recombinant proteins and polypeptides can be conveniently prepared using standard protocols as described for example in Sambrook, et al., (1989, supra), in particular Sections 16 and 17; Ausubel et al., (1994, supra), in particular Chapters 10 and 16; and Coligan et al., Current Protocols in Protein Science (John Wiley & Sons, Inc. 1995-1997), in particular Chapters 1, 5 and 6.

Exemplary nucleotide sequences that encode the polypeptides of the invention encompass full-length M1-2A Clone 91 tick polypeptide genes, as well as portions of the full-length or substantially full-length nucleotide sequences of the tick polypeptide genes or their transcripts or DNA copies of these transcripts.

The invention also contemplates nucleic acid molecules that correspond to variant nucleic acid sequences encoding the M1-2A Clone 91 tick polypeptide. Nucleic acid variants can be naturally-occurring, such as allelic variants (same locus), homologues (different locus), and orthologues (different organism) or can be non naturally-occurring. Naturally-occurring nucleic acid variants (also referred to herein as polynucleotide variants) such as these can be identified with the use of well-known molecular biology techniques, as, for example, with polymerase chain reaction (PCR) and hybridization techniques as known in the art. Non-naturally occurring polynucleotide variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product). For nucleotide sequences, conservative variants include those sequences that, because of the degeneracy of the genetic code, encode the amino acid sequence of the native tick polypeptide. Variant nucleotide sequences also include synthetically derived nucleotide sequences, such as those generated, for example, by using site-directed mutagenesis but which still encode a tick polypeptide. Generally, variants of a particular M1-2A Clone 91 tick polypeptide coding sequence will have at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more sequence identity to that particular M1-2A Clone 91 coding sequence as determined by sequence alignment programs described elsewhere herein using default parameters. In some embodiments, the tick polypeptide coding sequence displays at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more sequence identity to a coding sequence set forth in SEQ ID NO: 2, or a complement thereof.

M1-2A Clone 91-encoding nucleotide sequences can be used to isolate corresponding sequences and alleles from other organisms, particularly other tick species. Methods are readily available in the art for the hybridization of nucleic acid sequences. Coding sequences from other organisms may be isolated according to well known techniques based on their sequence identity with the coding sequences set forth herein.

In certain embodiments, a M1-2A Clone 91 tick polypeptide is encoded by a polynucleotide that hybridizes to a disclosed nucleotide sequence under very high stringency conditions.

4.1 Expression Vectors

In some embodiments, the polypeptide antigen can be produced inside a cell (for example, an antigen-presenting cell) by introduction of one or more expression constructs that encode the polypeptide antigen. As described, for example, in U.S. Pat. No. 5,976,567 (Inex), the expression of natural or synthetic nucleic acids is typically achieved by operably linking a nucleic acid of interest to a regulatory element (e.g., a promoter, which may be either constitutive or inducible), suitably incorporating the construct into an expression vector, and introducing the vector into a suitable host cell. Typical vectors contain transcription and translation terminators, transcription and translation initiation sequences and promoters useful for regulation of the expression of the particular nucleic acid. The vectors optionally comprise generic expression cassettes containing at least one independent terminator sequence, sequences permitting replication of the cassette in eukaryotes, prokaryotes, or both (e.g., shuttle vectors) and selection markers for both prokaryotic and eukaryotic systems. Vectors may be suitable for replication and integration in prokaryotes, eukaryotes, or both (see, Giliman and Smith (1979), *Gene* 8: 81-97; Roberts et al. (1987), *Nature* 328: 731-734; Berger and Kimmel, Guide to Molecular Cloning Techniques, Methods in Enzymology, volume 152, Academic Press, Inc., San Diego, Calif. (Berger); Sambrook et al. (1989), MOLECULAR CLONING—A LABORATORY MANUAL (2nd ed.) Vol. 1-3, Cold Spring Harbor Laboratory, Cold Spring Harbor Press, N.Y., (Sambrook); and F. M. Ausubel et al., CURRENT PROTOCOLS IN MOLECULAR BIOLOGY, eds., Current Protocols, a joint venture between Greene Publishing Associates, Inc. and John Wiley & Sons, Inc., (1994 Supplement) (Ausubel)).

Expression vectors containing regulatory elements from eukaryotic viruses such as retroviruses are typically used for expression of nucleic acid sequences in eukaryotic cells. SV40 vectors include pSVT7 and pMT2. Vectors derived from bovine papilloma virus include pBV-1 MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

A regulatory polynucleotide suitably comprises transcriptional and/or translational control sequences, which will generally be appropriate for the host cell used for expression of the antigen-encoding polynucleotide. Typically, the transcriptional and translational regulatory control sequences include, but are not limited to, a promoter sequence, a 5' non-coding region, a cis-regulatory region such as a functional binding site for transcriptional regulatory protein or translational regulatory protein, an upstream open reading frame, transcriptional start site, translational start site, and/or nucleotide sequence which encodes a leader sequence, termination codon, translational stop site and a 3' non-translated region. Constitutive or inducible promoters as known in the art are contemplated by the invention. The promoters may be either naturally occurring promoters, or hybrid promoters that combine elements of more than one promoter. Promoter sequences contemplated by the present invention may be native to the host cell to be introduced or may be derived from an alternative source, where the region is functional in the host cell.

The synthetic construct of the present invention may also comprise a 3' non-translated sequence. A 3' non-translated sequence refers to that portion of a gene comprising a DNA segment that contains a polyadenylation signal and any other regulatory signals capable of effecting mRNA processing or gene expression. The polyadenylation signal is characterised by effecting the addition of polyadenylic acid tracts to the 3' end of the mRNA precursor. Polyadenylation signals are commonly recognised by the presence of homology to the canonical form 5' AATAAA-3' although variations are not uncommon. The 3' non-translated regulatory DNA sequence preferably includes from about 50 to 1,000 nucleotide base pairs and may contain transcriptional and translational termination sequences in addition to a polyadenylation signal and any other regulatory signals capable of effecting mRNA processing or gene expression.

In a preferred embodiment, the expression vector further contains a selectable marker gene to allow the selection of transformed host cells. Selection genes are well known in the art and will vary with the host cell used.

The expression vector may also include a fusion partner (typically provided by the expression vector) so that the recombinant polypeptide of the invention is expressed as a fusion polypeptide with said fusion partner. The main advantage of fusion partners is that they assist identification and/or purification of said fusion polypeptide. In order to express said fusion polypeptide, it is necessary to ligate an antigen-encoding polynucleotide according to the invention into the expression vector so that the translational reading frames of the fusion partner and the polynucleotide coincide. Well known examples of fusion partners include, but are not limited to, glutathione-S-transferase (GST), Fc portion of human IgG, maltose binding protein (MBP) and hexahistidine ($HIS_6$), which are particularly useful for isolation of the fusion polypeptide by affinity chromatography. For the purposes of fusion polypeptide purification by affinity chromatography, relevant matrices for affinity chromatography are glutathione-, amylose-, and nickel- or cobalt-conjugated resins respectively. Many such matrices are available in "kit" form, such as the QIAEXPRESS™ system (Qiagen) useful with ($His_6$) fusion partners and the Pharmacia GST purification system. In a preferred embodiment, the recombinant polynucleotide is expressed in the commercial vector pFLAG as described more fully hereinafter. Another fusion partner well known in the art is green fluorescent protein (GFP). This fusion partner serves as a fluorescent "tag" which allows the fusion polypeptide of the invention to be identified by fluorescence microscopy or by flow cytometry. The GFP tag is useful when assessing subcellular localisation of the fusion polypeptide of the invention, or for isolating cells which express the fusion polypeptide of the invention. Flow cytometric methods such as fluorescence activated cell sorting (FACS) are particularly useful in this latter application. Preferably, the fusion partners also have protease cleavage sites, such as for factor $X_a$ or thrombin, which allow the relevant protease to partially digest the fusion polypeptide of the invention and thereby liberate the recombinant polypeptide of the invention therefrom. The liberated polypeptide can then be isolated from the fusion partner by subsequent chromatographic separation. Fusion partners according to the invention also include within their scope "epitope tags", which are usually short peptide sequences for which a specific antibody is available. Well known examples of epitope tags for which specific monoclonal antibodies are readily available include c-Myc, influenza virus haemagglutinin and FLAG tags.

The step of introducing into the host cell the recombinant polynucleotide may be effected by any suitable method including transfection, and transformation, the choice of which will be dependent on the host cell employed. Such methods are well known to those of skill in the art.

Recombinant polypeptides of the invention may be produced by culturing a host cell transformed with an expression vector containing nucleic acid encoding a polypeptide, biologically active fragment, variant or derivative according to the invention. The conditions appropriate for protein expression will vary with the choice of expression vector and the host cell. This is easily ascertained by one skilled in the art through routine experimentation. Suitable host cells for expression may be prokaryotic or eukaryotic. One preferred host cell for expression of a polypeptide according to the invention is a bacterium. The bacterium used may be *Escherichia coli*. Alternatively, the host cell may be an insect cell such as, for example, Sf9 cells that may be utilised with a baculovirus expression system.

The recombinant protein may be conveniently prepared by a person skilled in the art using standard protocols as for example described in Sambrook, et al., MOLECULAR CLONING. A LABORATORY MANUAL (Cold Spring Harbor Press, 1989), in particular Sections 16 and 17; Ausubel et al., CURRENT PROTOCOLS IN MOLECULAR BIOLOGY (John Wiley & Sons, Inc. 1994-1998), in particular Chapters 10 and 16; and Coligan et al., CURRENT PROTOCOLS IN PROTEIN SCIENCE (John Wiley & Sons, Inc. 1995-1997), in particular Chapters 1, 5 and 6.

Alternatively, the modified antigen may be synthesised using solution synthesis or solid phase synthesis as described, for example, in Chapter 9 of Atherton and Shephard (supra) and in Roberge et al. (1995, *Science* 269: 202).

While a variety of vectors may be used, it should be noted that viral expression vectors are useful for modifying eukaryotic cells because of the high efficiency with which the viral vectors transfect target cells and integrate into the target cell genome. Illustrative expression vectors of this type can be derived from viral DNA sequences including, but not limited to, adenovirus, adeno-associated viruses, herpes-simplex viruses and retroviruses such as B, C, and D retroviruses as well as spumaviruses and modified lentiviruses. Suitable expression vectors for transfection of animal cells are described, for example, by Wu and Ataai (2000, *Curr. Opin. Biotechnol.* 11(2), 205-208), Vigna and Naldini (2000, *J. Gene Med.* 2(5), 308-316), Kay et al. (2001, *Nat. Med.* 7(1), 33-40), Athanasopoulos, et al. (2000, *Int. J. Mol. Med.* 6(4): 363-375) and Walther and Stein (2000, *Drugs* 60(2): 249-271).

The polypeptide-encoding portion of the expression vector may comprise a naturally-occurring sequence or a variant thereof, which has been engineered using recombinant techniques. In one example of a variant, the codon composition of an antigen-encoding polynucleotide is modified to permit enhanced expression of the polypeptide antigen in a mammalian (e.g., cattle) host using methods that take advantage of codon usage bias, or codon translational efficiency in specific mammalian (e.g., cattle) cell or tissue types as set forth, for example, in International Patent Publication Nos. WO99/02694 and WO00/42215. Briefly, these latter methods are based on the observation that translational efficiencies of different codons vary between different cells or tissues and that these differences can be exploited, together with codon composition of a gene, to regulate expression of a protein in a particular cell or tissue type. Thus, for the construction of codon-optimised polynucleotides, at least one existing codon of a parent polynucleotide is replaced with a synonymous codon that has a higher translational efficiency in a target cell or tissue than the existing codon it replaces. Although it is preferable to replace all the existing codons of a parent nucleic acid molecule with synonymous codons which have that higher translational efficiency, this is not necessary because increased expression can be accomplished even with partial replacement. Suitably, the replacement step affects 5%, 10%, 15%, 20%, 25%, 30%, more preferably 35%, 40%, 50%, 60%, 70% (and every percentage integer in between) or more of the existing codons of a parent polynucleotide.

The expression vector is compatible with the antigen-presenting cell in which it is introduced such that the antigen-encoding polynucleotide is expressible by the cell. The expression vector is introduced into the antigen-presenting cell by any suitable means which will be dependent on the particular choice of expression vector and antigen-presenting cell employed. Such means of introduction are well-known to those skilled in the art. For example, introduction can be effected by use of contacting (e.g., in the case of viral vectors), electroporation, transformation, transduction, conjugation or triparental mating, transfection, infection membrane fusion with cationic lipids, high-velocity bombardment with DNA-coated microprojectiles, incubation with calcium phosphate-DNA precipitate, direct microinjection into single cells, and the like. Other methods also are available and are known to those skilled in the art. Alternatively, the vectors are introduced by means of cationic lipids, e.g., liposomes. Such liposomes are commercially available (e.g., LIPOFECTIN®, LIPOFECTAMINE™, and the like, supplied by Life Technologies, Gibco BRL, Gaithersburg, Md.).

5. Construct Systems

The present invention may utilise any construct system for eliciting simultaneously a host-protective antibody response and a cell-mediated immune response against a M1-2A Clone 91 tick polypeptide to therapeutically and/or prophylactically treat a tick infestation. The strategy involves administering to an individual a first antigen corresponding to the M1-2A Clone 91 tick polypeptide, and being suitably intracellularly resistant to proteolysis. In addition, a second antigen, corresponding to a modified form of the M1-2A Clone 91tick polypeptide, is administered to the individual, wherein the rate of intracellular proteolytic degradation of the second antigen is increased, enhanced or otherwise elevated relative to the first antigen. The first and second antigens may be administered in proteinaceous form (ie, a peptide or polypeptide), or in nucleic acid form, or a combination thereof. The antigenic determinant(s) or epitope(s) of the first antigen and the second antigen may be the same or different. Accordingly, the epitope-containing sequence of the first antigen and the second antigen may be the same or different. Preferably, the first antigen and the second antigen comprise the same epitope(s). Suitably, when corresponding epitopes are different between the first antigen and the second antigen, such epitopes are preferably capable of eliciting the production of elements that bind to a corresponding epitope of the tick polypeptide.

5.1 Production of Modified Antigen

The second or modified antigen according to the present invention may be prepared using any suitable technique that renders it less resistant to proteolysis intracellularly relative to a first antigen corresponding to the tick polypeptide of interest. However, it should be noted that the present invention is not dependent on, and not directed to, any one particular technique by which the second or modified antigen is produced. The intracellular half life of a first or tick polypeptide is suitably greater than about 3 minutes, preferably greater than about 5 minutes, more preferably greater than about 10 minutes, even more preferably greater than about 15 minutes, even more preferably greater than about 30 minutes, even more preferably greater than about 1 hour, even more preferably greater than about 10 hours, even more preferably greater than about 24 hours, and still even more preferably greater than about 50 hours. Suitably, a proteolytically resistant antigen is one that retains greater than about 10% of its tertiary structure after about 3 minutes, preferably after about 5 minutes, more preferably after about 10 minutes, even more preferably after about 15 minutes, even more preferably after about 30 minutes, even more preferably after about 1 hour, even more preferably after about 10 hours, even more preferably after about 24 hours, and still even more preferably after about 50 hours at intracellular or intracellular-like conditions. Preferably, a proteolytically resistant antigen is one that retains greater than about 20% of its tertiary structure after about 3 minutes, preferably after about 5 minutes, more preferably after about 10 minutes, even more preferably after about 15 minutes, even more preferably after about 30 minutes, even more preferably after about 1 hour, even more preferably after about 10 hours, even more preferably after about 24 hours, and still even more preferably after about 50 hours at intracellular or intracellular-like conditions. More preferably, a proteolytically resistant antigen is one that retains greater than about 50% of its tertiary structure after about 3 minutes, preferably after about 5 minutes, more preferably after about 10 minutes, even more preferably after about 15 minutes, even more preferably after about 30 minutes, even more preferably after about 1 hour, even more preferably after about 10 hours, even more preferably after about 24 hours, and still even more preferably after about 50 hours at intracellular or intracellular-like conditions. The intracellular or intracellular-like conditions are preferably physiological for the cell type. The cell type is preferably an antigen presenting cell, more preferably a professional antigen presenting cell including, but not restricted to, a dendritic cell, a macrophage and a B cell. The temperature of the intracellular or intracellular-like conditions is preferably physiological for the cell type. Exemplary temperatures for mammalian cells range suitably from about 30° C. to about 42° C., and preferably from about 35° C. to about 37° C. The intracellular half life of the second antigen is suitably less than about 50 hours, preferably less than about 10 hours, more preferably less than about 1 hour, even more preferably less than about 30 minutes, even more preferably less than about 15 minutes, even more preferably less than about 10 minutes and still even more preferably less than about 3 minutes. At a minimum, enhanced proteolytic degradation of the second antigen refers to a level of proteolytic degradation that is at least about 5%, preferably at least about 10%, more preferably at least about 20%, even more preferably at least about 40%, even more preferably at least about 50%, even more preferably at least about 60%, even more preferably at least about 70%, even more preferably at least about 80%, even more preferably at least about 90%, still even more preferably at least about 95%, greater than that of the target or first antigen. Assays for measuring degradation of proteins are known to persons of skill in the art. For example, proteolytic degradation may be measured using a mammalian cell lysate assay including, but not restricted to, the reticulocyte lysate assay of Bachmair et al. in U.S. Pat. No. 5,646,017.

Suitably, second antigen may be derived from or correspond to the M1-2A Clone 91 tick polypeptide. Preferably, the second antigen is modified to include an intracellular degradation signal or degron. The degron is suitably an ubiquitin-mediated degradation signal selected from an ubiquitin acceptor, an ubiquitin or combination thereof.

In another embodiment, the second antigen is modified to include, or is otherwise associated with, an ubiquitin acceptor which is a molecule that preferably contains at least one residue appropriately positioned from the N-terminal of the antigen as to be able to be bound by ubiquitin polypeptides. Such residues preferentially have an epsilon amino group such as lysine. Physical analysis demonstrates that multiple lysine residues function as ubiquitin acceptor sites (see, King et al., 1996, *Mol. Biol. Cell* 7: 1343-1357; and King et al., 1996, *Science* 274: 1652-1659). Examples of other ubiquitin acceptors include lacI or Sindis virus RNA polymerase.

In yet another embodiment, the second antigen is conjugated to a ubiquitin polypeptide to produce a second or modified antigen whose rate of intracellular proteolytic degradation is increased, enhanced or otherwise elevated relative to the parent antigen. Ubiquitination at the N-terminal of the protein specifically targets the protein for degradation via the ubiquitin-proteosome pathway. In a preferred embodiment of this type, the ubiquitin polypeptide is fused, or otherwise conjugated, to the second antigen. Suitably, the ubiquitin polypeptide is of mammalian origin, more preferably of bovine or other ungulate origin. In an exemplary embodiment of this type, the ubiquitin polypeptide comprises the amino acid sequence set forth in SEQ ID NO: 7 (ubiquitin from *Bos taurus*; UniProtKB accession no. P63048). In a more specific embodiment of this type, the ubiquitin polypeptide comprises, consists, or consists essentially of the amino acid sequence set forth in SEQ ID NO: 7. In some other embodiments, the ubiquitin polypeptide comprises two or more copies of the sequence set forth in SEQ ID NO: 24 or of residues 1-76 of SEQ ID NO: 24.

In some embodiments, the ubiquitin-antigen fusion protein is suitably produced by covalently attaching an antigen corresponding to the M1-2A Clone 91 tick polypeptide to a ubiquitin or a biologically active fragment thereof. Covalent attachment may be effected by any suitable means known to persons of skill in the art. For example, protein conjugates may be prepared by linking proteins together using bifunctional reagents. The bifunctional reagents can be homobifunctional or heterobifunctional.

Other protein processing signals that destabilise an antigen of interest and allow for enhanced intracellular degradation are contemplated in the present invention. These other methods may not necessarily be mediated by the ubiquitin pathway, but may otherwise permit degradation of proteins in the cytoplasm via proteosomes. For example, the present invention contemplates the use of other intracellular processing signals which govern the rate(s) of intracellular protein degradation including, but not limited to, those described by Bohley et al. (1996, *Biol. Chem. Hoppe. Seyler* 377: 425-435). Such processing signals include those that allow for phosphorylation of the target protein (Yaglom et al., 1996, *Mol. Cell Biol.* 16: 3679-3684; Yaglom et al., 1995, *Mol. Cell Biol.* 15: 731-741). Also contemplated by the present invention are modification of an parent antigen that allow for post-translational arginylation (Ferber et al. 1987, *Nature* 326: 808-811; Bohley et al., 1991, *Biomed. Biochim. Acta* 50: 343-346) of the protein which can enhance its rate(s) of intracellular degradation. The present invention also contemplates the use of certain structural features of proteins that can influence higher rates of intracellular protein turn-over, including protein surface hydrophobicity, clusters of hydrophobic residues within the protein (Sadis et al., 1995, *Mol. Cell Biol.* 15: 4086-4094), certain hydrophobic pentapeptide motifs at the protein's carboxy-terminus (C-terminus) (e.g., ARINV, as found on the C-terminus of ornithine decarboxylase (Ghoda et al., 1992, *Mol. Cell Biol.* 12: 2178-2185; Li, et al., 1994, *Mol. Cell Biol.* 14: 87-92), or AANDENYALAA (, as found in C-terminal tags of aberrant polypeptides (Keiler et al., 1996, *Science* 271: 990-993,) or PEST regions (regions rich in proline (P), glutamic acid (E), serine (S), and threonine (T), which are optionally flanked by amino acids comprising electropositive side chains (Rogers et al. 1986, *Science* 234 (4774): 364-368; 1988, *J. Biol. Chem.* 263: 19833-19842). Moreover, certain motifs have been identified in proteins that appear necessary and possibly sufficient for achieving rapid intracellular degradation. Such motifs include RXAL-GXIXN region (where X=any amino acid) in cyclins (Glotzer et al., 1991, *Nature* 349: 132-138) and the KTKR-NYSARD motif in isocitrate lyase (Ordiz et al., 1996, *FEBS Lett.* 385: 43-46).

The present invention also contemplates enhanced cellular degradation of a parent antigen which may occur by the incorporation into that antigen known protease cleavage sites. For example amyloid beta-protein can be cleaved by beta- and gamma-secretase (see, Iizuka et al., 1996, *Biochem. Biophys. Res. Commun.* 218: 238-242) and the two-chain vitamin K-dependent coagulation factor X can be cleaved by calcium-dependent endoprotease(s) in liver (see, Wallin et al., 1994, *Thromb. Res.* 73: 395-403).

In an alternate embodiment, a ubiquitin-antigen fusion protein is suitably expressed by a synthetic chimeric polynucleotide comprising a first nucleic acid sequence, which encodes a polypeptide antigen that comprises an amino acid sequence that corresponds to the tick polypeptide, and which is linked downstream of, and in reading frame with, a second nucleic acid sequence encoding a ubiquitin or biologically active fragment thereof. In a preferred embodiment of this type, the second polynucleotide comprises a first nucleic acid sequence, which encodes a polypeptide antigen comprising an amino acid sequence corresponding to the tick polypeptide, and which is linked immediately adjacent to, downstream of, and in reading frame with, a second nucleic acid sequence encoding a ubiquitin or biologically active fragment thereof. In another embodiment, the second polynucleotide comprises a first nucleic acid sequence, which encodes an antigen corresponding to the tick polypeptide, and which is linked upstream of, and in reading frame with, a second nucleic acid sequence encoding a ubiquitin or biologically active fragment thereof. In yet another embodiment of this type, the second polynucleotide comprises a first nucleic acid sequence, which encodes an antigen corresponding to the tick polypeptide, and which is linked immediately adjacent to, upstream of, and in reading frame with, a second nucleic acid sequence encoding a ubiquitin or biologically active fragment thereof. For example, when the subject being administered with the vaccine is bovine, the ubiquitin-encoding nucleic acid sequence comprises the following nucleic acid sequence:

```
                                              (SEQ ID NO: 8)
ATGCAGATCTTTGTGAAGACCCTGACGGGCAAGACCATCACCCTTGAGGTC

GAGCCCAGTGACACCATTGAGAATGTCAAAGCCAAAATCCAAGACAAGGAG

GGCATCCCACCTGACCAGCAGCGGCTGATCTTCGCTGGCAAACAGCTGGAG

GATGGCCGCACTCTGTCAGATTATAATATCCAGAAAGAGTCCACCCTGCAC

TTGGTGCTTCGTCTGCGAGGCGGC.
```

6. Immunostimulatory Compositions

The polypeptide antigens of the present invention can be used as active ingredients for the therapeutic treatment and/or prophylaxis of tick infestation. These therapeutic treatment and/or prophylactic agents can be administered to a subject (e.g., cattle) either in isolation or as compositions where they are mixed with pharmaceutically acceptable carriers, diluents, and/or adjuvants.

Depending on the specific conditions being treated, composition s for therapy and/or prophylaxis may be formulated and administered systemically or locally. Techniques for formulation and administration may be found in "Remington's Pharmaceutical Sciences," Mack Publishing Co., Easton, Pa., latest edition. Suitable routes may, for example, include intradermal injection. For injection, the therapeutic agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art. Intramuscular and subcutaneous injection is appropriate, for example, for administration of immunogenic compositions, vaccines and DNA vaccines. In some specific embodiments, the pharmaceutical compositions are formulated for intradermal administration.

The pharmaceutical compositions of the invention can be formulated readily using pharmaceutically acceptable carriers well known in the art into dosages suitable for administration. Such carriers enable the compounds of the invention to be formulated in dosage forms such as tablets, pills, capsules, liquids, gels, syrups, slurries, suspensions and the like, for administration to the subject (e.g., cattle) to be treated. For example, a pharmaceutical composition formulated for oral ingestion will contain a suitable carrier, for example, selected from sugars, starches, cellulose and its derivatives, malt, gelatine, talc, calcium sulphate, vegetable oils, synthetic oils, polyols, alginic acid, phosphate buffered solutions, emulsifiers, isotonic saline, and pyrogen-free water.

Pharmaceutical compositions suitable for use in the present invention include compositions wherein the active ingredients are contained in an effective amount to achieve its intended purpose. The dose of agent administered to a patient should be sufficient to elicit a beneficial response in the patient over time, such as a reduction in the symptoms associated with the condition. The quantity of the therapeutic/prophylactic agent(s) to be administered may depend on the subject to be treated inclusive of the age, sex, weight and general health condition thereof. In this regard, precise amounts of the therapeutic/prophylactic agent(s) for administration will depend on the judgement of the practitioner. In determining the effective amount of the agent to be administered in the treatment or prophylaxis of the condition, the physician may evaluate tissue levels of a polypeptide antigen, and progression of the disease or condition. In any event, those of skill in the art may readily determine suitable dosages of the therapeutic and/or prophylactic agents of the invention.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilisers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Such compositions may be prepared by any of the methods of pharmacy but all methods include the step of bringing into association one or more therapeutic agents as described above with the carrier which constitutes one or more necessary ingredients. In general, the pharmaceutical compositions of the present invention may be manufactured in a manner that is itself known, e.g., by means of conventional mixing, dissolving, granulating, dragee-making, levigating, emulsifying, encapsulating, entrapping or lyophilising processes.

Dosage forms of the therapeutic agents of the invention may also include injecting or implanting controlled releasing devices designed specifically for this purpose or other forms of implants modified to act additionally in this fashion. Controlled release of an agent of the invention may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, controlled release may be effected by using other polymer matrices, liposomes and/or microspheres.

Therapeutic agents of the invention may be provided as salts with pharmaceutically compatible counterions. Pharmaceutically compatible salts may be formed with many acids, including but not limited to hydrochloric, sulphuric, acetic, lactic, tartaric, malic, succinic, etc. Salts tend to be more soluble in aqueous or other protonic solvents that are the corresponding free base forms.

For any compound used in the method of the invention, the effective dose can be estimated initially from cell culture assays. For example, a dose can be formulated in animal models to achieve a circulating concentration range that includes the IC50 as determined in cell culture (e.g., the concentration of a test agent, which achieves a half-maximal reduction in target antigen). Such information can be used to more accurately determine useful doses in a mammal (e.g., cattle).

Toxicity and therapeutic efficacy of the compounds of the invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. The data obtained from these cell culture assays and animal studies can be used in formulating a range of dosage for use in the subject. The dosage of such compounds lies preferably within a range of circulating concentrations that include the ED50 with little or no toxicity. The dosage may vary within this range depending upon the dosage form employed and the route of administration utilised. The exact formulation, route of administration and dosage can be chosen by the individual physician in view of the subject's condition. (See for example Fingl et al., 1975, in "The Pharmacological Basis of Therapeutics", Ch. 1 p1).

Dosage amount and interval may be adjusted individually to provide plasma levels of the active compound(s) which are sufficient to maintain target antigen-reducing effects or effects that ameliorate the disease or condition. Usual patient dosages for systemic administration range from 1-2000 mg/day, commonly from 1-250 mg/day, and typically from 10-150 mg/day. Stated in terms of patient body weight, usual dosages range from 0.02-25 mg/kg/day, commonly from 0.02-3 mg/kg/day, typically from 0.2-1.5 mg/kg/day. Stated in terms of patient body surface areas, usual dosages range from 0.5-1200 mg/m$^2$/day, commonly from 0.5-150 mg/m$^2$/day, typically from 5-100 mg/m$^2$/day.

Alternately, one may administer the agent in a local rather than systemic manner, for example, via injection of the compound directly into a tissue, often in a depot or sustained release formulation. Furthermore, one may administer the agent in a targeted drug delivery system, for example, in a liposome coated with tissue-specific antibody. The liposomes will be targeted to and taken up selectively by the tissue.

From the foregoing, it will be appreciated that the agents of the invention may be used as therapeutic or prophylactic immunostimulating compositions or vaccines. Accordingly, the invention extends to the production of immunostimulating compositions containing as active compounds one or more of the therapeutic/prophylactic agents of the invention. Any suitable procedure is contemplated for producing such vaccines. Exemplary procedures include, for example, those described in NEW GENERATION VACCINES (1997, Levine et al., Marcel Dekker, Inc. New York, Basel Hong Kong).

Immunostimulating compositions according to the present invention can contain a physiologically acceptable diluent or excipient such as water, phosphate buffered saline and saline. They may also include an adjuvant as is well known in the art. Suitable adjuvants include, but are not limited to: surface active substances such as hexadecylamine, octadecylamine, octadecyl amino acid esters, lysolecithin, dimethyldioctadecylammonium bromide, N, N-dicoctadecyl-N', N'bis(2-hydroxyethyl-propanediamine), methoxyhexadecylglycerol, and pluronic polyols; polyamines such as pyran, dextransulfate, poly IC carbopol; peptides such as muramyl dipeptide and derivatives, dimethylglycine, tuftsin; oil emulsions; and mineral gels such as aluminum phosphate, aluminum hydroxide or alum; lymphokines, QuilA and immune stimulating complexes (ISCOMS).

Suitably, antigen-presenting cells contacted ex vivo with the polypeptide antigens of the invention, as well as antigen-specific T lymphocytes generated with these antigen-presenting cells can be used as active compounds in immunostimulating compositions for prophylactic or therapeutic applications. The primed cells, which are preferably mature dendritic cells, can be injected with the tick polypeptide by any method that elicits an immune response into a syngeneic animal (i.e., a cow). Preferably, antigen-presenting cells are injected back into the same animal from whom the source tissue/cells was obtained. The injection site may be subcutaneous, intraperitoneal, intramuscular, intradermal, or intravenous. The number of antigen-primed antigen-presenting cells reinjected back into the animal in need of treatment may vary depending on inter alia, the antigen and size of the individual. This number may range for example between about 10$^4$ and 10$^8$, and more preferably between about 10$^6$ and 10$^7$ antigen-primed antigen-presenting cells (e.g., dendritic cells). The antigen-presenting cells should be administered in a pharmaceutically acceptable carrier, which is non-toxic to the cells and the individual. Such carrier may be the growth medium in which the antigen-presenting cells were grown, or any suitable buffering medium such as phosphate buffered saline.

In one embodiment, the antigen-primed antigen-presenting cells of the invention could also be used for generating large numbers of CD4$^+$ CTL, for adoptive transfer to immunosuppressed individuals who are unable to mount normal immune responses. For example, antigen-specific CD4$^+$ CTL can be adoptively transferred for therapeutic purposes in subjects afflicted with a tick infestation.

The effectiveness of the immunization may be assessed using any suitable technique. For example, CTL lysis assays may be employed using stimulated splenocytes or peripheral blood mononuclear cells (PBMC) on peptide coated or recombinant virus infected cells using $^{51}$Cr labeled target cells. Such assays can be performed using for example any mammalian cells (Allen et al., 2000, *J. Immunol.* 164(9): 4968-4978; also Woodberry et al., infra). Alternatively, the efficacy of the immunization may be monitored using one or more techniques including, but not limited to, HLA class I tetramer staining—of both fresh and stimulated PBMCs (see for example Allen et al., supra), proliferation assays (Allen et al., supra), Elispot assays and intracellular cytokine staining (Allen et al., supra), Elisa assays for detecting linear B cell responses; and Western blots of cell sample expressing the synthetic polynucleotides. Particularly relevant will be the cytokine profile of T-cells activated by antigen, and more particularly the production and secretion of IFN-γ, IL-2, IL-4, IL-5, IL-10, TGF-β and TNF-α.

7. Antigen-Binding Molecules

The present invention also contemplates antigen-binding molecules that specifically bind to tick polypeptides of the present invention. Exemplary antigen-binding molecules for use in the practice of the present invention include monoclonal antibodies, Fv, Fab, Fab', and F(ab')$_2$ immunoglobulin fragments, as well as synthetic antibodies such as, but not limited to, single domain antibodies (DABs), synthetic stabilised Fv fragments (e.g., single chain Fv fragments (scFv), disulphide stabilized Fv fragments (dsFv), single variable region domains (dAbs), minibodies, combibodies, and multivalent antibodies such as diabodies and multi-scFv, or engineered equivalents. Techniques for preparing and using various antibody-based constructs and fragments are well known in the art. Means for preparing and characterising antibodies are also well known in the art. In illustrative examples, antibodies can be made by conventional immunization (e.g., polyclonal sera and hybridomas) with isolated, purified, or recombinant peptides or proteins corresponding to a tick polypeptide, or as recombinant fragments corresponding to a tick polypeptide, usually expressed in *Escherichia coli*, after selection from phage display or ribosome display libraries. Knowledge of the antigen-binding regions (e.g., complementarity-determining regions) of such antibodies can be used to prepare synthetic antibodies as described, for example, above.

Suitable monoclonal antibodies may be prepared by standard hybridoma methods, using differential binding assays to ensure that the antibodies are specific for a tick polypeptide, and do not show cross-reactivity. Alternatively, suitable monoclonal antibodies may be prepared using antibody engineering methods such as phage display. Methods for obtaining highly specific antibodies from antibody phage display libraries are known in the art, and several phage antibody libraries are commercially available from, for example MorphoSys (Martinsried, Germany), Cambridge Antibody Technology (Cambridge, UK), and Dyax (Cambridge, Mass.). Suitable phage display methods are described, for example, in U.S. Pat. Nos. 6,300,064 and 5,969,108, which are hereby incorporated by reference in their entirety. See also, for example, "*Antibody Engineering,*" McCafferty et al.)Eds.)(IRL Press, 1996) and references therein. Phage display antibody methods can use libraries of antibodies in the Fab or scFv format. Once the antibody heavy and light chain genes are recovered from the phage antibodies, antibodies in any suitable format may be prepared (e.g., whole antibodies, Fab, scFv, etc.).

7.1 Single Chain Variable Region Molecules

Exemplary fragments of this type include single chain Fv fragments (sFv, frequently termed scFv) in which a peptide linker is used to bridge the N terminus or C terminus of a $V_H$ domain with the C terminus or N terminus, respectively, of a $V_L$ domain. ScFv lack all constant parts of whole antibodies and are not able to activate complement. Suitable peptide linkers for joining the $V_H$ and $V_L$ domains are those which allow the $V_H$ and $V_L$ domains to fold into a single polypeptide chain having an antigen binding site with a three dimensional structure similar to that of the antigen binding site of a whole antibody from which the Fv fragment is derived. Linkers having the desired properties may be obtained by the method disclosed in U.S. Pat. No. 4,946,778. However, in some cases a linker is absent. ScFvs may be prepared, for example, in accordance with methods outlined in Kreber et al. (1997, *J. Immunol. Methods;* 201(1): 35-55). Alternatively, they may be prepared by methods described in U.S. Pat. No. 5,091,513, European Patent No. 239,400, or the articles by Winter and Milstein (1991, *Nature,* 349: 293) and Plückthun et al. (1996, *Antibody engineering: A practical approach.* 203-252).

In another embodiment, the synthetic stabilized Fv fragment comprises a disulfide stabilized Fv (dsFv) in which cysteine residues are introduced into the $V_H$ and $V_L$ domains such that in the fully folded Fv molecule the two residues will form a disulfide bond therebetween. Suitable methods of producing dsFv are described for example in (Glockscuther et al. *Biochem.* 29: 1363-1367; Reiter et al. 1994, *J. Biol. Chem.* 269: 18327-18331; Reiter et al. 1994, *Biochem.* 33: 5451-5459; Reiter et al. 1994. *Cancer Res.* 54: 2714-2718; Webber et al. 1995, *Mol. Immunol.* 32: 249-258).

Also contemplated as antigen-binding molecules are single variable region domains (termed dAbs) as for example disclosed in Ward et al. (1989, *Nature* 341: 544-546); Hamers-Casterman et al. (1993, *Nature.* 363: 446-448); Davies & Riechmann, (1994, *FEBS Lett.* 339: 285-290). Alternatively, the antigen-binding molecule may comprise a "minibody". In this regard, minibodies are small versions of whole antibodies, which encode in a single chain the essential elements of a whole antibody. Suitably, the minibody is comprised of the $V_H$ and $V_L$ domains of a native antibody fused to the hinge region and CH3 domain of the immunoglobulin molecule as, for example, disclosed in U.S. Pat. No. 5,837,821.

In an alternate embodiment, the antigen binding molecule may comprise non-immunoglobulin derived, protein frameworks. For example, reference may be made to Ku & Schultz, (1995, *Proc. Natl. Acad. Sci. USA,* 92: 652-6556) which discloses a four-helix bundle protein cytochrome b562 having two loops randomized to create complementarity determining regions (CDRs), which have been selected for antigen binding.

The antigen-binding molecule may be multivalent (i.e., having more than one antigen binding site). Such multivalent molecules may be specific for one or more antigens. Multivalent molecules of this type may be prepared by dimerisation of two antibody fragments through a cysteinyl-containing peptide as, for example disclosed by Adams et al., (1993, *Cancer Res.* 53: 4026-4034) and Cumber et al. (1992, *J. Immunol.* 149: 120-126). Alternatively, dimerisation may be facilitated by fusion of the antibody fragments to amphiphilic helices that naturally dimerise (Pack P. Plünckthun, 1992, *Biochem.* 31: 1579-1584), or by use of domains (such as the leucine zippers jun and fos) that preferentially heterodimerise (Kostelny et al., 1992, *J. Immunol.* 148: 1547-1553). In an alternate embodiment, the multivalent molecule may comprise a multivalent single chain antibody (multi-scFv) comprising at least two scFvs linked together by a peptide linker. In this regard, non-covalently or covalently linked scFv dimers termed "diabodies" may be used. Multi-scFvs may be bispecific or greater depending on the number of scFvs employed having different antigen binding specificities. Multi-scFvs may be prepared for example by methods disclosed in U.S. Pat. No. 5,892,020.

Phage display and combinatorial methods for generating natriuretic peptide antigen-binding molecules are known in the art (as described in, e.g., Ladner et al. U.S. Pat. No. 5,223,409; Kang et al. International Publication No. WO92/18619; Dower et al. International Publication No. WO91/17271; Winter et al. International Publication WO92/20791; Markland et al. International Publication No. WO 92/15679; Breitling et al.; International Publication WO 93/01288; McCafferty et al. International Publication No. WO92/01047; Garrard et al. International Publication No. WO 92/09690; Ladner et al. International Publication No. WO90/02809; Fuchs et al. (1991) *Biotechnology* 9: 1370-1372; Hay et al., 1992, *Hum Antibod Hybridomas* 3: 81-85; Huse et al., 1989, *Science* 246:1275-1281; Griffths et al., 1993, *EMBO J* 12: 725-734; Hawkins et al., 1992, *J Mol Biol* 226: 889-896; Clackson et al., 1991, *Nature* 352: 624-628; Gram et al., 1992, *Proc. Natl. Acad. Sci USA* 89: 3576-3580; Garrad et al., 1991, *Bio/Technology* 9: 1373-1377; Hoogenboom et al., 1991, *Nucleic Acid Res* 19: 4133-4137; and Barbas et al., 1991, *Proc. Natl. Acad. Sci USA* 88: 7978-7982).

Preferred epitopes encompassed by the antigenic peptide are regions of *Oxyuranus* natriuretic peptides which are located in the N-terminal, central core and especially C-terminal portions, as well as regions with high antigenicity. The antigen-binding molecule can be coupled to a compound, e.g., a label such as a radioactive nucleus, or imaging agent, e.g., a radioactive, enzymatic, or other, e.g., imaging agent, e.g., a NMR contrast agent. Labels which produce detectable radioactive emissions or fluorescence are preferred.

8. Methods for Assessing Immunostimulation

An animal's capacity to respond to a tick infestation (i.e., tick polypeptides) may be assessed by evaluating whether immune cells primed to attack such antigens are increased in number, activity, and ability to detect and destroy those antigens. Strength of immune response is measured by standard tests including: direct measurement of peripheral blood lymphocytes (including B lymphocytes) by means known to the art; natural killer cell cytotoxicity assays (see, e.g., Provinciali M. et al. (1992, *J. Immunol. Meth.* 155: 19-24), cell proliferation assays (see, e.g., Vollenweider, I. and Groseurth, P. J. (1992, *J. Immunol. Meth.* 149: 133-135), immunoassays of immune cells and subsets (see, e.g., Loeffler, D. A., et al. (1992, *Cytom.* 13: 169-174); Rivoltini, L., et al. (1992, *Cancer Immunol. Immunother.* 34: 241-251); or skin tests for cell-mediated immunity (see, e.g., Chang, A. E. et al (1993, *Cancer Res.* 53: 1043-1050).

It will be appreciated that successful immunostimulation using a tick vaccine as described herein, can be assessed by counting the number of ticks present on an animal following vaccination. Ticks may be collected, and incubated to determine their egg-laying capacity and the viability of the eggs to emerge into larvae. (Exemplary methods for performing these sorts of assessment are outlined in more detail in the Examples for example, by determining the effects of the vaccines on the total number of ticks (NET), weight of eggs (EW), and larval emergence (EC) etc, as described)). In other words, the skilled person will appreciate that following the provision of an immune-stimulating composition as described herein, the success of the vaccination/immunostimulation is to be assessed by determining a) the formation of an immune response, such as antibody formation in the host, and b) the subsequent repulsion of ticks from feeding (i.e., reduced attachment, and development of ticks).

9. Pharmaceutical Formulations

The compositions of the present invention are suitably pharmaceutical compositions. The pharmaceutical compositions often comprise one or more "pharmaceutically acceptable carriers." These include any carrier which does not itself induce the production of antibodies harmful to the individual receiving the composition. Suitable carriers typically are large, slowly metabolized macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. A composition may also contain a diluent, such as water, saline, glycerol, etc. Additionally, an auxiliary substance, such as a wetting or emulsifying agent, pH buffering substance, and the like, may be present. A thorough discussion of pharmaceutically acceptable components is available in Gennaro (2000) Remington: The Science and Practice of Pharmacy. 20th ed., ISBN: 0683306472.

The pharmaceutical compositions may include various salts, excipients, delivery vehicles and/or auxiliary agents as are disclosed, e.g., in U.S. patent application Publication No. 2002/0019358, published Feb. 14, 2002.

Certain compositions of the present invention can further include one or more adjuvants before, after, or concurrently with the polynucleotide. The term "adjuvant" refers to any material having the ability to (1) alter or increase the immune response to a particular antigen or (2) increase or aid an effect of a pharmacological agent. It should be noted, with respect to polynucleotide vaccines, that an "adjuvant," can be a transfection facilitating material. Similarly, certain "transfection facilitating materials" described supra, may also be an "adjuvant." An adjuvant maybe used with a composition comprising a polynucleotide of the present invention. In a prime-boost regimen, as described herein, an adjuvant may be used with either the priming immunization, the booster immunization, or both. Suitable adjuvants include, but are not limited to, cytokines and growth factors; bacterial components (e.g., endotoxins, in particular superantigens, exotoxins and cell wall components); aluminium-based salts; calcium-based salts; silica; polynucleotides; toxoids; serum proteins, viruses and virally-derived materials, poisons, venoms, imidazoquiniline compounds, poloxamers, and cationic lipids.

A great variety of materials have been shown to have adjuvant activity through a variety of mechanisms. Any compound which may increase the expression, antigenicity or immunogenicity of the polypeptide is a potential adjuvant. The present invention provides an assay to screen for improved immune responses to potential adjuvants. Potential adjuvants which may be screened for their ability to enhance the immune response according to the present invention include, but are not limited to: Montanide, inert carriers, such as alum, bentonite, latex, and acrylic particles; PLURONIC block polymers, such as TITERMAX (block copolymer CRL-8941, squalene (a metabolizable oil) and a microparticulate silica stabilizer); depot formers, such as Freund's adjuvant, surface active materials, such as saponin, lysolecithin, retinal, Quil A, liposomes, and PLURONIC polymer formulations; macrophage stimulators, such as bacterial lipopolysaccharide; alternate pathway complement activators, such as insulin, zymosan, endotoxin, and levamisole; and non-ionic surfactants, such as poloxamers, poly(oxyethylene)-poly(oxypropylene) tri-block copolymers. Also included as adjuvants are transfection-facilitating materials, such as those described above.

The Montanide adjuvants are based on purified squalene and squalene, emulsified with highly purified mannide mono-oleate. There are several types of Montanide, including ISA 50V, 51, 206, and 720. ISA 50V, 51 and 720 are water-in-oil (W/O) emulsions, which ISA 206 is a W/O-in-water emulsion. ISA 206 and 50V have are used solely in veterinary vaccine formulations. Emulsions of Montanide ISA51 and 720 are composed of metabolizable squalene-based oil with a mannide mono-oleate emulsifier.

Poloxamers which may be screened for their ability to enhance the immune response according to the present invention include, but are not limited to, commercially available poloxamers such as PLURONIC surfactants, which are block copolymers of propylene oxide and ethylene oxide in which the propylene oxide block is sandwiched between two ethylene oxide blocks. Examples of PLURONIC surfactants include PLURONIC L121 poloxamer (ave. MW: 4400; approx. MW of hydrophobe, 3600; approx. wt % of hydrophile, 10%), PLURONIC L101 poloxamer (ave. MW: 3800; approx. MW of hydrophobe, 3000; approx. wt. % of hydrophile, 10%), PLURONIC L81 poloxamer (ave. MW: 2750; approx. MW of hydrophobe, 2400; approx. wt. % of hydrophile, 10%), PLURONIC L61 poloxamer (ave. MW: 2000; approx. MW of hydrophobe, 1800; approx. wt. % of hydrophile, 10%), PLURONIC L31 poloxamer (ave. MW: 1100; approx. MW of hydrophobe, 900; approx. wt. % of hydrophile, 10%), PLURONIC L122 poloxamer (ave. MW: 5000; approx. MW of hydrophobe, 3600; approx. wt. % of hydrophile, 20%), PLURONIC L92 poloxamer (ave. MW: 3650; approx. MW of hydrophobe, 2700; approx. wt. % of hydrophile, 20%), PLURONIC L72 poloxamer (ave. MW: 2750; approx. MW of hydrophobe, 2100; approx. wt. % of hydrophile, 20%), PLURONIC L62 poloxamer (ave. MW: 2500; approx. MW of hydrophobe, 1800; approx. wt. % of hydrophile, 20%), PLURONIC L42 poloxamer (ave. MW: 1630; approx. MW of hydrophobe, 1200; approx. wt. % of hydrophile, 20%), PLURONIC L63 poloxamer (ave. MW: 2650; approx. MW of hydrophobe, 1800; approx. wt. % of hydrophile, 30%), PLURONIC L43 poloxamer (ave. MW: 1850; approx. MW of hydrophobe, 1200; approx. wt. % of hydrophile, 30%), PLURONIC L64 poloxamer (ave. MW: 2900; approx. MW of hydrophobe, 1800; approx. wt. % of hydrophile, 40%), PLURONIC L44 poloxamer (ave. MW: 2200; approx. MW of hydrophobe, 1200; approx. wt. % of hydrophile, 40%), PLURONIC L35 poloxamer (ave. MW: 1900; approx. MW of hydrophobe, 900; approx. wt. % of hydrophile, 50%), PLURONIC P123 poloxamer (ave. MW: 5750; approx. MW of hydrophobe, 3600; approx. wt. % of hydrophile, 30%), PLURONIC P103 poloxamer (ave. MW: 4950; approx. MW of hydrophobe, 3000; approx. wt. % of hydrophile, 30%), PLURONIC P104 poloxamer (ave. MW: 5900; approx. MW of hydrophobe, 3000; approx. wt. % of hydrophile, 40%), PLURONIC P84 poloxamer (ave. MW: 4200; approx. MW of hydrophobe, 2400; approx. wt. % of hydrophile, 40%), PLURONIC P105 poloxamer (ave. MW: 6500; approx. MW of hydrophobe, 3000; approx. wt. % of hydrophile, 50%), PLURONIC P85 poloxamer (ave. MW: 4600; approx. MW of hydrophobe, 2400; approx. wt. % of hydrophile, 50%), PLURONIC P75 poloxamer (ave. MW: 4150; approx. MW of hydrophobe, 2100; approx. wt. % of hydrophile, 50%), PLURONIC P65 poloxamer (ave. MW: 3400; approx. MW of hydrophobe, 1800; approx. wt. % of hydrophile, 50%), PLURONIC F127 poloxamer (ave. MW: 12600; approx. MW of hydrophobe, 3600; approx. wt. % of hydrophile, 70%), PLURONIC F98 poloxamer (ave. MW: 13000; approx. MW of hydrophobe, 2700; approx. wt. % of hydrophile, 80%), PLURONIC F87 poloxamer (ave. MW: 7700; approx. MW of hydrophobe, 2400; approx. wt. % of hydrophile, 70%), PLURONIC F77 poloxamer (ave. MW: 6600; approx. MW of hydrophobe, 2100; approx. wt. % of hydrophile, 70%), PLURONIC F108 poloxamer (ave. MW: 14600; approx. MW of hydrophobe, 3000; approx. wt. % of hydrophile, 80%), PLURONIC F98 poloxamer (ave. MW: 13000; approx. MW of hydrophobe, 2700; approx. wt. % of hydrophile, 80%), PLURONIC F88 poloxamer (ave. MW: 11400; approx. MW of hydrophobe, 2400; approx. wt. % of hydrophile, 80%), PLURONIC F68 poloxamer (ave. MW: 8400; approx. MW of hydrophobe, 1800; approx. wt. % of hydrophile, 80%), PLURONIC F38 poloxamer (ave. MW: 4700; approx. MW of hydrophobe, 900; approx. wt. % of hydrophile, 80%).

Reverse poloxamers which may be screened for their ability to enhance the immune response according to the present invention include, but are not limited to PLURONIC R 31 R1 reverse poloxamer (ave. MW: 3250; approx. MW of hydrophobe, 3100; approx. wt. % of hydrophile, 10%), PLURONIC R25R1 reverse poloxamer (ave. MW: 2700; approx. MW of hydrophobe, 2500; approx. wt. % of hydrophile, 10%), PLURONIC R 17R1 reverse poloxamer (ave. MW: 1900; approx. MW of hydrophobe, 1700; approx. wt. % of hydrophile, 10%), PLURONIC R 31R2 reverse poloxamer (ave. MW: 3300; approx. MW of hydrophobe, 3100; approx. wt. % of hydrophile, 20%), PLURONIC R 25R2 reverse poloxamer (ave. MW: 3100; approx. MW of hydrophobe, 2500; approx. wt. % of hydrophile, 20%), PLURONIC R 17R2 reverse poloxamer (ave. MW: 2150; approx. MW of hydrophobe, 1700; approx. wt. % of hydrophile, 20%), PLURONIC R 12R3 reverse poloxamer (ave. MW: 1800; approx. MW of hydrophobe, 1200; approx. wt. % of hydrophile, 30%), PLURONIC R 31R4 reverse poloxamer (ave. MW: 4150; approx. MW of hydrophobe, 3100; approx. wt. % of hydrophile, 40%), PLURONIC R 25R4 reverse poloxamer (ave. MW: 3600; approx. MW of hydrophobe, 2500; approx. wt. % of hydrophile, 40%), PLURONIC R 22R4 reverse poloxamer (ave. MW: 3350; approx. MW of hydrophobe, 2200; approx. wt. % of hydrophile, 40%), PLURONIC R17R4 reverse poloxamer (ave. MW: 3650; approx. MW of hydrophobe, 1700; approx. wt. % of hydrophile, 40%), PLURONIC R 25R5 reverse poloxamer (ave. MW: 4320; approx. MW of hydrophobe, 2500; approx. wt. % of hydrophile, 50%), PLURONIC R10R5 reverse poloxamer (ave. MW: 1950; approx. MW of hydrophobe, 1000; approx. wt. % of hydrophile, 50%), PLURONIC R 25R8 reverse poloxamer (ave. MW: 8550; approx. MW of hydrophobe, 2500; approx. wt. % of hydrophile, 80%), PLURONIC R 17R8 reverse poloxamer (ave. MW: 7000; approx. MW of hydrophobe, 1700; approx. wt. % of hydrophile, 80%), and PLURONIC R 10R8 reverse poloxamer (ave. MW: 4550; approx. MW of hydrophobe, 1000; approx. wt. % of hydrophile, 80%).

Other commercially available poloxamers which may be screened for their ability to enhance the immune response according to the present invention include compounds that are block copolymer of polyethylene and polypropylene glycol such as SYNPERONIC L121 (ave. MW: 4400), SYNPERONIC L122 (ave. MW: 5000), SYNPERONIC P104 (ave. MW: 5850), SYNPERONIC P105 (ave. MW: 6500), SYNPERONIC P123 (ave. MW: 5750), SYNPERONIC P85 (ave. MW: 4600) and SYNPERONIC P94 (ave. MW: 4600), in which L indicates that the surfactants are liquids, P that they are pastes, the first digit is a measure of the molecular weight of the polypropylene portion of the surfactant and the last digit of the number, multiplied by 10, gives the percent ethylene oxide content of the surfactant; and compounds that are nonylphenyl polyethylene glycol such as SYNPERONIC NP10 (nonylphenol ethoxylated surfactant—10% solution), SYNPERONIC NP30 (condensate of 1 mole of nonylphenol with 30 moles of ethylene oxide) and SYNPERONIC NP5 (condensate of 1 mole of nonylphenol with 5.5 moles of naphthalene oxide).

Other poloxamers which may be screened for their ability to enhance the immune response according to the present invention include: (a) a polyether block copolymer comprising an A-type segment and a B-type segment, wherein the A-type segment comprises a linear polymeric segment of relatively hydrophilic character, the repeating units of which contribute an average Hansch-Leo fragmental constant of about −0.4 or less and have molecular weight contributions between about 30 and about 500, wherein the B-type segment comprises a linear polymeric segment of relatively hydrophobic character, the repeating units of which contribute an average Hansch-Leo fragmental constant of about −0.4 or more and have molecular weight contributions between about 30 and about 500, wherein at least about 80% of the linkages joining the repeating units for each of the polymeric segments comprise an ether linkage; (b) a block copolymer having a polyether segment and a polycation segment, wherein the polyether segment comprises at least an A-type block, and the polycation segment comprises a plurality of cationic repeating units; and (c) a polyether-polycation copolymer comprising a polymer, a polyether segment and a polycationic segment comprising a plurality of cationic repeating units of formula —NH—R0, wherein R0 is a straight chain aliphatic group of 2 to 6 carbon atoms, which may be substituted, wherein said polyether segments comprise at least one of an A-type of B-type segment. See U.S. Pat. No. 5,656,611. Other poloxamers of interest include CRL1005 (12 kDa, 5% POE), CRL8300 (11 kDa, 5% POE), CRL2690 (12 kDa, 10% POE), CRL4505 (15 kDa, 5% POE) and CRL1415 (9 kDa, 10% POE).

Other auxiliary agents which may be screened for their ability to enhance the immune response according to the present invention include, but are not limited to, Acacia (gum arabic); the poloxyethylene ether R—O—(C2H4O) x-H (BRIJ), e.g., polyethylene glycol dodecyl ether (BRIJ 35, x=23), polyethylene glycol dodecyl ether (BRIJ 30, x=4), polyethylene glycol hexadecyl ether (BRIJ 52 x=2), polyethylene glycol hexadecyl ether (BRIJ 56, x=10), polyethylene glycol hexadecyl ether (BRIJ 58P, x=20), polyethylene glycol octadecyl ether (BRIJ 72, x=2), polyethylene glycol octadecyl ether (BRIJ 76, x=10), polyethylene glycol octadecyl ether (BRIJ® 78P, x=20), polyethylene glycol oleyl ether (BRIJ 92V, x=2), and polyoxyl 10 oleyl ether (BRIJ 97, x=10); poly-D-glucosamine (chitosan); chlorbutanol; cholesterol; diethanolamine; digitonin; dimethylsulfoxide (DMSO), ethylenediamine tetraacetic acid (EDTA); glyceryl monosterate; lanolin alcohols; mono- and di-glycerides; monoethanolamine; nonylphenol polyoxyethylene ether (NP-40); octylphenoxypolyethoxyethanol (NONIDET NP-40 from Amresco); ethyl phenol poly (ethylene glycol ether)n, n=I 1 (NONIDET P40 from Roche); octyl phenol ethylene oxide condensate with about 9 ethylene oxide units (NONIDET P40); IGEPAL CA 630 ((octyl phenoxy) polyethoxyethanol; structurally same as NONIDET NP-40); oleic acid; oleyl alcohol; polyethylene glycol 8000; polyoxyl 20 cetostearyl ether; polyoxyl 35 castor oil; polyoxyl 40 hydrogenated castor oil; polyoxyl 40 stearate; polyoxyethylene sorbitan monolaurate (polysorbate 20, or TWEEN-20; polyoxyethylene sorbitan monooleate (polysorbate 80, or TWEEN-80); propylene glycol diacetate; propylene glycol monstearate; protamine sulfate; proteolytic enzymes; sodium dodecyl sulfate (SDS); sodium monolaurate; sodium stearate; sorbitan derivatives (SPAN), e.g., sorbitan monopalmitate (SPAN 40), sorbitan monostearate (SPAN 60), sorbitan tristearate (SPAN 65), sorbitan monooleate (SPAN 80), and sorbitan trioleate (SPAN 85); 2,6,10,15,19,23-hexamethyl-2,6,10,14,18,22-tetracosahexaene (squalene); stachyose; stearic acid; sucrose; surfactin (lipopeptide antibiotic from *Bacillus subtilis*); dodecylpoly(ethyleneglycolether)9 (THESIT) MW 582.9; octyl phenol ethylene oxide condensate with about 9-10 ethylene oxide units (TRITON X-100); octyl phenol ethylene oxide condensate with about 7-8 ethylene oxide units (TRITON X-114); tris(2-hydroxyethyl)amine (trolamine); and emulsifying wax.

In certain adjuvant compositions, the adjuvant is a cytokine. A composition of the present invention can comprise one or more cytokines, chemokines, or compounds that induce the production of cytokines and chemokines, or a polynucleotide encoding one or more cytokines, chemokines, or compounds that induce the production of cytokines and chemokines. Examples include, but are not limited to, granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interleukin 15 (IL-15), interleukin 18 (IL-18), interferon alpha (IFNα), interferon beta (IFNβ), interferon gamma (IFNγ), interferon omega (IFNΩ), interferon tau (IFNτ), interferon gamma inducing factor I (IGIF), transforming growth factor beta (TGF-β), RANTES (regulated upon activation, normal T-cell expressed and presumably secreted), macrophage inflammatory proteins (e.g., MIP-1 alpha and M3P-1 beta), *Leishmania* elongation initiating factor (LEIF), and Flt-3 ligand.

In certain compositions of the present invention, the polynucleotide construct may be complexed with an adjuvant composition comprising (±)-N-(3-aminopropyl)-N,N-dimethyl-2,3-bis(syn-9-tetradeceneyloxy)-1-propanaminium bromide (GAP-DMORIE). The composition may also comprise one or more co-lipids, e.g., 1,2-dioleoyl-sn-glycero-3-phosphoethanolamine (DOPE), 1,2-diphytanoyl-sn-glycero-3-phosphoethanolamine (DPyPE), and/or 1,2-dimyristoyl-glycer-3-phosphoethanolamine (DMPE). An adjuvant composition comprising GAP-DMORIE and DPyPE at a 1:1 molar ratio is referred to herein as VAXFECTIN adjuvant. See, e.g., PCT Publication No. WO 00/57917.

In other embodiments, the polynucleotide itself may function as an adjuvant as is the case when the polynucleotides of the invention are derived, in whole or in part, from bacterial DNA. Bacterial DNA containing motifs of unmethylated CpG-dinucleotides (CpG-DNA) triggers innate immune cells in vertebrates through a pattern recognition receptor (including toll receptors such as TLR 9) and thus possesses potent immunostimulatory effects on macrophages, dendritic cells and B-lymphocytes. See, e.g., Wagner, H., Curr. Opin. Microbiol. 5:62-69 (2002); Jung, J. et al., J. Immunol. 169: 2368-73 (2002); see also Klinman, D. M. et al., Proc. Natl Acad. Sci. U.S.A. 93:2879-83 (1996). Methods of using unmethylated CpG-dinucleotides as adjuvants are described in, for example, U.S. Pat. Nos. 6,207,646, 6,406,705 and 6,429,199.

The ability of an adjuvant to increase the immune response to an antigen is typically manifested by a significant increase in immune-mediated protection. For example, an increase in humoral immunity is typically manifested by a significant increase in the titre of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th2 response into a primarily cellular, or Th1 response.

Nucleic acid molecules and/or polynucleotides of the present invention, e.g., plasmid DNA, mRNA, linear DNA or oligonucleotides, may be solubilized in any of various buffers. Suitable buffers include, for example, phosphate buffered saline (PBS), normal saline, Tris buffer, and sodium phosphate (e.g., 150 mM sodium phosphate). Insoluble polynucleotides may be solubilized in a weak acid or weak base, and then diluted to the desired volume with a buffer. The pH of the buffer may be adjusted as appropriate. In addition, a pharmaceutically acceptable additive can be used to provide an appropriate osmolarity. Such additives are within the purview of one skilled in the art. For aqueous compositions used in vivo, sterile pyrogen-free water can be used. Such formulations will contain an effective amount of a polynucleotide together with a suitable amount of an aqueous solution in order to prepare pharmaceutically acceptable compositions suitable for administration to a mammal (e.g., cattle).

Compositions of the present invention can be formulated according to known methods. Suitable preparation methods are described, for example, in Remington's Pharmaceutical Sciences, 16th Edition, A. Osol, ed., Mack Publishing Co., Easton, Pa. (1980), and Remington's Pharmaceutical Sciences, 19th Edition, A. R. Gennaro, ed., Mack Publishing Co., Easton, Pa. (1995). Although the composition may be administered as an aqueous solution, it can also be formulated as an emulsion, gel, solution, suspension, lyophilized form, or any other form known in the art. In addition, the composition may contain pharmaceutically acceptable additives including, for example, diluents, binders, stabilizers, and preservatives.

The following examples are included for purposes of illustration only and are not intended to limit the scope of the present invention, which is defined by the appended claims.

9.1 Dosage

The present invention is generally concerned with therapeutic and prophylactic compositions. The compositions will comprise an "effective amount" of the compositions defined herein, such that an amount of the antigen can be produced in vivo so that an immune response is generated in the individual to which it is administered. The exact amount necessary will vary depending on the subject being treated; the age and general condition of the subject to be treated; the capacity of the subject's immune system to synthesize antibodies; the degree of protection desired; the severity of the condition being treated; the particular antigen selected and its mode of administration, among other factors. An appropriate effective amount can be readily determined by one of skill in the art. Thus, an "effective amount" will fall in a relatively broad range that can be determined through routine trials.

Dosage treatment may be a single dose schedule or a multiple dose schedule. In some embodiments, a dose of between around 50 µg to around 5 mg or above is sufficient to induce an immune response to the composition. More specifically, a dose of between around 100 µg to around 1 mg may be used in the methods of the invention. Thus, the methods of the present invention include dosages of the compositions defined herein of around 50 µg, 100 µg, 150 µg, 200 µg, 250 µg, 300 µg, 350 µg, 400 µg, 450 µg, 500 µg, 600 µg, 650 µg, 700 µg, 750 µg, 800 µg, 850 µg, 900 µg, 950 µg, 1 mg, or more, in order to treat a tick infestation.

The compositions of the present invention can be suitably formulated for injection. The composition may be prepared in unit dosage form in ampules, or in multidose containers. The polynucleotides may be present in such forms as suspensions, solutions, or emulsions in oily or preferably aqueous vehicles. Alternatively, the polynucleotide salt may be in lyophilized form for reconstitution, at the time of delivery, with a suitable vehicle, such as sterile pyrogen-free water. Both liquid as well as lyophilized forms that are to be reconstituted will comprise agents, preferably buffers, in amounts necessary to suitably adjust the pH of the injected solution. For any parenteral use, particularly if the formulation is to be administered intravenously, the total concentration of solutes should be controlled to make the preparation isotonic, hypotonic, or weakly hypertonic. Nonionic materials, such as sugars, are preferred for adjusting tonicity, and sucrose is particularly preferred. Any of these forms may further comprise suitable formulatory agents, such as starch or sugar, glycerol or saline. The compositions per unit dosage, whether liquid or solid, may contain from 0.1% to 99% of polynucleotide material.

The units dosage ampules or multidose containers, in which the polynucleotides are packaged prior to use, may comprise an hermetically sealed container enclosing an amount of polynucleotide or solution containing a polynucleotide suitable for a pharmaceutically effective dose thereof, or multiples of an effective dose. The polynucleotide is packaged as a sterile formulation, and the hermetically sealed container is designed to preserve sterility of the formulation until use.

The dosage to be administered depends to a large extent on the condition and size of the subject being treated as well as the frequency of treatment and the route of administration. Regimens for continuing therapy, including dose and frequency may be guided by the initial response and clinical judgment. The parenteral route of injection into the interstitial space of tissues is preferred, although other parenteral routes, such as inhalation of an aerosol formulation, may be required in specific administration, as for example to the mucous membranes of the nose, throat, bronchial tissues or lungs.

9.2 Routes of Administration

Once formulated, the compositions of the invention can be administered directly to the subject (e.g., as described above), for example, intradermally, intravenously, subcutaneously, orally, or other conventional methods for providing immune-stimulating compositions to an individual in need.

The compositions of the invention may be used for stimulating an immune response to a tick polypeptide in a subject that is immunologically naïve to the tick polypeptide or that has previously raised an immune response to that tick polypeptide. Thus, the present invention extends to methods for enhancing an immune response in a subject by administering to the subject the compositions or vaccines of the invention. Desirably, the immune response is both a cell-mediated immune response (e.g., a B-cell mediated response, which desirably includes $CD4^+$ T helper cells) and a humoral immune response (e.g., an antibody response).

Also encapsulated by the present invention is a method for treatment and/or prophylaxis of a tick infestation, comprising administering to a patient in need of such treatment an effective amount of a at least one polypeptide antigen that corresponds to a tick polypeptide, or a polynucleotide from which the polypeptide antigen is expressible, In yet another aspect, the invention provides a method for reducing the risk of transmission of a tick in a subject comprising administering to the subject an effective amount of a at least one polypeptide antigen that corresponds to a tick polypeptide, or a polynucleotide from which the polypeptide antigen is expressible, wherein the at least one tick polypeptide.

Ticks are vectors of a number of diseases and disorders, some of which can be debilitating or life-threatening. Exemplary pathogens transmitted by ticks include, but are not limited to, *Anaplasma* spp. (e.g., *Anaplasma marginale*), *Babesia* spp. (e.g., *B. bovis* and *B. bigemina*), *Borrelia* spp., *Theileria* spp. (e.g., *T. parva*) and viruses within the tick-borne encephalitis complex. Accordingly, the pathogen can cause a disease or disorder in the subject including, but not limited to cattle tick fever, East Coast Fever, babesiosis, tick-borne Encephalitis, anaplasmosis, or Lyme Disease. Thus, the invention also provides a method for the prevention of cattle tick fever, East Coast Fever, babesiosis, tick-borne Encephalitis, anaplasmosis, or Lyme Disease in a subject, the method comprising administering to the subject an effective amount of a at least one polypeptide antigen that corresponds to a tick polypeptide, or a polynucleotide from which the polypeptide antigen is expressible, wherein the at least one tick polypeptide is selected from a polypeptide comprising the amino acid sequence as set forth in SEQ ID NOs: 1, 3 and 4 and as described above and elsewhere herein, and thereby preventing cattle tick fever, East Coast Fever, babesiosis, tick-borne Encephalitis, anaplasmosis, or Lyme Disease in the subject.

After a subject is determined to be at risk of cattle tick fever, East Coast Fever, babesiosis, tick-borne Encephalitis, anaplasmosis, or Lyme Disease, it may be desirable to treat the subject with a therapeutic or prophylactic agent for the treatment of these diseases. Doxycycline, Amoxicillin, or Atovaquone plus Azithromycin are some examples of suitable treatments.

In some embodiments, the immunostimulatory composition is administered to a subject on a monthly basis. Alternatively, the immunostimulatory composition is administered 1, 2, 3, 4, 5, 6, 7, 8, 9, 10, 11 or more times a year.

In some embodiments, the composition comprises a nucleic acid construct from which a polypeptide antigen as described above is expressible. Administration of such nucleic acid constructs to a mammal (for example, cattle), may include delivery via direct oral intake, systemic injection, or delivery to selected tissue(s) or cells. Delivery of the nucleic acid constructs to cells or tissues of the mammal may be facilitated by microprojectile bombardment, liposome mediated transfection (e.g., Lipofectin or Lipofectamine), electroporation, calcium phosphate or DEAE-dextran-mediated transfection, for example. A detailed discussion of suitable delivery methods may be found in Chapter 9 of Ausubel et al., (1994-1998, supra). For example, in some embodiments the nucleic acid constructs are administered through intradermal injection.

The step of introducing the expression vector into the selected target cell or tissue will differ depending on the intended use and species, and can involve one or more of non-viral and viral vectors, cationic liposomes, retroviruses, and adenoviruses such as, for example, described in Mulligan, R. C., (1993). The skilled person will be familiar with suitable methods for doing so.

9.3 Prime-Boost Regimens

The methods of the invention may comprise (i) administering a priming composition of at least one polypeptide antigen or a polynucleotide sequence from which a nucleotide sequence encoding at least one polypeptide antigen is expressible, wherein the polypeptide antigens are those described above and elsewhere herein, and (ii) subsequently administering a later booster composition of at least one polypeptide antigen or a polynucleotide sequence from which a nucleotide sequence encoding a at least one polypeptide antigen is expressible.

For example, the booster composition may be administered at least 7, 14, 21 or 28 days, at least 1, 2, 3, 4, 5, or 6 months, or at least 1, 2, 3, 4, or 5 years after the priming composition. The priming and booster compositions may be administered by the same route or they may be administered via different routes. For example, the priming and booster doses may both be administered intradermally. One advantage of intradermal administration for DNA vaccines is that this route has a higher frequency of dendritic cells and other antigen presenting cells than some other routes (e.g., the intramuscular route). As the efficacy of administration is at least partially dependent on uptake, processing and presentation of the immunogen by dendritic cells, which may be enhanced by administering through this route.

The booster composition may be administered one or several times at the same or different dosages. It is within the ability of one of ordinary skill in the art to optimize prime-boost combinations, including optimization of the timing and dose of administration.

10. Methods of Treatment

Also encapsulated by the present invention is a method for treatment and/or prophylaxis of a tick infestation, comprising administering to a mammal (e.g., cattle) in need of such treatment an effective amount of a composition as broadly described above and elsewhere herein.

In one embodiment, the cell or composition of the invention can also be used for generating large numbers of CD4$^+$ CTL. For example, antigen-specific CD4$^+$ CTL can be adoptively transferred for therapeutic purposes in mammals (e.g., cattle) afflicted with a tick infestation.

In accordance with the present invention, it is proposed that cells and compositions that include a polypeptide antigen that corresponds to a M1-2A Clone 91 tick polypeptide find utility in the treatment or prophylaxis of a tick infestation. The compositions of the present invention may be used therapeutically after a tick infestation is diagnosed, or may be used prophylactically before the mammal carries a tick.

When the compositions described above and elsewhere herein are used in prophylactic methods against tick infestations, such methods are suitably prime-boost vaccinations against a tick polypeptide that induce long-lasting humoral, cell-mediated and mucosal immune responses against the tick polypeptide.

In some embodiments the cells and compositions of the present invention are administered in multiple doses in a prime-boost regimen, with the goal of inducing long-lived potent immunity against a tick polypeptide. Such strategies use a second dose of the composition to bolster immunity elicited by the priming dose.

Some embodiments of the present invention are based on the realisation that an optimal strategy for eliciting therapeutic and protective immunity against a tick polypeptide involves the generation of both a cellular and a humoral immune response to the tick polypeptide. The invention thus provides a multi-component administration strategy in which a first dose of the composition of the present invention primes the immune system by eliciting or inducing a first immune response, and a second dose of the composition of the present invention is used to boost or elicit a second immune response, wherein the composition administered in the first dose is the same as that administered second dose. In illustrative examples of this type, the first dose is administered to induce largely a cellular immune response to the target antigen, whereas the second dose is administered largely to elicit a humoral immune response to the target antigen. Upon completion of the administration steps of the strategy, both cellular and humoral immune responses develop to the target antigen. The two responses together thus provide effective or enhanced protection against a tick infestation or disease and/or condition that is transmitted by or otherwise associated with a tick.

In order to maximize the direct stimulation and activation of those CD4$^+$ CTLs that target the relevant M1-2A Clone 91 tick polypeptide(s), the compositions used for the prime administration and the boost administration are, preferentially, the same.

11. Kits

The present invention also provides kits comprising an immunostimulatory composition as broadly described above and elsewhere herein. Such kits may additionally comprise alternative immunogenic agents for concurrent use with the immunostimulatory compositions of the invention.

In some embodiments, in addition to the immunostimulatory compositions of the present invention the kits may include suitable components for performing the prime-boost regimens described above. For example, the kit may include separately housed priming and boosting doses of the at least one polypeptide antigens.

The kits may comprise additional components to assist in performing the methods of the present invention such as, for example, administration device(s), buffer(s), and/or diluent(s). The kits may also include containers for housing the various components and instructions for using the kit components in the methods of the present invention.

In order that the invention may be readily understood and put into practical effect, particular preferred embodiments will now be described by way of the following non-limiting examples.

EXAMPLES

Example 1 Antigen Discovery Using Subtraction Libraries

Methods & Materials

Subtraction library (suppressive subtractive hybridization, SSH) experiments were undertaken to isolate novel tick genes associated with different tick stages including: frustrated larvae (sensing a host in a mesh bag), attached feeding larvae, frustrated adult females (sensing a host in a mesh bag), feeding adult females, and adult male ticks. Methods were published see Lew-Tabor et al 2010. Isolated clones were sequenced and subsequently analysed to determine function and to predict membrane or secretory characteristics ie. signal peptides, transmembrane domains, metabolic pathways/KEGG, and Gene Ontology ("GO") terms. The sequences were also further categorized by Blastx sequence analyses against the following datasets: NCBI, COG (Tatusov et al., 2003, BMC Bioinformatics 4:41), String (von Mering et al., 2006 Nucleic Acids Res 35:D358-36), The Kyoto Encyclopedia of Genes and Genomes (KEGG) (Okuda et al., 2008 Nucleic Acids Res 36: W423-6), R. microplus Gene Index (Guerrero et al. 2005 Insect Biochem Mol Biol. 35:585-95; Wang et al. 2007 BMC Genomics 8: 368-382), NCBI conserved domain database (CDD) (Marchler-Bauer et al., 2009 Nucleic Acids Res 37:D205-10), and non-redundant protein database (nr) using the Centre for Comparative Genomics (CCG) HPC resource. Trans-membrane domain searches were conducted using S-TMHMM (Krogh et al., 2001) and protein localization using SignalP (Bendtsen et al., 2004) to reconfirm earlier analyses.

Results

The five SSH libraries resulted in 511 clones which assembled into 36 contigs and 90 singletons from differentially expressed transcripts from unattached frustrated larvae (L3) (95), feeding larvae (L2) (159), unattached frustrated (F3) adult females (68), feeding adult females (F2) (95) and male (M1) adult ticks (94 clones) (Lew-Tabor et al. 2010). Sequence analysis based on BLAST, Panther, KOG and domain (CDD) analyses assigned functional groups for proteins including: cuticle proteins, enzymes, ligand binding, molecular chaperones, nucleic acid binding (ribosomal proteins), putative salivary proteins, serine proteases, stress response (heat shock, glycine rich) and transporters. An additional 63% of all contigs and singletons were novel R. microplus (R. australis) transcripts or predicted proteins of unknown function. Twelve sequences were chosen for further analysis as potential vaccine candidates including: F2-3-A clone54, M1-2-A clone10, L3-3-A clone59, L3-3ACONTIG2, M1-2-Aclone91, F1-2AClone75; F2-3-A clone60; F2-3-Aclone78; L3-3Aclone15.5; L3-3Aclone33.3; M1-2AClone24; M1-3-AClone17. The selected candidates were either secreted or membrane bound proteins with known annotations, with several also predicted to be potential 'concealed antigens' (not secreted and internal to cell—not exposed) with unknown annotations or as hypothetical proteins (Summarised in Table 6).

TABLE 6

Bioinformatics analyses of twelve transcripts selected from differentially expressed sequences

| Transcript | Annotation | Signal P | TMHMM prediction |
|---|---|---|---|
| F2-3-A clone 54 | Serine protease | Signal peptide | Inner, trans, outer |
| M1-2-A clone 10 | Serine protease | Non-secretory | Inner, trans, outer |
| L3-3-A clone 59 | Cysteine protease | Signal peptide | Inner, trans, outer |
| L3-3A contig2 | Glycine rich protein | Non-secretory | Inner membrane |
| M1-2-A clone 91 | Putative cation transporter | Non-secretory | Inner membrane |
| F1-2-A clone 75 | Unknown | Signal peptide | Inner, trans, outer |
| F2-3-A clone 60 | Unknown | Non-secretory | Inner membrane |
| F2-3-A clone 78 | Unknown | Non-secretory | Inner membrane |
| L3-3-A clone 15.5 | Unknown | Signal peptide | Inner membrane |
| L3-3-A clone 33.3 | Unknown | Non-secretory | Inner membrane |
| M1-2-A clone 24 | Unknown | Non-secretory | Inner membrane |
| M1-3-A clone 17 | Unknown | Signal peptide | Inner membrane |

Example 2: In Vitro Laboratory Screening

Materials & Methods qRT-PCR localization. Methods were described in Lew-Tabor et al 2010.

B cell epitope predictions and anti-peptide invitro tick feeding. Linear B cell epitopes (peptides) with minimum length of 10 amino acids were selected using Bepipred (Larsen et al., 2006 Immunome Res 2:2) at a threshold greater than 0.35. Biotinylated peptides were synthesized by Mimotopes Pty. Ltd. (Australia) and screened using ELISA streptavidin plates using sera pooled from tick exposed resistant and susceptible cattle. Peptides were dissolved in 1 mL of 40% Acetonitrile/Water solution, or if acetonitrile is unavailable, using pure water and 10 µl of dissolved peptide was mixed with 990 µL of PBS/TWEEN-20. The biotinylated peptide solutions were then used without further dilution for capture onto the coated streptavidin or avidin plates. After peptide capture, the general assay procedure recommended by Mimotope was followed, sera collected from susceptible and resistant cattle (source of cattle, see Piper et al. 2017) were pooled and diluted ⅟10 to be added into each well. Negative control was pooled sera collected from tick naïve cattle. Rabbit IgG Anti Cow conjugate was diluted ⅟4000 Negative and positive peptides were provided by Mimotope as internal controls of the assay. A peptide was considered positive with an average of 1.5 D.O 450 nm higher than the negative control.

Peptides recognized by resistant sera were used to prepare sheep antisera (Mimotopes Pty Ltd Australia) for in vitro screening (tick feeding) as described in Lew-Tabor et al 2014. Tube feeding was set up immediately following tick collection (tick colony at QASP) using ~19/20 day old semi-engorged females. Ten ticks per treatment including serum control (no anti-tick antibodies) with approximately 6-7 treatments were set up per tick feeding experiment (including controls). Ticks were each microscopically examined for 'intact' mouthparts, pre-weighed prior to artificial feeding, followed by positioning of tubes and overnight feeding. Following successful feeding, ticks were weighed and placed in individual tubes to monitor egg output (3 weeks). Final egg weight was determined per treatment and eggs were left to hatch to determine % larval emergence (2-3 weeks). Serum from a TickGARD vaccinated animal (Bm86) was used as a control positive treatment for antibody feeding in sheep serum and dsRNA from TC6372 was used as the control for gene knockdown feeding experiments in bovine serum. Efficacy (%) of a particular antibody treatment was calculated as a simple ratio of the average measurement between treated (t) and control (c) ticks:

$$\text{Efficacy}(\%) = 100 \times \left[1 - \left(\frac{ace\ t}{ace\ c}\right)\left(\frac{apeh\ t}{apeh\ c}\right)\right]$$

'ace' is the average of the cumulative egg output per tick and 'apeh' is the average of the percentage of eggs hatching into larvae (Lew-Tabor et al 2014).

Results qRT-PCR localisations for each differentially expressed transcript is summarized in Table 7.

TABLE 7

Localisation (qRT-PCR) of differentially expressed transcripts across all stages and adult female organs collected from tick susceptible cattle with frustrated larvae (FL) and feeding females (FF) collected from resistant cattle (final column)

| Transcript | FL | Nymph | Male | Female gut | Female salivary gland | Female ovary | Frustrated whole female | Whole female feeding | Ticks from resistant cattle |
|---|---|---|---|---|---|---|---|---|---|
| F2-3-A clone 54 | | | | | | X | | | |
| M1-2-A clone 10 | | | | X | | | | | FF |
| L3-3-A clone 59 | X | X | | | X | | X | | |
| L3-3A contig2 | X | X | | X | X | | | | |
| M1-2-A clone 91 | | | | X | | | X | | |
| F1-2-A clone 75 | | X | | | | | | X | |
| F2-3-A clone 60 | | | | | | | X | | |
| F2-3-A clone 78 | X | X | | X | | | X | | |
| L3-3-A clone 15.5 | X | X | X | X | X | X | X | | |
| L3-3-A clone 33.3 | X | X | | X | | | X | | |
| M1-2-A clone 24 | X | X | X | | | | | | |
| M1-3-A clone 17 | | | X | | | | | | |

Effectivity of a particular antibody treatment was calculated relative to the control treatments as described in the equation above. Although mouth parts were microscopically examined, there were a small percentage of ticks which still did not feed in all treatments and controls. In control treatments, 2-3 ticks (out of 10) would sometimes not feed and in some instances with some treatments very few ticks feed. To determine if the latter was an effect of the actual treatment these were repeated (at least twice) to increase the validity of the observation and to determine if the failure to feed was indeed due to the antibody treatment. Effectivity is a measure of average weight, egg output and larval emergence relative to the control fed ticks. A summary of antibody treatment effectivities is presented in Table 8.

TABLE 8

B cell epitope predictions, ELISA recognition and in vitro feeding efficacies (ND = not done)

| Transcript | B cell epitope | ELISA recognition | In vitro tick feeding efficacies and description of effect |
|---|---|---|---|
| F2-3-A clone 54 | (not screened due to limited qRT-PCR localisation) | | |
| M1-2-A clone 10 | yes | Resistant sera | 12%, some unviable eggs |
| L3-3-A clone 59 | yes | Susceptible and resistant sera | 13-20% |
| L3-3A contig2 | yes | Susceptible sera | ND |
| M1-2-A clone 91 | yes | [1]Susceptible and resistant sera | [2]99%, poor feeding and nil/deformed unviable eggs |
| F1-2-A clone 75 | yes | negative | ND |
| F2-3-A clone 60 | No | ND | ND |
| F2-3-A clone 78 | no | ND | ND |
| L3-3-A clone 15.5 | yes | Negative | ND |
| L3-3-A clone 33.3 | yes | Negative | ND |
| M1-2-A clone 24 | yes | negative | ND |
| M1-3-A clone 17 | yes | negative | ND |

[1]Five B cell epitopes (peptides) with 3 recognised by tick susceptible sera, and 2 recognised by tick resistant sera (SEQ ID No. 3 and 4)
[2]SEQ ID No. 3 was used to produce sheep antibodies for in vitro feeding testing The candidate with particularly strong efficacy, M1-2A Clone 91 tick polypeptide, was selected cattle tick challenge trials.

Example 3 In Vivo Tick Challenge Trials

Materials and Methods

Peptides

Peptides and/or recombinant proteins produced in E. coli (Genscript, USA) were prepared and tested. The peptides were synthesised by Mimotopes (Melbourne, Australia) and conjugated to Keyhole Limpet Hemocyanin (KLH) carrier protein via a standard linker to the peptide incorporating an N-terminal cysteine amino acid residue. The KLH conjugate was used for the experiments herein as the carrier protein for the peptides is known to recruit T helper cells (see, Yang et al., 2001 Chapter 12 In: Ellis, R. W. (Ed.), New Vaccine Technologies. Medical Intelligence Unit, Eurekah.com/Landes Bioscience, Georgetown, Tex., USA, pp 214-26.). The logic for targeting the B-cell epitope is based on the damage that host antibodies can elicit on feeding ticks.

Vaccination and Antibody Screening

Each trial included an un-vaccinated group injected with adjuvant mixed with PBS (randomly allocated as vaccination group numbers). Mimotope KLH conjugated peptide was provided as a lyophilised powder (1 mg/tube) and re-suspension in PBS required 3×30 s rounds of sonication. The adjuvants and peptides (PBS only for controls) were mixed using a homogeniser for 1 min (LabGen 700, Cole Palmer) to ensure suspension of the vaccine mixtures. Cattle were vaccinated on Day 0 with 200 μg per peptide/100 μg recombinant protein using Freund's Complete adjuvant (1:1) in a total volume of 1 ml. On Days 28 and 49, cattle were re-vaccinated using Freund's Incomplete adjuvant (1:1) in a total volume of 2 ml. Blood samples were collected from each steer prior to each vaccination, and the sera obtained were labelled V0 (Day 0), V1 (Day 28), and V2 (Day 48). Blood was also collected prior to larval infestation and was labelled V3 (Day 63). After completion of the tick infestation, within the week a final serum sample was collected (V4) to see if antibody levels changed following tick challenge. Cattle were monitored after each vaccination for reactions to the adjuvants used. When elevated temperatures were observed, the cattle were treated with Ketoprofen as appropriate (non-steroidal pain relief).

Animals from each experimental group were screened by ELISA for the production of peptide specific IgG antibodies. The serum samples used were those prepared from blood collected prior to vaccination (naïve, V0) compared to those collected after each vaccination as well as following tick infestation (V1, V2, V3 and V4). The ELISA was conducted using 96 well flat bottomed polystyrene plates (cat #M2963-100, Sigma Aldrich) which were coated with 100 ng of un-conjugated peptides per well dissolved in a 1 ng/μl solution of 0.1 M carbonate buffer (pH 9.6) and incubated overnight at 4° C. Plates were washed twice with 200 μl wash solution per well (WS: 1×PBS+0.1% Tween 20) and blocked with 200 μl of Blocking Solution (BS:1×PBS+1% BSA+1% skim milk powder). Plates were incubated at room temperature (RT) for 1 hr, shaking gently and washed 3 times with WS. Serial two-fold dilutions of sera were prepared in duplicate from 1/100 to endpoint using PBS. Plates were incubated with 100 μl of diluted sera for 1 hr with gentle shaking at RT followed by 3 washes with WS. Rabbit anti-Bovine IgG conjugated with Horse Radish Peroxidase (Sigma Catalogue #A5295) was diluted 1:1000 in WS and used as the secondary antibody. A total of 100 μl per well was added to each plate and incubated at RT for 1 hr with shaking. Plates were washed 3 times with WS and developed using the TMB Liquid Substrate System (cat #T0440-100, Sigma Aldrich) as described by the manufacturer. Briefly, 100 μl of the TMB substrate was added to each well and incubated for 10 mins in the dark. The reaction was stopped by adding 100 μl/well of 1M phosphoric acid. The absorbance was read at 450 nm using an EPOCH Microplate reader (Biotek Instruments, Millenium Science). Animals from each group were screened against respective peptide(s) used during the immunisation of the group. The average titre was normalised to pooled pre-vaccinated sera titres.

Infestation, Tick Collections, Assessment of Efficacy of Vaccinations and Statistics After the third vaccination, cattle were separated into tick moat individual pens to acclimatise prior to tick infestations. These pens (PC1 facility, QASP UQ Gatton campus) are located in a temperature controlled building, 10 m2 raised mesh floors, sealed walls, feed bins and automatic waterers. Two weeks later (day 63), cattle were infested with 2,500 larvae twice 2 days apart (total 5,000 larvae). Nineteen days after tick infestation, ticks were collected daily to collect data for total tick numbers (per animal per day) and total tick weights prior to the incubation of a subset of 50 ticks for egg production assessments. Ticks were incubated at the Qld Bioscience Precinct DAF/QAAFI laboratory (UQ St. Lucia campus) in a humidified incubator (Thermoline) at 27° C. and 85% relative humidity. After eggs were weighed, subsets of 0.25 g of eggs were incubated to determine the percent larval emergence (egg viability/fertility). Larvae were examined to determine percentage larval emergence by freezing the samples to enable the counting of the number of larvae emerged and eggs which did not hatch.

The most recent review of tick trial efficacy analysis (Cunha et al., 2013) follows on from the methods previously described by Fragoso et al. (1998) and de la Fuente et al. (1999). Cunha et al. (2013) define efficacy as:

Efficacy (%)=100×[1−(NET×EW×EC)], where

NET=the ratio of the average total tick numbers (vaccinated group/control group), EW=the ratio of the average weight of eggs (g) per number of ticks incubated (vaccinated group/control group), and EC=the ratio of the percent larval emergence (vaccinated group/control group).

In these trials, all ticks collected were not incubated to determine fertility. Hence EW and EC were estimated on a subset of 250 ticks incubated per animal.

The effects of the vaccines on the total number of ticks (NET), weight of eggs (EW), and larval emergence (EC) were tested for statistical significance by ANOVA, with each variable being log 10-transformed before analysis to stabilise variance. Pair-wise differences between vaccine means were tested using the protected LSD test. The partial percentage efficacies for NET, EW and EC were calculated as:

Efficacy %=100(1−10**(Vaccine mean−Control mean))

These mean differences (for each measure, on the log 10-scale) were then summed to give the overall efficacy for each vaccine, giving the same values as the ratio-based formula of Cunha et al. (2013) above. The standard error for the overall efficacy was calculated from the standard errors of each partial efficacy, using the standard statistical formulae (Goodman, 1960). This calculation then allows a direct t-test of the overall efficacy against zero, for each vaccine.

Results

Antibody titres to the M1-2A Clone 91 polypeptide (bacteria-produced recombinant protein) increased or remained elevated following each vaccination. Following tick challenge antibody titres in animals were further increased or remained elevated in groups that were vaccinated with the M1-2A clone 91 (data not shown). Specifically, the M1-2A Clone 91 polypeptide had average efficacies of 45% (as KLH conjugated peptide comprising SEQ ID. NO. 3) and 66% (as full recombinant protein SEQ ID. No. 1) as well as resulting in around fewer ticks, smaller ticks, and reduced egg viability. This result indicates a 'strong effect' of this immunisation.

TABLE 9

| Antigen | Efficacy calculation |
| --- | --- |
| rM1-2A Clone 91 (bacteria full recombinant protein; SEQ ID NO: 1) | 66% |
| M1-2A Clone 91 (KLH-SEQ ID NO: 3) | 45% |

In summary, M1-2A Clone 91, which was isolated from a subtraction library as described above, demonstrates a significant capacity to generate an immune response in an animal to a tick. Surprisingly, ticks have a 99% death rate when fed antibodies to the M1-2A Clone 91 tick polypeptide RSAEGPSGSNR (data above; SEQ ID NO: 3) Particularly, the antibody-fed ticks died before laying eggs.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

BIBLIOGRAPHY deCastro, J. J., Sustainable tick and tickborne disease control in livestock improvement in developing countries, *Vet. Parasitol.*, 1997 71: 71-97.

Playford M, Rabiee A R, Lean I J, Ritchie M: Review of research needs for cattle tick control, Phases I and II. In.: Meat & Livestock Australia Ltd., Locked Bag 991, North Sydney NSW 2059; 2005: ISBN 1 74036 74685 74039.

Rand et al., Cloning and expression of a protective antigen from the cattle tick *Boophilus microplus*, *Proc. Natl. Acad. Sci.* USA, 1989, 86: 9657-9661.

Garcia-Garcia et al., Sequence variations in the *Boophilus microplus* Bm86 locus and implications for immunoprotection in cattle vaccinated with this antigen, *Exp. App. Acar.* 1999, 23: 883-895.

Cunha, et al., Calculation of the efficacy of vaccines against tick infestations on cattle, *Rev. Bras. Parasitol. Vet.*, 2013, 22 (4).

de la Fuente, et al., Vaccination against ticks (*Boophilus* spp.): the experience with the Bm86-based vaccine Gavac, *Genet. Anal.*, 1999, 15: 143-148.

Lew-Tabor A. E., Moolhuijzen, P. M., Vance, M. E., Kurscheid, S., Rodriguez Valle M., Jarrett S., Minchin C. M., Jackson, L. A., Jonsson, N. N., Bellgard M. I., and Guerrero F. D. (2010) Suppressive subtractive hybridization analysis of *Rhipicephalus* (*Boophilus*) *microplus* transcript expression during feeding and attachment. Veterinary Parasitology 167 (2-4): 304-320.

Lew-Tabor, A. E., Bruyeres, A. G., Zhang, B., Rodriguez Valle, M. (2014) *Rhipicephalus* (*Boophilus*) *microplus* tick in vitro feeding methods for functional (dsRNA) and vaccine candidate (antibody) screening. Ticks and Tick Borne Diseases, 5:500-510.

Lew-Tabor, A. E. and Rodriguez Valle, M. (2016) A review of reverse vaccinology approaches for the development of vaccines against ticks and tick borne diseases. Ticks & Tick Borne Diseases 7:573-585

Piper, E., Jonsson, N., Gondro, C., Vance, M., Lew-Tabor, A., Jackson, L. (2017) Peripheral cellular and humoral responses to infestation with *Rhipicephalus microplus* in Santa-Gertrudis cattle. Parasite Immunology 39: e12402.

It will be understood that the invention disclosed and defined in this specification extends to all alternative combinations of two or more of the individual features mentioned or evident from the text or drawings. All of these different combinations constitute various alternative aspects of the invention.

---

The invention claimed is:

1. A composition comprising:
   a recombinant, isolated or synthetic polypeptide comprising or consisting of the amino acid sequence as set forth in SEQ ID NO: 3 (RSAEGPSGSNR); and
   an adjuvant for potentiating an immune response to the polypeptide.

2. The composition according to claim 1, wherein the recombinant, isolated or synthetic polypeptide is conjugated to a carrier protein.

3. The composition according to claim 1, wherein the recombinant, isolated or synthetic polypeptide is conjugated to Keyhole Limpet Hemocyanin.

4. The composition according to claim 1, wherein the composition comprises a further polypeptide that comprises or consists of the amino acid sequence of any one of: SEQ ID NOs: 5, and 24 to 32.

5. The composition according to claim 1, wherein the composition comprises a further polypeptide comprising or consisting of the amino acid sequence of any one of SEQ ID NOs: 5, and 24 to 32, conjugated to the polypeptide.

6. The composition according to claim 1, wherein the composition further comprises one or more promiscuous T-cell epitopes.

7. The composition according to claim 1, wherein the polypeptide is conjugated to the promiscuous T-cell epitope by a linker.

8. The composition according to claim 1, further comprising a pharmaceutically acceptable carrier, excipient or diluent.

9. The composition according to claim 1, wherein the adjuvant is selected from Freund's complete adjuvant, Freund's incomplete adjuvant, a saponin-derived adjuvant or an adjuvant comprising a mineral oil.

10. A method of forming an immune response in a subject to a tick or for treating or preventing or reducing the severity of a tick infestation, or for reducing the risk of transmission of a tick infestation in a subject, the method comprising administering to a subject in need thereof, a composition comprising a recombinant, isolated or synthetic polypeptide comprising or consisting of the amino acid sequence set forth in SEQ ID NO: 3 (RSAEGPSGSNR) and an adjuvant for potentiating an immune response to the tick.

11. The method according to claim 10, wherein the composition is administered to the subject intradermally.

12. The method according to claim 10, wherein the composition is administered to the subject on at least one, two or three separate occasions.

13. The method according to claim 10, wherein the subject is selected from the group consisting of: cattle, deer, antelope, sheep, buffalo, horses, rhinoceroses, peccaries, pigs, giraffes, okapi, pronghorn, ox, antelopes, camels, llamas, chevrotains, hippopotamuses, tapirs, zebras or a companion animal.

14. The method according to claim 10, wherein the subject is cattle.

15. The method according to claim 10, wherein the method comprises administering a further composition comprising at least one additional polypeptide for forming an immune response in the subject to a tick, wherein the additional polypeptide comprises an amino acid sequence corresponding to a polypeptide derived from a tick.

16. The composition of claim 1, wherein the recombinant, isolated or synthetic polypeptide further comprises the amino acid sequence set forth in SEQ ID NO: 4.

17. The composition of claim 1, wherein the recombinant, isolated or synthetic polypeptide comprises or consists of the amino acid sequence set forth in SEQ ID NO: 1, or an amino acid sequence that is at least 80% identical to the sequence set forth in SEQ ID NO: 1.

18. The composition of claim 1, wherein the recombinant, isolated or synthetic polypeptide consists of the amino acid sequence set forth in SEQ ID NO: 1.

19. The method of claim 10, wherein the recombinant, isolated or synthetic polypeptide further comprises the amino acid sequence set forth in SEQ ID NO: 4.

20. The method of claim 10, wherein the recombinant, isolated or synthetic polypeptide comprises or consists of the amino acid sequence set forth in SEQ ID NO: 1, or an amino acid sequence that is at least 80% identical to the sequence set forth in SEQ ID NO: 1.

21. The method of claim 10, wherein the recombinant, isolated or synthetic polypeptide consists of the amino acid sequence set forth in SEQ ID NO: 1.

22. The method according to claim 20, wherein the composition is administered to the subject intradermally.

23. The method according to claim 20, wherein the subject is cattle.

* * * * *

SEQUENCE LISTING

<160> NUMBER OF SEQ ID NOS: 32

<210> SEQ ID NO 1
<211> LENGTH: 185
<212> TYPE: PRT
<213> ORGANISM: Rhipicephalus microplus

<400> SEQUENCE: 1

```
Met Ala Pro Asn Ala Pro Ala Lys Pro Asp Ala Met Trp Val Phe Gly
1               5                   10                  15

Tyr Gly Ser Leu Met Trp Lys Ala Asp Phe Pro Tyr Asn Arg Lys Leu
            20                  25                  30

Val Gly Tyr Val Lys Gly Tyr Val Arg Arg Phe Trp Gln Ala Ser Glu
        35                  40                  45

Asp His Arg Gly Val Pro Gly Lys Pro Gly Arg Val Val Thr Leu Val
    50                  55                  60

Pro Ser Thr Asp Gln Asn Asp Cys Val Trp Gly Val Ala Tyr Glu Ile
65                  70                  75                  80

Pro Glu Gly Glu Lys Asp Asp Val Ile Gly Arg Leu Asp Phe Arg Glu
                85                  90                  95
```

```
Lys Asp Gly Tyr Asp Arg Val Gln Val Thr Phe Tyr Pro Gly Lys Ser
            100                 105                 110

Glu Glu Lys Pro Phe Pro Leu Thr Ile Tyr Val Ala Gln Lys Glu Asn
            115                 120                 125

Pro Phe Tyr Leu Gly Pro Ala Asn Ala Leu Asp Ile Ala Arg Gln Ile
            130                 135                 140

Arg Ser Ala Glu Gly Pro Ser Gly Ser Asn Arg Glu Tyr Leu Leu Ser
145                 150                 155                 160

Leu Ile Glu Cys Met Arg Asn Ile Ala Pro His Val Pro Arg Pro Ala
                165                 170                 175

Leu Asp Gly Asn Arg Ala Lys Pro Ala
            180                 185

<210> SEQ ID NO 2
<211> LENGTH: 522
<212> TYPE: DNA
<213> ORGANISM: Rhipicephalus microplus

<400> SEQUENCE: 2
atgtgggtat tggatatgg gtcactaatg tggaaagctg attttcccta taatcgtaag       60
ctggttggct atgtgaaagg ctatgtgcgt cgtttctggc aggcgagcga ggaccaccgt      120
ggtgtgccgg gtaagccggg tcgtgtggtt accctggttc cgagcaccga ccaaaacgat      180
tgcgtgtggg gcgttgcgta cgagatcccg gagggcgaaa aggacgatgt gattggtcgt      240
ctggatttcc gtgaaaaaga cggctacgat cgtgtgcagg ttaccttcta tccgggtaag      300
agcgaggaaa aaccgtttcc gctgaccatc tacgttgcgc agaaagagaa cccgttttat      360
ctgggtccgg cgaacgcgct ggacatcgcg cgtcaaattc gtagcgcgga aggcccgagc      420
ggtagcaacc gtgagtatct gctgagcctg attgaatgca tgcgtaatat cgcgccgcat      480
gttccgcgtc cggcgctgga tggcaatcgt gcgaaaccgg cg                         522

<210> SEQ ID NO 3
<211> LENGTH: 11
<212> TYPE: PRT
<213> ORGANISM: Rhipicephalus microplus

<400> SEQUENCE: 3

Arg Ser Ala Glu Gly Pro Ser Gly Ser Asn Arg
1               5                   10

<210> SEQ ID NO 4
<211> LENGTH: 16
<212> TYPE: PRT
<213> ORGANISM: Rhipicephalus microplus

<400> SEQUENCE: 4

Pro His Val Pro Arg Pro Ala Leu Asp Gly Asn Arg Ala Lys Pro Ala
1               5                   10                  15

<210> SEQ ID NO 5
<211> LENGTH: 660
<212> TYPE: PRT
<213> ORGANISM: Rhipicephalus microplus

<400> SEQUENCE: 5

Met Ala Ala Arg Ser Gly Ser Ser Ala Ala Asp Arg Phe Val Ala Val
1               5                   10                  15

Ala Leu Leu Ala Thr Ala Leu Tyr Ala Thr Ala Ala Ala Asp Asn Phe
```

```
                20                  25                  30
Asp Thr Tyr Leu Ala Thr Leu Ser Asn Val Ser Ala Leu Ile Lys Asp
                35                  40                  45
Glu Ala Met Gly Val Ala Phe Ile Glu Gly Leu Asn Asp Pro Tyr Thr
                50                  55                  60
Thr Ile Asn Asn Val Asp Ser Ser Ser Trp Asp Tyr Ala Ser Asn
 65                  70                  75                  80
Ile Thr Asp Tyr Asn Gln Asn Met Ser Asn Lys Val Ser Thr Glu Val
                    85                  90                  95
Ser Lys Met Glu Arg Gln Phe Gly Ile Thr Ala Lys Arg Phe Asp Trp
                100                 105                 110
His Asn Phe Lys Asn Asp Ser Leu Lys Arg Leu Phe Arg His Val Ala
                115                 120                 125
Thr Ile Gly Leu Ala Ala Leu Pro Asp Asp Lys Leu Glu Asn Ala Thr
                130                 135                 140
Ser Leu Ser Ser Lys Met Ala Ala Ile Tyr Gly Ser Thr Lys Val Thr
145                 150                 155                 160
Val Gly Lys Asp Lys Asp Leu Pro Leu Glu Pro Asp Leu Thr Arg Asn
                165                 170                 175
Met Lys Glu Val Gly Asn Tyr Asp Lys Leu Leu Gln Thr Trp Leu Ala
                180                 185                 190
Trp His Asn Ala Val Gly Pro Ala Ile Lys Gln Tyr Tyr Ile Pro Tyr
                195                 200                 205
Ile Lys Leu Ser Asn Glu Ala Ala Ser Leu Asp Gly Tyr Asp Asn Ile
                210                 215                 220
Lys Ser Ala Trp Leu Ser Asp Tyr Glu Thr Glu Asn Met Thr Glu Ile
225                 230                 235                 240
Val Asp Lys Leu Trp Glu Asp Leu Ser Pro Leu Tyr Lys Lys Leu His
                245                 250                 255
Ala Tyr Val Arg Met Lys Leu Arg Glu Ile Tyr Pro Gly Arg Leu Pro
                260                 265                 270
Glu Asp Gly Thr Ile Pro Ala His Leu Leu Gly Asn Met Trp Ala Gln
                275                 280                 285
Glu Trp Gly Thr Leu Tyr Pro His Leu Thr Met Glu Asp Lys Pro Leu
                290                 295                 300
Asp Ile Ser Lys Thr Met Val Glu Gln Lys Trp Asp Ala Gln Lys Met
305                 310                 315                 320
Phe His Ala Ala Glu Asp Phe Phe Thr Ser Leu Gly Leu Asp Asn Met
                325                 330                 335
Thr Ser Glu Phe Trp Ser Lys Ser Ile Leu Thr Lys Pro Glu Asp Arg
                340                 345                 350
Glu Ile Gln Cys His Ala Ser Ala Trp Asn Met Tyr Asn Gly Asp Asp
                355                 360                 365
Phe Arg Ile Lys Met Cys Thr Asp Pro Ser Val Glu Glu Leu Arg Thr
                370                 375                 380
Val His His Glu Met Gly His Ile Glu Tyr Tyr Met Gln Tyr Lys His
385                 390                 395                 400
Leu His Val Leu Gln Glu Gly Ala Asn Glu Gly Phe His Glu Ala
                405                 410                 415
Val Gly Asp Leu Ile Ala Leu Ser Val Ala Thr Lys Thr His Tyr Gly
                420                 425                 430
Lys Leu Ser Leu Leu Lys Pro Thr Asp Lys Tyr Asn Ala Val Asp Leu
                435                 440                 445
```

```
Leu Leu Met Ser Ala Leu Asp Lys Ile Ala Phe Leu Pro Phe Gly Tyr
    450                 455                 460

Leu Leu Asp Lys Trp Arg Trp Thr Ile Phe Thr Gly Glu Thr Pro Phe
465                 470                 475                 480

Asp Lys Met Asn Glu Lys Phe Trp Glu Tyr Arg Ile Lys Tyr Gln Gly
                485                 490                 495

Val Ser Pro Pro Val Lys Arg Asn Glu Ser Phe Phe Asp Gly Gly Ala
            500                 505                 510

Lys Tyr His Val Ala Leu His Val Pro Tyr Leu Arg Tyr Phe Val Ala
        515                 520                 525

Phe Ile Leu Gln Phe Gln Phe His Glu His Leu Cys Thr Val Ala Lys
    530                 535                 540

Lys Val Asp Glu His His Pro Phe His Glu Cys Asp Ile Tyr Gly Glu
545                 550                 555                 560

Lys Asn Ala Gly Asp Val Leu Lys Lys Gly Leu Ser Leu Gly Arg Ser
                565                 570                 575

Lys Pro Trp Pro Asp Val Leu Glu Ile Met Ala Gly Thr Arg Gln Met
            580                 585                 590

Ser Ala Ser Ser Leu Lys Lys Tyr Tyr Glu Pro Leu Glu Lys Trp Leu
        595                 600                 605

Asp Glu Arg Ile Lys Asn Glu Val Val Gly Trp Asp Lys Ala Asn Val
    610                 615                 620

Gln Asp Tyr Met Gly Val Pro Ser Phe Ala Asn Lys Val Asp Phe Ser
625                 630                 635                 640

Ala Ala Ala Val Leu Ala Ser Ile Gly Val Ile Leu Phe Cys Trp Lys
                645                 650                 655

Asn Ile Ser Leu
            660

<210> SEQ ID NO 6
<211> LENGTH: 3408
<212> TYPE: PRT
<213> ORGANISM: Megathura crenulata

<400> SEQUENCE: 6

Met Leu Ser Val Arg Leu Leu Ile Val Val Leu Ala Leu Ala Asn Ala
1               5                   10                  15

Glu Asn Leu Val Arg Lys Ser Val Glu His Leu Thr Gln Glu Glu Thr
                20                  25                  30

Leu Asp Leu Gln Ala Ala Leu Arg Glu Leu Gln Met Asp Ser Ser Ser
            35                  40                  45

Ile Gly Phe Gln Lys Ile Ala Ala Ala His Gly Ala Pro Ala Ser Cys
        50                  55                  60

Val His Lys Asp Thr Ser Ile Ala Cys Cys Ile His Gly Met Pro Thr
65                  70                  75                  80

Phe Pro His Trp His Arg Ala Tyr Val Val His Met Glu Arg Ala Leu
                85                  90                  95

Gln Thr Lys Arg Arg Thr Ser Gly Leu Pro Tyr Trp Asp Trp Thr Glu
                100                 105                 110

Pro Ile Thr Gln Leu Pro Ser Leu Ala Ala Asp Pro Val Tyr Ile Asp
            115                 120                 125

Ser Gln Gly Gly Lys Ala His Thr Asn Tyr Trp Tyr Arg Gly Asn Ile
        130                 135                 140

Asp Phe Leu Asp Lys Lys Thr Asn Arg Ala Val Asp Asp Arg Leu Phe
```

```
            145                 150                 155                 160
Glu Lys Val Lys Pro Gly Gln His Thr His Leu Met Glu Ser Val Leu
                    165                 170                 175

Asp Ala Leu Glu Gln Asp Glu Phe Cys Lys Phe Glu Ile Gln Phe Glu
            180                 185                 190

Leu Ala His Asn Ala Ile His Tyr Leu Val Gly Gly Lys His Asp Tyr
                195                 200                 205

Ser Met Ala Asn Leu Glu Tyr Thr Ala Tyr Asp Pro Ile Phe Phe Leu
    210                 215                 220

His His Ser Asn Val Asp Arg Ile Phe Ala Ile Trp Gln Arg Leu Gln
225                 230                 235                 240

Glu Leu Arg Asn Lys Asp Pro Lys Ala Met Asp Cys Ala Gln Glu Leu
                245                 250                 255

Leu His Gln Lys Met Glu Pro Phe Ser Trp Glu Asp Asn Asp Ile Pro
            260                 265                 270

Leu Thr Asn Asp Tyr Asp Thr Leu Asn Leu Asn Gly Met Thr Pro Glu
        275                 280                 285

Glu Leu Lys Thr Tyr Leu Asp Glu Arg Ser Ser Arg Ala Arg Ala Phe
    290                 295                 300

Ala Ser Phe Arg Leu Lys Gly Phe Gly Gly Ser Ala Asn Val Phe Val
305                 310                 315                 320

Tyr Val Cys Ile Pro Asp Asp Asn Asp Arg Asn Asp Asp His Cys Glu
                325                 330                 335

Lys Ala Gly Asp Phe Phe Val Leu Gly Gly Pro Ser Glu Met Lys Trp
            340                 345                 350

Gln Phe Tyr Arg Pro Tyr Leu Phe Asp Leu Ser Asp Thr Val His Lys
        355                 360                 365

Met Gly Met Lys Leu Asp Gly His Tyr Thr Val Lys Ala Glu Leu Phe
    370                 375                 380

Ser Val Asn Gly Thr Ala Leu Pro Asp Asp Leu Leu Pro His Pro Val
385                 390                 395                 400

Val Val His His Pro Glu Lys Gly Phe Thr Asp Pro Val Lys His
                405                 410                 415

His Gln Ser Ala Asn Leu Leu Val Arg Lys Asn Ile Asn Asp Leu Thr
            420                 425                 430

Arg Glu Glu Val Leu Asn Leu Arg Glu Ala Phe His Lys Phe Gln Glu
        435                 440                 445

Asp Arg Ser Val Asp Gly Tyr Gln Ala Thr Ala Glu Tyr His Gly Leu
    450                 455                 460

Pro Ala Arg Cys Pro Arg Pro Asp Ala Lys Asp Arg Tyr Ala Cys Cys
465                 470                 475                 480

Val His Gly Met Pro Ile Phe Pro His Trp His Arg Leu Phe Val Thr
                485                 490                 495

Gln Val Glu Asp Ala Leu Val Gly Arg Gly Ala Thr Ile Gly Ile Pro
            500                 505                 510

Tyr Trp Gly Leu Pro Tyr Trp Asp Trp Thr Glu Pro Met Thr His Ile
        515                 520                 525

Pro Gly Leu Ala Gly Asn Lys Thr Tyr Val Asp Ser His Gly Ala Ser
    530                 535                 540

His Thr Asn Pro Phe His Ser Ser Val Ile Ala Phe Glu Glu Asn Ala
545                 550                 555                 560

Pro His Thr Lys Arg Gln Ile Asp Gln Arg Leu Phe Lys Pro Ala Thr
                565                 570                 575
```

```
Phe Gly His His Thr Asp Leu Phe Asn Gln Ile Leu Tyr Ala Phe Glu
            580                 585                 590

Gln Glu Asp Tyr Cys Asp Phe Glu Val Gln Phe Glu Ile Thr His Asn
        595                 600                 605

Thr Ile His Ala Trp Thr Gly Gly Ser Glu His Phe Ser Met Ser Ser
610                 615                 620

Leu His Tyr Thr Ala Phe Asp Pro Leu Phe Tyr Phe His His Ser Asn
625                 630                 635                 640

Val Asp Arg Leu Trp Ala Val Trp Gln Ala Leu Gln Met Arg Arg His
                645                 650                 655

Lys Pro Tyr Arg Ala His Cys Ala Ile Ser Leu Glu His Met His Leu
            660                 665                 670

Lys Pro Phe Ala Phe Ser Ser Pro Leu Asn Asn Asn Glu Lys Thr His
        675                 680                 685

Ala Asn Ala Met Pro Asn Lys Ile Tyr Asp Tyr Glu Asn Val Leu His
    690                 695                 700

Tyr Thr Tyr Glu Asp Leu Thr Phe Gly Gly Ile Ser Leu Glu Asn Ile
705                 710                 715                 720

Glu Lys Met Ile His Glu Asn Gln Gln Glu Asp Arg Ile Tyr Ala Gly
                725                 730                 735

Phe Leu Leu Ala Gly Ile Arg Thr Ser Ala Asn Val Asp Ile Phe Ile
            740                 745                 750

Lys Thr Thr Asp Ser Val Gln His Lys Ala Gly Thr Phe Ala Val Leu
        755                 760                 765

Gly Gly Ser Lys Glu Met Lys Trp Gly Phe Asp Arg Val Phe Lys Phe
    770                 775                 780

Asp Ile Thr His Val Leu Lys Asp Leu Asp Leu Thr Ala Asp Gly Asp
785                 790                 795                 800

Phe Glu Val Thr Val Asp Ile Thr Glu Val Asp Gly Thr Lys Leu Ala
                805                 810                 815

Ser Ser Leu Ile Pro His Ala Ser Val Ile Arg Glu His Ala Arg Gly
            820                 825                 830

Lys Leu Asn Arg Val Lys Phe Asp Lys Val Pro Arg Ser Arg Leu Ile
        835                 840                 845

Arg Lys Asn Val Asp Arg Leu Ser Pro Glu Glu Met Asn Glu Leu Arg
    850                 855                 860

Lys Ala Leu Ala Leu Leu Lys Glu Asp Lys Ser Ala Gly Gly Phe Gln
865                 870                 875                 880

Gln Leu Gly Ala Phe His Gly Glu Pro Lys Trp Cys Pro Ser Pro Glu
                885                 890                 895

Ala Ser Lys Lys Phe Ala Cys Cys Val His Gly Met Ser Val Phe Pro
            900                 905                 910

His Trp His Arg Leu Leu Thr Val Gln Ser Glu Asn Ala Leu Arg Arg
        915                 920                 925

His Gly Tyr Asp Gly Ala Leu Pro Tyr Trp Asp Trp Thr Ser Pro Leu
    930                 935                 940

Asn His Leu Pro Glu Leu Ala Asp His Glu Lys Tyr Val Asp Pro Glu
945                 950                 955                 960

Asp Gly Val Glu Lys His Asn Pro Trp Phe Asp Gly His Ile Asp Thr
                965                 970                 975

Val Asp Lys Thr Thr Thr Arg Ser Val Gln Asn Lys Leu Phe Glu Gln
            980                 985                 990
```

```
Pro Glu Phe Gly His Tyr Thr Ser Ile Ala Lys Gln Val Leu Leu Ala
            995                 1000                1005

Leu Glu Gln Asp Asn Phe Cys Asp Phe Glu Ile Gln Tyr Glu Ile
    1010                1015                1020

Ala His Asn Tyr Ile His Ala Leu Val Gly Gly Ala Gln Pro Tyr
    1025                1030                1035

Gly Met Ala Ser Leu Arg Tyr Thr Ala Phe Asp Pro Leu Phe Tyr
    1040                1045                1050

Leu His His Ser Asn Thr Asp Arg Ile Trp Ala Ile Trp Gln Ala
    1055                1060                1065

Leu Gln Lys Tyr Arg Gly Lys Pro Tyr Asn Val Ala Asn Cys Ala
    1070                1075                1080

Val Thr Ser Met Arg Glu Pro Leu Gln Pro Phe Gly Leu Ser Ala
    1085                1090                1095

Asn Ile Asn Thr Asp His Val Thr Lys Glu His Ser Val Pro Phe
    1100                1105                1110

Asn Val Phe Asp Tyr Lys Thr Asn Phe Asn Tyr Glu Tyr Asp Thr
    1115                1120                1125

Leu Glu Phe Asn Gly Leu Ser Ile Ser Gln Leu Asn Lys Lys Leu
    1130                1135                1140

Glu Ala Ile Lys Ser Gln Asp Arg Phe Ala Gly Phe Leu Leu
    1145                1150                1155

Ser Gly Phe Lys Lys Ser Ser Leu Val Lys Phe Asn Ile Cys Thr
    1160                1165                1170

Asp Ser Ser Asn Cys His Pro Ala Gly Glu Phe Tyr Leu Leu Gly
    1175                1180                1185

Asp Glu Asn Glu Met Pro Trp Ala Tyr Asp Arg Val Phe Lys Tyr
    1190                1195                1200

Asp Ile Thr Glu Lys Leu His Asp Leu Lys Leu His Ala Glu Asp
    1205                1210                1215

His Phe Tyr Ile Asp Tyr Glu Val Phe Asp Leu Lys Pro Ala Ser
    1220                1225                1230

Leu Gly Lys Asp Leu Phe Lys Gln Pro Ser Val Ile His Glu Pro
    1235                1240                1245

Arg Ile Gly His His Glu Gly Glu Val Tyr Gln Ala Glu Val Thr
    1250                1255                1260

Ser Ala Asn Arg Ile Arg Lys Asn Ile Glu Asn Leu Ser Leu Gly
    1265                1270                1275

Glu Leu Glu Ser Leu Arg Ala Ala Phe Leu Glu Ile Glu Asn Asp
    1280                1285                1290

Gly Thr Tyr Glu Ser Ile Ala Lys Phe His Gly Ser Pro Gly Leu
    1295                1300                1305

Cys Gln Leu Asn Gly Asn Pro Ile Ser Cys Cys Val His Gly Met
    1310                1315                1320

Pro Thr Phe Pro His Trp His Arg Leu Tyr Val Val Val Val Glu
    1325                1330                1335

Asn Ala Leu Leu Lys Lys Gly Ser Ser Val Ala Val Pro Tyr Trp
    1340                1345                1350

Asp Trp Thr Lys Arg Ile Glu His Leu Pro His Leu Ile Ser Asp
    1355                1360                1365

Ala Thr Tyr Tyr Asn Ser Arg Gln His His Tyr Glu Thr Asn Pro
    1370                1375                1380

Phe His His Gly Lys Ile Thr His Glu Asn Glu Ile Thr Thr Arg
```

-continued

```
                1385                1390                1395
Asp Pro Lys Asp Ser Leu Phe His Ser Asp Tyr Phe Tyr Glu Gln
        1400                1405                1410
Val Leu Tyr Ala Leu Glu Gln Asp Asn Phe Cys Asp Phe Glu Ile
        1415                1420                1425
Gln Leu Glu Ile Leu His Asn Ala Leu His Ser Leu Leu Gly Gly
        1430                1435                1440
Lys Gly Lys Tyr Ser Met Ser Asn Leu Asp Tyr Ala Ala Phe Asp
        1445                1450                1455
Pro Val Phe Phe Leu His His Ala Thr Thr Asp Arg Ile Trp Ala
        1460                1465                1470
Ile Trp Gln Asp Leu Gln Arg Phe Arg Lys Arg Pro Tyr Arg Glu
        1475                1480                1485
Ala Asn Cys Ala Ile Gln Leu Met His Thr Pro Leu Gln Pro Phe
        1490                1495                1500
Asp Lys Ser Asp Asn Asn Asp Glu Ala Thr Lys Thr His Ala Thr
        1505                1510                1515
Pro His Asp Gly Phe Glu Tyr Gln Asn Ser Phe Gly Tyr Ala Tyr
        1520                1525                1530
Asp Asn Leu Glu Leu Asn His Tyr Ser Ile Pro Gln Leu Asp His
        1535                1540                1545
Met Leu Gln Glu Arg Lys Arg His Asp Arg Val Phe Ala Gly Phe
        1550                1555                1560
Leu Leu His Asn Ile Gly Thr Ser Ala Asp Gly His Val Phe Val
        1565                1570                1575
Cys Leu Pro Thr Gly Glu His Thr Lys Asp Cys Ser His Glu Ala
        1580                1585                1590
Gly Met Phe Ser Ile Leu Gly Gly Gln Thr Glu Met Ser Phe Val
        1595                1600                1605
Phe Asp Arg Leu Tyr Lys Leu Asp Ile Thr Lys Ala Leu Lys Lys
        1610                1615                1620
Asn Gly Val His Leu Gln Gly Asp Phe Asp Leu Glu Ile Glu Ile
        1625                1630                1635
Thr Ala Val Asn Gly Ser His Leu Asp Ser His Val Ile His Ser
        1640                1645                1650
Pro Thr Ile Leu Phe Glu Ala Gly Thr Asp Ser Ala His Thr Asp
        1655                1660                1665
Asp Gly His Thr Glu Pro Val Met Ile Arg Lys Asp Ile Thr Gln
        1670                1675                1680
Leu Asp Lys Arg Gln Gln Leu Ser Leu Val Lys Ala Leu Glu Ser
        1685                1690                1695
Met Lys Ala Asp His Ser Ser Asp Gly Phe Gln Ala Ile Ala Ser
        1700                1705                1710
Phe His Ala Leu Pro Pro Leu Cys Pro Ser Pro Ala Ala Ser Lys
        1715                1720                1725
Arg Phe Ala Cys Cys Val His Gly Met Ala Thr Phe Pro Gln Trp
        1730                1735                1740
His Arg Leu Tyr Thr Val Gln Phe Gln Asp Ser Leu Arg Lys His
        1745                1750                1755
Gly Ala Val Val Gly Leu Pro Tyr Trp Asp Trp Thr Leu Pro Arg
        1760                1765                1770
Ser Glu Leu Pro Glu Leu Leu Thr Val Ser Thr Ile His Asp Pro
        1775                1780                1785
```

-continued

Glu Thr Gly Arg Asp Ile Pro Asn Pro Phe Ile Gly Ser Lys Ile
1790                1795                1800

Glu Phe Glu Gly Glu Asn Val His Thr Lys Arg Asp Ile Asn Arg
1805                1810                1815

Asp Arg Leu Phe Gln Gly Ser Thr Lys Thr His His Asn Trp Phe
1820                1825                1830

Ile Glu Gln Ala Leu Leu Ala Leu Glu Gln Thr Asn Tyr Cys Asp
1835                1840                1845

Phe Glu Val Gln Phe Glu Ile Met His Asn Gly Val His Thr Trp
1850                1855                1860

Val Gly Gly Lys Glu Pro Tyr Gly Ile Gly His Leu His Tyr Ala
1865                1870                1875

Ser Tyr Asp Pro Leu Phe Tyr Ile His His Ser Gln Thr Asp Arg
1880                1885                1890

Ile Trp Ala Ile Trp Gln Ser Leu Gln Arg Phe Arg Gly Leu Ser
1895                1900                1905

Gly Ser Glu Ala Asn Cys Ala Val Asn Leu Met Lys Thr Pro Leu
1910                1915                1920

Lys Pro Phe Ser Phe Gly Ala Pro Tyr Asn Leu Asn Asp His Thr
1925                1930                1935

His Asp Phe Ser Lys Pro Glu Asp Thr Phe Asp Tyr Gln Lys Phe
1940                1945                1950

Gly Tyr Ile Tyr Asp Thr Leu Glu Phe Ala Gly Trp Ser Ile Arg
1955                1960                1965

Gly Ile Asp His Ile Val Arg Asn Arg Gln Glu His Ser Arg Val
1970                1975                1980

Phe Ala Gly Phe Leu Leu Glu Gly Phe Gly Thr Ser Ala Thr Val
1985                1990                1995

Asp Phe Gln Val Cys Arg Thr Ala Gly Asp Cys Glu Asp Ala Gly
2000                2005                2010

Tyr Phe Thr Val Leu Gly Gly Glu Lys Glu Met Pro Trp Ala Phe
2015                2020                2025

Asp Arg Leu Tyr Lys Tyr Asp Ile Thr Glu Thr Leu Asp Lys Met
2030                2035                2040

Asn Leu Arg His Asp Glu Ile Phe Gln Ile Glu Val Thr Ile Thr
2045                2050                2055

Ser Tyr Asp Gly Thr Val Leu Asp Ser Gly Leu Ile Pro Thr Pro
2060                2065                2070

Ser Ile Ile Tyr Asp Pro Ala His His Asp Ile Ser Ser His His
2075                2080                2085

Leu Ser Leu Asn Lys Val Arg His Asp Leu Ser Thr Leu Ser Glu
2090                2095                2100

Arg Asp Ile Gly Ser Leu Lys Tyr Ala Leu Ser Ser Leu Gln Ala
2105                2110                2115

Asp Thr Ser Ala Asp Gly Phe Ala Ala Ile Ala Ser Phe His Gly
2120                2125                2130

Leu Pro Ala Lys Cys Asn Asp Ser His Asn Asn Glu Val Ala Cys
2135                2140                2145

Cys Ile His Gly Met Pro Thr Phe Pro His Trp His Arg Leu Tyr
2150                2155                2160

Thr Leu Gln Phe Glu Gln Ala Leu Arg Arg His Gly Ser Ser Val
2165                2170                2175

```
Ala Val Pro Tyr Trp Asp Trp Thr Lys Pro Ile His Asn Ile Pro
    2180                2185                2190

His Leu Phe Thr Asp Lys Glu Tyr Tyr Asp Val Trp Arg Asn Lys
    2195                2200                2205

Val Met Pro Asn Pro Phe Ala Arg Gly Tyr Val Pro Ser His Asp
    2210                2215                2220

Thr Tyr Thr Val Arg Asp Val Gln Glu Gly Leu Phe His Leu Thr
    2225                2230                2235

Ser Thr Gly Glu His Ser Ala Leu Leu Asn Gln Ala Leu Leu Ala
    2240                2245                2250

Leu Glu Gln His Asp Tyr Cys Asp Phe Ala Val Gln Phe Glu Val
    2255                2260                2265

Met His Asn Thr Ile His Tyr Leu Val Gly Gly Pro Gln Val Tyr
    2270                2275                2280

Ser Leu Ser Ser Leu His Tyr Ala Ser Tyr Asp Pro Ile Phe Phe
    2285                2290                2295

Ile His His Ser Phe Val Asp Lys Val Trp Ala Val Trp Gln Ala
    2300                2305                2310

Leu Gln Glu Lys Arg Gly Leu Pro Ser Asp Arg Ala Asp Cys Ala
    2315                2320                2325

Val Ser Leu Met Thr Gln Asn Met Arg Pro Phe His Tyr Glu Ile
    2330                2335                2340

Asn His Asn Gln Phe Thr Lys Lys His Ala Val Pro Asn Asp Val
    2345                2350                2355

Phe Lys Tyr Glu Leu Leu Gly Tyr Arg Tyr Asp Asn Leu Glu Ile
    2360                2365                2370

Gly Gly Met Asn Leu His Glu Ile Glu Lys Glu Ile Lys Asp Lys
    2375                2380                2385

Gln His His Val Arg Val Phe Ala Gly Phe Leu Leu His Gly Ile
    2390                2395                2400

Arg Thr Ser Ala Asp Val Gln Phe Gln Ile Cys Lys Thr Ser Glu
    2405                2410                2415

Asp Cys His His Gly Gly Gln Ile Phe Val Leu Gly Gly Thr Lys
    2420                2425                2430

Glu Met Ala Trp Ala Tyr Asn Arg Leu Phe Lys Tyr Asp Ile Thr
    2435                2440                2445

His Ala Leu His Asp Ala His Ile Thr Pro Glu Asp Val Phe His
    2450                2455                2460

Pro Ser Glu Pro Phe Phe Ile Lys Val Ser Val Thr Ala Val Asn
    2465                2470                2475

Gly Thr Val Leu Pro Ala Ser Ile Leu His Ala Pro Thr Ile Ile
    2480                2485                2490

Tyr Glu Pro Gly Leu Asp His His Glu Asp His His Ser Ser Ser
    2495                2500                2505

Met Ala Gly His Gly Val Arg Lys Glu Ile Asn Thr Leu Thr Thr
    2510                2515                2520

Ala Glu Val Asp Asn Leu Lys Asp Ala Met Arg Ala Val Met Ala
    2525                2530                2535

Asp His Gly Pro Asn Gly Tyr Gln Ala Ile Ala Ala Phe His Gly
    2540                2545                2550

Asn Pro Pro Met Cys Pro Met Pro Asp Gly Lys Asn Tyr Ser Cys
    2555                2560                2565

Cys Thr His Gly Met Ala Thr Phe Pro His Trp His Arg Leu Tyr
```

-continued

```
                2570                2575                2580
Thr Lys Gln Met Glu Asp Ala Leu Thr Ala His Gly Ala Arg Val
    2585                2590                2595
Gly Leu Pro Tyr Trp Asp Gly Thr Thr Ala Phe Thr Ala Leu Pro
    2600                2605                2610
Thr Phe Val Thr Asp Glu Glu Asp Asn Pro Phe His His Gly His
    2615                2620                2625
Ile Asp Tyr Leu Gly Val Asp Thr Thr Arg Ser Pro Arg Asp Lys
    2630                2635                2640
Leu Phe Asn Asp Pro Glu Arg Gly Ser Glu Ser Phe Phe Tyr Arg
    2645                2650                2655
Gln Val Leu Leu Ala Leu Glu Gln Thr Asp Phe Cys Gln Phe Glu
    2660                2665                2670
Val Gln Phe Glu Ile Thr His Asn Ala Ile His Ser Trp Thr Gly
    2675                2680                2685
Gly Leu Thr Pro Tyr Gly Met Ser Thr Leu Glu Tyr Thr Thr Tyr
    2690                2695                2700
Asp Pro Leu Phe Trp Leu His His Ala Asn Thr Asp Arg Ile Trp
    2705                2710                2715
Ala Ile Trp Gln Ala Leu Gln Glu Tyr Arg Gly Leu Pro Tyr Asp
    2720                2725                2730
His Ala Asn Cys Glu Ile Gln Ala Met Lys Arg Pro Leu Arg Pro
    2735                2740                2745
Phe Ser Asp Pro Ile Asn His Asn Ala Phe Thr His Ser Asn Ala
    2750                2755                2760
Lys Pro Thr Asp Val Phe Glu Tyr Ser Arg Phe Asn Phe Gln Tyr
    2765                2770                2775
Asp Asn Leu Arg Phe His Gly Met Thr Ile Lys Lys Leu Glu His
    2780                2785                2790
Glu Leu Glu Lys Gln Lys Glu Glu Asp Arg Thr Phe Ala Ala Phe
    2795                2800                2805
Leu Leu His Gly Ile Lys Lys Ser Ala Asp Val Ser Phe Asp Val
    2810                2815                2820
Cys Asn His Asp Gly Glu Cys His Phe Ala Gly Thr Phe Ala Ile
    2825                2830                2835
Leu Gly Gly Glu His Glu Met Pro Trp Ser Phe Asp Arg Leu Phe
    2840                2845                2850
Arg Tyr Asp Ile Thr Gln Val Leu Lys Gln Met His Leu Glu Tyr
    2855                2860                2865
Asp Ser Asp Phe Thr Phe His Met Arg Ile Ile Asp Thr Ser Gly
    2870                2875                2880
Lys Gln Leu Pro Ser Asp Leu Ile Lys Met Pro Thr Val Glu His
    2885                2890                2895
Ser Pro Gly Gly Lys His His Glu Lys His His Glu Asp His His
    2900                2905                2910
Glu Asp Ile Leu Val Arg Lys Asn Ile His Ser Leu Ser His His
    2915                2920                2925
Glu Ala Glu Glu Leu Arg Asp Ala Leu Tyr Lys Leu Gln Asn Asp
    2930                2935                2940
Glu Ser His Gly Gly Tyr Glu His Ile Ala Gly Phe His Gly Tyr
    2945                2950                2955
Pro Asn Leu Cys Pro Glu Lys Gly Asp Glu Lys Tyr Pro Cys Cys
    2960                2965                2970
```

-continued

Val His Gly Met Ser Ile Phe Pro His Trp His Arg Leu His Thr
2975                    2980              2985

Ile Gln Phe Glu Arg Ala Leu Lys Lys His Gly Ser His Leu Gly
2990                    2995              3000

Ile Pro Tyr Trp Asp Trp Thr Gln Thr Ile Ser Ser Leu Pro Thr
3005                    3010              3015

Phe Phe Ala Asp Ser Gly Asn Asn Asn Pro Phe Phe Lys Tyr His
3020                    3025              3030

Ile Arg Ser Ile Asn Gln Asp Thr Val Arg Asp Val Asn Glu Ala
3035                    3040              3045

Ile Phe Gln Gln Thr Lys Phe Gly Glu Phe Ser Ser Ile Phe Tyr
3050                    3055              3060

Leu Ala Leu Gln Ala Leu Glu Glu Asp Asn Tyr Cys Asp Phe Glu
3065                    3070              3075

Val Gln Tyr Glu Ile Leu His Asn Glu Val His Ala Leu Ile Gly
3080                    3085              3090

Gly Ala Glu Lys Tyr Ser Met Ser Thr Leu Glu Tyr Ser Ala Phe
3095                    3100              3105

Asp Pro Tyr Phe Met Ile His His Ala Ser Leu Asp Lys Ile Trp
3110                    3115              3120

Ile Ile Trp Gln Glu Leu Gln Lys Arg Arg Val Lys Pro Ala His
3125                    3130              3135

Ala Gly Ser Cys Ala Gly Asp Ile Met His Val Pro Leu His Pro
3140                    3145              3150

Phe Asn Tyr Glu Ser Val Asn Asn Asp Asp Phe Thr Arg Glu Asn
3155                    3160              3165

Ser Leu Pro Asn Ala Val Val Asp Ser His Arg Phe Asn Tyr Lys
3170                    3175              3180

Tyr Asp Asn Leu Asn Leu His Gly His Asn Ile Glu Glu Leu Glu
3185                    3190              3195

Glu Val Leu Arg Ser Leu Arg Leu Lys Ser Arg Val Phe Ala Gly
3200                    3205              3210

Phe Val Leu Ser Gly Ile Arg Thr Thr Ala Val Val Lys Val Tyr
3215                    3220              3225

Ile Lys Ser Gly Thr Asp Ser Asp Asp Glu Tyr Ala Gly Ser Phe
3230                    3235              3240

Val Ile Leu Gly Gly Ala Lys Glu Met Pro Trp Ala Tyr Glu Arg
3245                    3250              3255

Leu Tyr Arg Phe Asp Ile Thr Glu Thr Val His Asn Leu Asn Leu
3260                    3265              3270

Thr Asp Asp His Val Lys Phe Arg Phe Asp Leu Lys Lys Tyr Asp
3275                    3280              3285

His Thr Glu Leu Asp Ala Ser Val Leu Pro Ala Pro Ile Ile Val
3290                    3295              3300

Arg Arg Pro Asn Asn Ala Val Phe Asp Ile Ile Glu Ile Pro Ile
3305                    3310              3315

Gly Lys Asp Val Asn Leu Pro Pro Lys Val Val Val Lys Arg Gly
3320                    3325              3330

Thr Lys Ile Met Phe Met Ser Val Asp Glu Ala Val Thr Thr Pro
3335                    3340              3345

Met Leu Asn Leu Gly Ser Tyr Thr Ala Met Phe Lys Cys Lys Val
3350                    3355              3360

```
Pro Pro Phe Ser Phe His Ala Phe Glu Leu Gly Lys Met Tyr Ser
    3365            3370                3375

Val Glu Ser Gly Asp Tyr Phe Met Thr Ala Ser Thr Thr Glu Leu
    3380            3385                3390

Cys Asn Asp Asn Asn Leu Arg Ile His Val His Val Asp Asp Glu
    3395            3400                3405

<210> SEQ ID NO 7
<211> LENGTH: 128
<212> TYPE: PRT
<213> ORGANISM: Bos taurus

<400> SEQUENCE: 7

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Ile Ile Glu Pro
65                  70                  75                  80

Ser Leu Arg Gln Leu Ala Gln Lys Tyr Asn Cys Asp Lys Met Ile Cys
                85                  90                  95

Arg Lys Cys Tyr Ala Arg Leu His Pro Arg Ala Val Asn Cys Arg Lys
            100                 105                 110

Lys Lys Cys Gly His Thr Asn Asn Leu Arg Pro Lys Lys Val Lys
        115                 120                 125

<210> SEQ ID NO 8
<211> LENGTH: 624
<212> TYPE: DNA
<213> ORGANISM: Bos taurus

<400> SEQUENCE: 8
ctcttcaacc aggcggccga gcagcaggcg cagagatgca gatctttgtg aagaccctga      60
cgggcaagac catcacccct gaggtcgagc ccagtgacac cattgagaat gtcaaagcca     120
aaatccaaga caaggagggc atcccacctg accagcagcg gctgatcttc gctggcaaac     180
agctggagga tggccgcact ctgtcagatt ataatatcca gaaagagtcc accctgcact     240
tggtgcttcg tctgcgaggc ggcatcatcg agccttccct ccgccagctc gctcagaaat     300
acaactgcga caagatgatc tgccgcaagt gttacgcccg cctgcacccc cgtgctgtca     360
actgccgcaa gaagaagtgt ggccacacca caaacctgcg ccccaagaag aaggtcaaat     420
aaagctcttc cacctgcttc tcctttgccc gcagggcggc ctcctgccca gccccgtgg      480 tcctgggcct caataaagtt tccctttcgt tgactggagc agtaaaaaaa aaaaaaaaa      540 aaaaaaaaaa aaaaaaaaaa aaaaaaaaaa aaaaaaaaaa aaaaaaaaaa aaaaaaaaaa     600
aaaaaaagaa aaaaaaaaaa aaaa                                           624

<210> SEQ ID NO 9
<211> LENGTH: 15
<212> TYPE: PRT
<213> ORGANISM: Measles virus

<400> SEQUENCE: 9
```

```
Leu Ser Glu Ile Lys Gly Val Ile Val His Arg Leu Glu Gly Val
1               5                   10                  15

<210> SEQ ID NO 10
<211> LENGTH: 1315
<212> TYPE: PRT
<213> ORGANISM: Clostridium tetani

<400> SEQUENCE: 10

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
        355                 360                 365
```

```
Ile Lys Thr Arg Leu Ser Tyr Phe Ser Met Asn His Asp Pro Val Lys
    370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
        435                 440                 445

Arg Glu Asn Leu Tyr Asn Arg Thr Ala Ser Leu Thr Asp Leu Gly Gly
    450                 455                 460

Glu Leu Cys Ile Lys Ile Lys Asn Glu Asp Leu Thr Phe Ile Ala Glu
465                 470                 475                 480

Lys Asn Ser Phe Ser Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
        515                 520                 525

Thr Thr Pro Val Thr Lys Gly Ile Pro Tyr Ala Pro Glu Tyr Lys Ser
    530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
        595                 600                 605

Gly Ile Leu Phe Leu Gln Trp Val Arg Asp Ile Ile Asp Asp Phe Thr
    610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
        675                 680                 685

Ser Ile Ala Glu Ser Ser Thr Gln Lys Glu Lys Ile Ile Lys Thr Ile
    690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Lys
        755                 760                 765

Glu Gln Ile Ala Asp Glu Ile Asn Asn Leu Lys Asn Lys Leu Glu Glu
    770                 775                 780
```

```
Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
            805                 810                 815

Leu Leu Glu Phe Asp Thr Gln Ser Lys Asn Ile Leu Met Gln Tyr Ile
            820                 825                 830

Lys Ala Asn Ser Lys Phe Ile Gly Ile Thr Glu Leu Lys Lys Leu Glu
            835                 840                 845

Ser Lys Ile Asn Lys Val Phe Ser Thr Pro Ile Pro Phe Ser Tyr Ser
850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
                900                 905                 910

Gln Leu Val Pro Gly Ile Asn Gly Lys Ala Ile His Leu Val Asn Asn
            915                 920                 925

Glu Ser Ser Glu Val Ile Val His Lys Ala Met Asp Ile Glu Tyr Asn
930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                965                 970                 975

Ile Ser Ser Met Lys Lys His Ser Leu Ser Ile Gly Ser Gly Trp Ser
                980                 985                 990

Val Ser Leu Lys Gly Asn Asn Leu Ile Trp Thr Leu Lys Asp Ser Ala
            995                 1000                1005

Gly Glu Val Arg Gln Ile Thr Phe Arg Asp Leu Pro Asp Lys Phe
    1010                1015                1020

Asn Ala Tyr Leu Ala Asn Lys Trp Val Phe Ile Thr Ile Thr Asn
    1025                1030                1035

Asp Arg Leu Ser Ser Ala Asn Leu Tyr Ile Asn Gly Val Leu Met
    1040                1045                1050

Gly Ser Ala Glu Ile Thr Gly Leu Gly Ala Ile Arg Glu Asp Asn
    1055                1060                1065

Asn Ile Thr Leu Lys Leu Asp Arg Cys Asn Asn Asn Asn Gln Tyr
    1070                1075                1080

Val Ser Ile Asp Lys Phe Arg Ile Phe Cys Lys Ala Leu Asn Pro
    1085                1090                1095

Lys Glu Ile Glu Lys Leu Tyr Thr Ser Tyr Leu Ser Ile Thr Phe
    1100                1105                1110

Leu Arg Asp Phe Trp Gly Asn Pro Leu Arg Tyr Asp Thr Glu Tyr
    1115                1120                1125

Tyr Leu Ile Pro Val Ala Ser Ser Ser Lys Asp Val Gln Leu Lys
    1130                1135                1140

Asn Ile Thr Asp Tyr Met Tyr Leu Thr Asn Ala Pro Ser Tyr Thr
    1145                1150                1155

Asn Gly Lys Leu Asn Ile Tyr Tyr Arg Arg Leu Tyr Asn Gly Leu
    1160                1165                1170

Lys Phe Ile Ile Lys Arg Tyr Thr Pro Asn Asn Glu Ile Asp Ser
    1175                1180                1185

Phe Val Lys Ser Gly Asp Phe Ile Lys Leu Tyr Val Ser Tyr Asn
```

```
                    1190                1195                1200
Asn  Asn  Glu  His  Ile  Val  Gly  Tyr  Pro  Lys  Asp  Gly  Asn  Ala  Phe
     1205                1210                1215

Asn  Asn  Leu  Asp  Arg  Ile  Leu  Arg  Val  Gly  Tyr  Asn  Ala  Pro  Gly
     1220                1225                1230

Ile  Pro  Leu  Tyr  Lys  Lys  Met  Glu  Ala  Val  Lys  Leu  Arg  Asp  Leu
     1235                1240                1245

Lys  Thr  Tyr  Ser  Val  Gln  Leu  Lys  Leu  Tyr  Asp  Lys  Asn  Ala
     1250                1255                1260

Ser  Leu  Gly  Leu  Val  Gly  Thr  His  Asn  Gly  Gln  Ile  Gly  Asn  Asp
     1265                1270                1275

Pro  Asn  Arg  Asp  Ile  Leu  Ile  Ala  Ser  Asn  Trp  Tyr  Phe  Asn  His
     1280                1285                1290

Leu  Lys  Asp  Lys  Ile  Leu  Gly  Cys  Asp  Trp  Tyr  Phe  Val  Pro  Thr
     1295                1300                1305

Asp  Glu  Gly  Trp  Thr  Asn  Asp
     1310                1315
```

<210> SEQ ID NO 11
<211> LENGTH: 18
<212> TYPE: PRT
<213> ORGANISM: Clostridium tetani

<400> SEQUENCE: 11

```
Val  Asp  Asp  Ala  Leu  Ile  Asn  Ser  Thr  Lys  Ile  Tyr  Ser  Tyr  Phe  Pro
1                   5                   10                  15

Ser  Val
```

<210> SEQ ID NO 12
<211> LENGTH: 15
<212> TYPE: PRT
<213> ORGANISM: Clostridium tetani

<400> SEQUENCE: 12

```
Gln  Tyr  Ile  Lys  Ala  Asn  Ser  Lys  Phe  Ile  Gly  Ile  Thr  Glu  Leu
1                   5                   10                  15
```

<210> SEQ ID NO 13
<211> LENGTH: 21
<212> TYPE: PRT
<213> ORGANISM: Clostridium tetani

<400> SEQUENCE: 13

```
Phe  Asn  Asn  Phe  Thr  Val  Ser  Phe  Trp  Leu  Arg  Val  Pro  Lys  Val  Ser
1                   5                   10                  15

Ala  Ser  His  Leu  Glu
                20
```

<210> SEQ ID NO 14
<211> LENGTH: 11
<212> TYPE: PRT
<213> ORGANISM: Anaplasma marginale

<400> SEQUENCE: 14

```
Ser  Ser  Ala  Gly  Gly  Gln  Gln  Gln  Glu  Ser  Ser
1                   5                   10
```

<210> SEQ ID NO 15
<211> LENGTH: 20
<212> TYPE: PRT

<213> ORGANISM: Plasmodium falciparum

<400> SEQUENCE: 15

Asp Glu Lys Lys Ile Ala Lys Met Glu Lys Ala Ser Ser Val Phe Asn
1               5                   10                  15

Val Val Asn Ser
            20

<210> SEQ ID NO 16
<211> LENGTH: 18
<212> TYPE: PRT
<213> ORGANISM: Unknown
<220> FEATURE:
<223> OTHER INFORMATION: Influenza HA B epitope

<400> SEQUENCE: 16

Ser Lys Ala Phe Ser Asn Cys Tyr Pro Tyr Asp Val Pro Asp Tyr Ala
1               5                   10                  15

Ser Leu

<210> SEQ ID NO 17
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 17

Ala Lys Xaa Val Ala Ala Trp Thr Leu Lys Ala Ala
1               5                   10

<210> SEQ ID NO 18
<211> LENGTH: 11
<212> TYPE: PRT
<213> ORGANISM: Unknown
<220> FEATURE:
<223> OTHER INFORMATION: Concholepas concholepas

<400> SEQUENCE: 18

Leu Met Arg Lys Asp Val Asp Thr Leu Thr Asp
1               5                   10

<210> SEQ ID NO 19
<211> LENGTH: 7
<212> TYPE: PRT
<213> ORGANISM: Unknown
<220> FEATURE:
<223> OTHER INFORMATION: Concholepas concholepas
<220> FEATURE:
<221> NAME/KEY: misc_feature
<222> LOCATION: (2)..(2)
<223> OTHER INFORMATION: Xaa can be any naturally occurring amino acid

<400> SEQUENCE: 19

Leu Xaa Arg Lys Asn Val Asp
1               5

<210> SEQ ID NO 20
<211> LENGTH: 386
<212> TYPE: PRT
<213> ORGANISM: Gallus gallus

<400> SEQUENCE: 20

```
Met Gly Ser Ile Gly Ala Ala Ser Met Glu Phe Cys Phe Asp Val Phe
1               5                  10                  15

Lys Glu Leu Lys Val His His Ala Asn Glu Asn Ile Phe Tyr Cys Pro
                20                  25                  30

Ile Ala Ile Met Ser Ala Leu Ala Met Val Tyr Leu Gly Ala Lys Asp
            35                  40                  45

Ser Thr Arg Thr Gln Ile Asn Lys Val Val Arg Phe Asp Lys Leu Pro
50                  55                  60

Gly Phe Gly Asp Ser Ile Glu Ala Gln Cys Gly Thr Ser Val Asn Val
65                  70                  75                  80

His Ser Ser Leu Arg Asp Ile Leu Asn Gln Ile Thr Lys Pro Asn Asp
                85                  90                  95

Val Tyr Ser Phe Ser Leu Ala Ser Arg Leu Tyr Ala Glu Glu Arg Tyr
                100                 105                 110

Pro Ile Leu Pro Glu Tyr Leu Gln Cys Val Lys Glu Leu Tyr Arg Gly
                115                 120                 125

Gly Leu Glu Pro Ile Asn Phe Gln Thr Ala Ala Asp Gln Ala Arg Glu
            130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
                165                 170                 175

Asn Ala Ile Val Phe Lys Gly Leu Trp Glu Lys Ala Phe Lys Asp Glu
                180                 185                 190

Asp Thr Gln Ala Met Pro Phe Arg Val Thr Glu Gln Glu Ser Lys Pro
            195                 200                 205

Val Gln Met Met Tyr Gln Ile Gly Leu Phe Arg Val Ala Ser Met Ala
210                 215                 220

Ser Glu Lys Met Lys Ile Leu Glu Leu Pro Phe Ala Ser Gly Thr Met
225                 230                 235                 240

Ser Met Leu Val Leu Leu Pro Asp Glu Val Ser Gly Leu Glu Gln Leu
                245                 250                 255

Glu Ser Ile Ile Asn Phe Glu Lys Leu Thr Glu Trp Thr Ser Ser Asn
                260                 265                 270

Val Met Glu Glu Arg Lys Ile Lys Val Tyr Leu Pro Arg Met Lys Met
            275                 280                 285

Glu Glu Lys Tyr Asn Leu Thr Ser Val Leu Met Ala Met Gly Ile Thr
290                 295                 300

Asp Val Phe Ser Ser Ser Ala Asn Leu Ser Gly Ile Ser Ser Ala Glu
305                 310                 315                 320

Ser Leu Lys Ile Ser Gln Ala Val His Ala His Ala Glu Ile Asn
                325                 330                 335

Glu Ala Gly Arg Glu Val Val Gly Ser Ala Glu Ala Gly Val Asp Ala
            340                 345                 350

Ala Ser Val Ser Glu Glu Phe Arg Ala Asp His Pro Phe Leu Phe Cys
                355                 360                 365

Ile Lys His Ile Ala Thr Asn Ala Val Leu Phe Phe Gly Arg Cys Val
            370                 375                 380

Ser Pro
385

<210> SEQ ID NO 21
<211> LENGTH: 607
```

<212> TYPE: PRT
<213> ORGANISM: Bos taurus

<400> SEQUENCE: 21

Met Lys Trp Val Thr Phe Ile Ser Leu Leu Leu Phe Ser Ser Ala
1               5                   10                  15

Tyr Ser Arg Gly Val Phe Arg Arg Asp Thr His Lys Ser Glu Ile Ala
            20                  25                  30

His Arg Phe Lys Asp Leu Gly Glu Glu His Phe Lys Gly Leu Val Leu
                35                  40                  45

Ile Ala Phe Ser Gln Tyr Leu Gln Gln Cys Pro Phe Asp Glu His Val
        50                  55                  60

Lys Leu Val Asn Glu Leu Thr Glu Phe Ala Lys Thr Cys Val Ala Asp
65                  70                  75                  80

Glu Ser His Ala Gly Cys Glu Lys Ser Leu His Thr Leu Phe Gly Asp
                85                  90                  95

Glu Leu Cys Lys Val Ala Ser Leu Arg Glu Thr Tyr Gly Asp Met Ala
            100                 105                 110

Asp Cys Cys Glu Lys Gln Glu Pro Glu Arg Asn Glu Cys Phe Leu Ser
        115                 120                 125

His Lys Asp Asp Ser Pro Asp Leu Pro Lys Leu Lys Pro Asp Pro Asn
        130                 135                 140

Thr Leu Cys Asp Glu Phe Lys Ala Asp Glu Lys Lys Phe Trp Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala Asn Lys Tyr Asn Gly Val Phe Gln Glu Cys Cys
            180                 185                 190

Gln Ala Glu Asp Lys Gly Ala Cys Leu Leu Pro Lys Ile Glu Thr Met
        195                 200                 205

Arg Glu Lys Val Leu Ala Ser Ser Ala Arg Gln Arg Leu Arg Cys Ala
            210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Glu Phe Val Glu Val Thr Lys
                245                 250                 255

Leu Val Thr Asp Leu Thr Lys Val His Lys Glu Cys Cys His Gly Asp
            260                 265                 270

Leu Leu Glu Cys Ala Asp Asp Arg Ala Asp Leu Ala Lys Tyr Ile Cys
        275                 280                 285

Asp Asn Gln Asp Thr Ile Ser Ser Lys Leu Lys Glu Cys Cys Asp Lys
290                 295                 300

Pro Leu Leu Glu Lys Ser His Cys Ile Ala Glu Val Glu Lys Asp Ala
305                 310                 315                 320

Ile Pro Glu Asn Leu Pro Pro Leu Thr Ala Asp Phe Ala Glu Asp Lys
                325                 330                 335

Asp Val Cys Lys Asn Tyr Gln Glu Ala Lys Asp Ala Phe Leu Gly Ser
            340                 345                 350

Phe Leu Tyr Glu Tyr Ser Arg Arg His Pro Glu Tyr Ala Val Ser Val
        355                 360                 365

Leu Leu Arg Leu Ala Lys Glu Tyr Glu Ala Thr Leu Glu Glu Cys Cys
        370                 375                 380

Ala Lys Asp Asp Pro His Ala Cys Tyr Ser Thr Val Phe Asp Lys Leu
385                 390                 395                 400

```
Lys His Leu Val Asp Glu Pro Gln Asn Leu Ile Lys Gln Asn Cys Asp
                405                 410                 415
Gln Phe Glu Lys Leu Gly Glu Tyr Gly Phe Gln Asn Ala Leu Ile Val
            420                 425                 430
Arg Tyr Thr Arg Lys Val Pro Gln Val Ser Thr Pro Thr Leu Val Glu
        435                 440                 445
Val Ser Arg Ser Leu Gly Lys Val Gly Thr Arg Cys Cys Thr Lys Pro
450                 455                 460
Glu Ser Glu Arg Met Pro Cys Thr Glu Asp Tyr Leu Ser Leu Ile Leu
465                 470                 475                 480
Asn Arg Leu Cys Val Leu His Glu Lys Thr Pro Val Ser Glu Lys Val
                485                 490                 495
Thr Lys Cys Cys Thr Glu Ser Leu Val Asn Arg Arg Pro Cys Phe Ser
            500                 505                 510
Ala Leu Thr Pro Asp Glu Thr Tyr Val Pro Lys Ala Phe Asp Glu Lys
        515                 520                 525
Leu Phe Thr Phe His Ala Asp Ile Cys Thr Leu Pro Asp Thr Glu Lys
    530                 535                 540
Gln Ile Lys Lys Gln Thr Ala Leu Val Glu Leu Leu Lys His Lys Pro
545                 550                 555                 560
Lys Ala Thr Glu Glu Gln Leu Lys Thr Val Met Glu Asn Phe Val Ala
                565                 570                 575
Phe Val Asp Lys Cys Cys Ala Ala Asp Asp Lys Glu Ala Cys Phe Ala
            580                 585                 590
Val Glu Gly Pro Lys Leu Val Val Ser Thr Gln Thr Ala Leu Ala
        595                 600                 605

<210> SEQ ID NO 22
<211> LENGTH: 124
<212> TYPE: PRT
<213> ORGANISM: Vibrio cholerae

<400> SEQUENCE: 22

Met Ile Lys Leu Lys Phe Gly Val Phe Phe Thr Val Leu Leu Ser Ser
1               5                   10                  15
Ala Tyr Ala His Gly Thr Pro Gln Asn Ile Thr Asp Leu Cys Ala Glu
                20                  25                  30
Tyr His Asn Thr Gln Ile Tyr Thr Leu Asn Asp Lys Ile Phe Ser Tyr
            35                  40                  45
Thr Glu Ser Leu Ala Gly Lys Arg Glu Met Ala Ile Ile Thr Phe Lys
        50                  55                  60
Asn Gly Ala Ile Phe Gln Val Glu Val Pro Gly Ser Gln His Ile Asp
65                  70                  75                  80
Ser Gln Lys Lys Ala Ile Glu Arg Met Lys Asp Thr Leu Arg Ile Ala
                85                  90                  95
Tyr Leu Thr Glu Ala Lys Val Glu Lys Leu Cys Val Trp Asn Asn Lys
            100                 105                 110
Thr Pro His Ala Ile Ala Ala Ile Ser Met Ala Asn
        115                 120

<210> SEQ ID NO 23
<211> LENGTH: 9
<212> TYPE: PRT
<213> ORGANISM: Unknown
<220> FEATURE:
<223> OTHER INFORMATION: Cytomegalovirus
```

<400> SEQUENCE: 23

Asn Leu Val Pro Met Val Ala Thr Val
1               5

<210> SEQ ID NO 24
<211> LENGTH: 14
<212> TYPE: PRT
<213> ORGANISM: Rhipicephalus microplus

<400> SEQUENCE: 24

Trp Arg Trp Thr Ile Phe Thr Gly Glu Thr Pro Phe Gln Lys
1               5                   10

<210> SEQ ID NO 25
<211> LENGTH: 7
<212> TYPE: PRT
<213> ORGANISM: Rhipicephalus microplus

<400> SEQUENCE: 25

Leu Arg Glu Ile Tyr Pro Gly
1               5

<210> SEQ ID NO 26
<211> LENGTH: 8
<212> TYPE: PRT
<213> ORGANISM: Rhipicephalus microplus

<400> SEQUENCE: 26

Asn Glu Val Val Gly Trp Asp Lys
1               5

<210> SEQ ID NO 27
<211> LENGTH: 10
<212> TYPE: PRT
<213> ORGANISM: Rhipicephalus microplus

<400> SEQUENCE: 27

Leu Trp Glu Asp Leu Ser Pro Leu Tyr Lys
1               5                   10

<210> SEQ ID NO 28
<211> LENGTH: 8
<212> TYPE: PRT
<213> ORGANISM: Rhipicephalus microplus

<400> SEQUENCE: 28

Gln Tyr Tyr Ile Pro Tyr Ile Lys
1               5

<210> SEQ ID NO 29
<211> LENGTH: 7
<212> TYPE: PRT
<213> ORGANISM: Rhipicephalus microplus

<400> SEQUENCE: 29

Tyr Tyr Glu Pro Leu Glu Lys
1               5

<210> SEQ ID NO 30
<211> LENGTH: 45
<212> TYPE: PRT
<213> ORGANISM: Rhipicephalus microplus

<400> SEQUENCE: 30

```
Cys Leu Ser Lys His Val Leu Arg Lys Leu Gln Ala Cys Glu His Ser
1               5                   10                  15

Ser Ile Cys Ser Asp Phe Gly Asn Glu Phe Cys Arg Asn Ala Cys Asp
                20                  25                  30

Cys Gly Glu Trp Gly Ala Met Asn Met Thr Thr Arg Cys
            35              40              45

<210> SEQ ID NO 31
<211> LENGTH: 45
<212> TYPE: PRT
<213> ORGANISM: Rhipicephalus microplus

<400> SEQUENCE: 31

Cys Leu Ser Lys His Val Leu Arg Lys Leu Gln Ala Cys Glu His Cys
1               5                   10                  15

Asp Cys Gly Glu Trp Gly Ala Met Asn Met Thr Thr Arg Ser Ser Ile
                20                  25                  30

Cys Ser Asp Phe Gly Asn Glu Phe Cys Arg Asn Ala Cys
            35              40              45

<210> SEQ ID NO 32
<211> LENGTH: 51
<212> TYPE: PRT
<213> ORGANISM: Rhipicephalus microplus

<400> SEQUENCE: 32

Cys Leu Ser Lys His Val Leu Arg Lys Leu Gln Ala Cys Glu His Lys
1               5                   10                  15

Glu Lys Ser Ser Ile Cys Ser Asp Phe Gly Asn Glu Phe Cys Arg Asn
                20                  25                  30

Ala Lys Glu Lys Cys Asp Cys Gly Glu Trp Gly Ala Met Asn Met Thr
            35              40              45

Thr Arg Cys
    50
```